(12) United States Patent
Taft et al.

(10) Patent No.: US 8,524,259 B2
(45) Date of Patent: *Sep. 3, 2013

(54) SYSTEMS AND METHODS FOR DELIVERY OF MATERIALS

(75) Inventors: David D. Taft, Atherton, CA (US);
Steven Bitler, Menlo Park, CA (US);
Qiang Zheng, Palo Alto, CA (US);
Stelios Tzannis, Newark, CA (US);
Adam Bell, Portsmouth, NH (US);
Wei-Guo Dai, Sunnyvale, CA (US);
Sandra N. Ottensmann, Mountain View, CA (US); Natarajan Balachander, West Lafayette, IN (US)

(73) Assignee: Landec Corporation, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/746,178

(22) PCT Filed: Dec. 3, 2008

(86) PCT No.: PCT/US2008/013335
§ 371 (c)(1),
(2), (4) Date: Sep. 30, 2010

(87) PCT Pub. No.: WO2009/073192
PCT Pub. Date: Jun. 11, 2009

(65) Prior Publication Data
US 2011/0009571 A1   Jan. 13, 2011

(51) Int. Cl.
*C08G 63/06* (2006.01)
(52) U.S. Cl.
USPC ............. 424/401; 424/405; 424/59; 424/65; 424/94.1; 525/450
(58) Field of Classification Search
None
See application file for complete search history.

(56) References Cited

U.S. PATENT DOCUMENTS

| | | | |
|---|---|---|---|
| 3,608,549 A | 9/1971 | Merrill | |
| 4,558,690 A | 12/1985 | Joyce | |
| 4,830,855 A | 5/1989 | Stewart | |
| 4,851,521 A * | 7/1989 | della Valle et al. | ........... 536/55.1 |
| 5,120,349 A | 6/1992 | Stewart | |
| 5,129,180 A | 7/1992 | Stewart | |
| 5,143,730 A | 9/1992 | Fues et al. | |
| 5,156,911 A | 10/1992 | Stewart | |
| 5,213,808 A | 5/1993 | Bar-Shalom et al. | |
| 5,308,623 A | 5/1994 | Fues et al. | |
| 5,384,333 A | 1/1995 | Davis et al. | |
| 5,387,450 A | 2/1995 | Stewart | |
| 5,412,035 A | 5/1995 | Schmitt et al. | |
| 5,429,654 A | 7/1995 | Swarup | |
| 5,469,867 A | 11/1995 | Schmitt | |
| 5,662,711 A | 9/1997 | Douglas | |
| 5,665,822 A | 9/1997 | Bitler | |
| 5,687,718 A | 11/1997 | Fischer et al. | |
| 5,725,881 A | 3/1998 | Buchholz | |
| 5,783,302 A * | 7/1998 | Bitler et al. | .................... 428/343 |
| 5,826,584 A | 10/1998 | Schmitt | |
| 5,852,117 A | 12/1998 | Schoenberg et al. | |
| 5,895,404 A | 4/1999 | Ruiz | |
| 5,945,457 A | 8/1999 | Plate et al. | |
| 6,001,395 A | 12/1999 | Coombes et al. | |
| 6,004,549 A | 12/1999 | Reichert et al. | |
| 6,199,318 B1 | 3/2001 | Stewart | |
| 6,214,901 B1 | 4/2001 | Chudzik | |
| 6,224,793 B1 | 5/2001 | Hoffman | |
| 6,255,367 B1 | 7/2001 | Bitler | |
| 6,297,337 B1 | 10/2001 | Marchant et al. | |
| 6,319,521 B1 | 11/2001 | Randolph | |
| 6,344,035 B1 | 2/2002 | Cudzik | |
| 6,352,667 B1 | 3/2002 | English | |
| 6,423,345 B2 | 7/2002 | Berstein et al. | |
| 6,469,133 B2 | 10/2002 | Baker et al. | |

(Continued)

FOREIGN PATENT DOCUMENTS

| | | |
|---|---|---|
| AR | 070104879 | 5/2009 |
| DE | 19908753 | 8/2000 |

(Continued)

OTHER PUBLICATIONS

Gaska, Fungicide Seed Treatments for Soybean, 2004.*
Lee, J. et al., "Thermosenstive Permeation From Side-Chain Crystalline Ionomers", Journal of Polymer Science: Part B: Polymer Physics, vol. 38, pp. 823-830; 2000.
Mohr, J.M., et al., "Drug Delivery with Side Chain Crystallizable Polymer Blends", 1991; Proceedings of the 18th International Symposium on Controlled Release of Bioactive Materials, pp. 409-410; Controlled Release Society, U.S.A.
Mohr, J.M., et al., "Pulsatile Transdermal Drug Delivery", 1992; Proceedings of the 19th International Symposium on Controlled Release of Bioactive Materials, pp. 377-378; Controlled Release Society, U.S.A.

(Continued)

*Primary Examiner* — Robert A Wax
*Assistant Examiner* — William Craigo

(57) ABSTRACT

Systems and methods for delivering release materials, for example drugs and other bioactive materials. Crystalline polymeric systems, referred to as CYC carriers, are associated with the release materials, through chemical bonding or through physical association. The crystallinity of the CYC carriers results from the presence of crystallizable side chains, for example long chain n-alkyl moieties, which results in relatively low and sharp melting temperatures. One class of CYC carriers, referred to as CYSC polymers, have a majority of the crystallizable side chains pendant from the polymer backbone. Another class of CYC carriers referred to as ECC polymers, have a majority of the crystallizable side chains attached to terminal units of the polymer backbone. The ECC polymers can for example be obtained by modification of PLGA polymers. The CYC carriers in another class of non-polymeric. Some CYC carriers, referred to as CYC assemblies, have enhanced crystallinity as a result of the physical association of crystallizable moieties which are present in different types of molecule, for example between a polymer containing crystallizable moieties and a monomer containing crystallizable moieties. For some uses, particularly the delivery of drugs, a bioerodable CYC carrier is preferably used.

21 Claims, 18 Drawing Sheets

(56) References Cited

U.S. PATENT DOCUMENTS

| | | |
|---|---|---|
| 6,524,274 B1 | 2/2003 | Rosenthal |
| 6,528,080 B2 | 3/2003 | Dunn et al. |
| 6,540,984 B2 | 4/2003 | Stewart |
| 6,569,128 B1 | 5/2003 | Christensen et al. |
| 6,576,254 B1 | 6/2003 | Uchegbu |
| 6,653,395 B1 | 11/2003 | Bergstrom et al. |
| 6,656,385 B2 | 12/2003 | Lynch |
| 6,657,042 B2 | 12/2003 | Rafier et al. |
| 6,699,952 B2 | 3/2004 | Chaikof |
| 6,730,322 B1 | 5/2004 | Berstein et al. |
| 6,780,930 B2 | 8/2004 | Lewis |
| 6,815,469 B1 | 11/2004 | Voelkel |
| 6,831,116 B2 | 12/2004 | Bitler |
| 6,858,634 B2 | 2/2005 | Asrar et al. |
| 6,866,860 B2 | 3/2005 | Nathan |
| 6,887,960 B2 | 5/2005 | Parker et al. |
| 6,890,583 B2 | 5/2005 | Chudzik |
| 6,951,642 B2 | 10/2005 | Scholz et al. |
| 6,964,778 B1 | 11/2005 | Hui |
| 6,967,234 B2 * | 11/2005 | Nathan .................. 528/272 |
| 6,989,417 B2 | 1/2006 | Bitler et al. |
| 7,008,667 B2 | 3/2006 | Chudnik |
| 7,030,084 B2 | 4/2006 | Ekwuribe et al. |
| 7,083,572 B2 | 8/2006 | Unger et al. |
| 7,220,430 B2 | 5/2007 | Ishibashi et al. |
| 2002/0106406 A1 | 8/2002 | McHugh et al. |
| 2002/0114827 A1 | 8/2002 | Zhang |
| 2002/0161437 A1 | 10/2002 | Zhou et al. |
| 2003/0003125 A1* | 1/2003 | Nathan et al. ............. 424/408 |
| 2003/0082217 A1 | 5/2003 | Afriat |
| 2003/0224974 A1 | 12/2003 | Bolotin |
| 2004/0009229 A1 | 1/2004 | Unger |
| 2004/0052746 A1 | 3/2004 | Tamareselvy |
| 2004/0117006 A1 | 6/2004 | Lewis et al. |
| 2004/0127579 A1* | 7/2004 | Lannibois-Drean et al. ... 516/21 |
| 2004/0208844 A1 | 10/2004 | Ignatious |
| 2004/0236013 A1 | 11/2004 | Lewis |
| 2004/0254419 A1 | 12/2004 | Wang et al. |
| 2005/0019923 A1 | 1/2005 | Uchegbu et al. |
| 2005/0169977 A1 | 8/2005 | Kanios et al. |
| 2005/0197251 A1 | 9/2005 | Ding et al. |
| 2005/0249697 A1 | 11/2005 | Uhrich et al. |
| 2005/0249799 A1 | 11/2005 | Jacob |
| 2006/0018948 A1 | 1/2006 | Guire |
| 2006/0024361 A1 | 2/2006 | Odidi |
| 2006/0034891 A1 | 2/2006 | Lawin et al. |
| 2006/0148982 A1 | 7/2006 | Uchegbu et al. |
| 2006/0167116 A1 | 7/2006 | Uchegbu et al. |
| 2006/0286064 A1 | 12/2006 | Turnell et al. |
| 2006/0292222 A1 | 12/2006 | Jonasse |
| 2007/0016284 A1 | 1/2007 | Pacetti |
| 2007/0134310 A1 | 6/2007 | Nedberge et al. |
| 2007/0142461 A1 | 6/2007 | Baker et al. |
| 2007/0259584 A1 | 11/2007 | Whitehouse |
| 2009/0124996 A1 | 5/2009 | Krumme |
| 2009/0177158 A1 | 7/2009 | Krumme |
| 2009/0198183 A1 | 8/2009 | Krumme |
| 2009/0240200 A1 | 9/2009 | Krumme |

FOREIGN PATENT DOCUMENTS

| | | |
|---|---|---|
| EP | 0064379 A1 | 11/1982 |
| EP | 0568345 A1 | 11/1993 |
| EP | 0778304 | 6/1997 |
| EP | 1348451 A1 | 10/2003 |
| EP | 1430916 A1 | 6/2004 |
| EP | 1629835 A1 | 3/2006 |
| GB | 2160100 A | 12/1985 |
| GB | 2161819 A | 1/1986 |
| JP | 62042918 A | 2/1987 |
| JP | 3123730 A | 5/1991 |
| RU | 2092161 | 10/1997 |
| TW | 096141574 | 5/2008 |
| WO | WO 92/13901 | 8/1992 |
| WO | WO 94/07940 A1 | 4/1994 |
| WO | WO 96/18417 A1 | 6/1996 |
| WO | WO 98/11166 | 3/1998 |
| WO | WO 99/36058 | 7/1999 |
| WO | WO 99/47543 A2 | 9/1999 |
| WO | WO 99/56731 | 11/1999 |
| WO | WO 01/19333 | 3/2001 |
| WO | WO 91/04015 A1 | 4/2001 |
| WO | WO 01/54671 A | 8/2001 |
| WO | WO 01/87276 | 11/2001 |
| WO | WO 02/45685 A2 | 6/2002 |
| WO | WO 03/022323 A1 | 3/2003 |
| WO | WO 03/028653 | 4/2003 |
| WO | WO 03/033027 | 4/2003 |
| WO | WO 2004/024779 | 3/2004 |
| WO | WO 2004/026912 | 4/2004 |
| WO | WO 2004/052339 | 6/2004 |
| WO | WO 2005/051358 A1 | 6/2005 |
| WO | WO 2005/084639 | 9/2005 |
| WO | WO 2006/039152 | 4/2006 |
| WO | WO 2006/128471 A2 | 12/2006 |
| WO | WO 2008/066657 | 11/2007 |
| WO | PCT 07/023226 | 6/2008 |
| WO | WO2008/066657 A2 | 6/2008 |
| WO | WO 2008/070118 | 6/2008 |

OTHER PUBLICATIONS

Brannon-Peppas, L., "Polymers in Controlled Drug Delivery", Medical Plastics and Biomaterials, p. 34, Nov. 1997.

Birnbaum, D., et al., "Microparticle Drug Delivery Systems" Drug Delivery Systems in Cancer Therapy, Chapter 6, pp. 117-135; Sep. 2003.

Du, J., et al., "pH Sensitive Vesicles Based on a Biocompatible Zwitterionic Diblock Copolymer", Journal of American Chemistry Society, vol. 127, #51, pp. 17982-17983; 2005.

Kaneko, T.; Miyazaki, T.; Yamaoka, K.; Katayama, Y.; Matsuda, A.; Gong, J.; and Osada, Y.; "Shape-Memory Gels with Multi-Stimuli Responses"; Proceedings of SPIE, vol. 3669, pp. 199-208, Smart Structures and Materials; May 1999: Electroactive Polymer Actuators and Devices.

Wei, J-S.; Zeng, H-B.; Liu, S-Q.; Wang, X-G.; Tay, E.H.; and Yang, Y-Y.; Temperature and pH Sensitive Core-Shell Nanoparticles Self-Assembled From Poly(N-Isopropylacrylamide-Co-Acrylic Acid-CO-Cholesteryl Acrylate) for Intracellular Delivery of Anticancer Drugs; Sep. 2005; Frontiers in Bioscience 10, pp. 3058-3067; Frontier in Bioscience, U.S.A.

NG, C.C.; Cheng, Y-L.; Saville, B.A.; Thermoresponsive Polymer Membrane for the Local Delivery of Drugs; Summer 2001; Journal of Sexual and Reproductive Medicine, vol. 1 #1, pp. 21-27; Pulses Group Inc., Canada.

Luppi, B.; Cerchiara, T.; Bigucci, F.; Orienti, I.; and Zecchi, V.; pH-Sensitive Polymeric Physical-Mixture for Possible Site-Specific Delivery of Ibuprofen; Mar. 2003; European Journal of Pharmaceutics and Biopharmaceutics, 55, #2, pp. 199-202; Elsevier, Netherlands.

Bulmus, V.; Woodward, M.; Lin, L.; Murthy, N.; Stayton, P.; and Hoffman, A.; A New pH Responsive and Glutathione-Reactive, Endosomal Membrane Disruptive Polymeric Carrier for Intracellular Delivery of Biomolecular Drugs; Dec. 2003; Journal of Controlled Release, vol. 93, #2, pp. 105-120; Elsevier, Netherlands.

K.M. Scholsky and R.M. Fitch; Controlled Release of Pendant Bioactive Materials from Acrylic Polymer Colloids; 1986; Journal of Controlled Release, vol. 3, #1-4, pp. 87-102; Elsevier, Netherlands.

LaVan, D.A.; McGuire, T.; and Langer, R.; Small Scale Systems for In Vivo Drug Delivery; Oct. 2003; Nature Biotechnology, vol. 21, #10, pp. 1184-1191; Nature Publishing Group., U.K.

Schmidt, E.E.; Mohr, J.; and Stewart, R.F.; Side Chain Crystallizable Polymer Based Drug Delivery Phenomenon; 1991; in Proceedings of the 18th International Symposium on Controlled Release of Bioactive Materials, p. 134-135; Controlled Release Society, U.S.A.

Torchilin, V., "Structure and Design of Polymeric Surfactant-Based Drug Delivery Systems", Journal of Controlled Release, vol. 73, #2-3, pp. 137-172; Jun. 2001.

Boudreaux, CJ., et al., "Controlled Activity Polymers. XI Hydrolytic Release Studies of Hydrophilic Copolymers With Labile Esters of Model Allelopathic Phenols", Journal of Controlled Release, vol. 44, #2-3, pp. 185-194, Feb. 1997.

Loth, H., et al. "Methoxy-Polyethoxy Side-Chain Silastomers as Materials Controlling Drug Delivery by Diffusion Flux", Journal of Controlled Release, vol. 54, #3, pp. 273-282 Aug. 1998.

Yadav, S.K., et al., "Release Rates From Semi-Crystalline Polymer Microcapsules Formed by Interfacial Polycondensation", Journal of Membrane Science, vol. 125, #2, pp. 213-218; Mar. 1997.

Greene, L., "Side-Chain Crystallizable Polymers for Temperature-Activated Controlled Release", Polymeric Delivery Systems: Properties and Applications (ACS Symposium Series, No. 520), pp. 244-256, 1993.

Yu, L., et al., "A Subtle End-Group Effect on Macroscopic Physical Gelation of Triblock Copolymer Aqueous Solutions", Angew. Chem. Int. Ed. 2006, 45, 2232-2235.

Abayashinghe, N., et al., "Oligoethylene-End-Capped-Polylactides", Journal of Polymer Science: Part A: Polymer Chemistry, vol. 43, 5257-5266 (2005).

Mehvar, R., "Modulation of the Pharmacokinetics and Pharmacodynamics of Proteins by Polyethylene Glycol Conjugation", J. Pharm. Pharmaceut. Sci. 3(1):125-136, 2000.

Jiang, X., et al., ""Clickable" Polyglycolides: Tunable Synthons for Thermoresponsive, Degradable Polymers", Macromolecules, 41, 2008.

Baker, G., et al., "New Polylactides from Hydroxyacids Derived from Renewable Sources". Polymer Preprints 2007, 48(2), 826.

Maruyama, S., et al., "A Synthetic Polymer, Poly(2-methacryloyloxyethyl phosphorylcholine-co-$n$-stearyl methacrylate), Stimulates Insulin Release form RINm5F Insulinoma Cells", Biosci. Biotechnol. Biochem., 68 (10), 2197-2200, 2004.

Pollino, J., et al., "Non-Covalent Side-Chain Polymers: Design Principles, Functionalization Strategies and Perspectives", Chem. Soc. Rev., 2005, 34, 193-207.

Roberts, M., et al., "Molecule Engineering Including Advanced PEGylation: Understanding the Full Potential", The Drug Delivery Companies Report Spring/Summer 2003, PharmaVentures,Ltd, 2003.

Ivan, B., et al., "New Nanophase Separated Intelligent Amphiphilic Conetworks and Gels", Macromolecular Symposia, Jul. 2005 vol. 227(1), pp. 265-274, Wiley-VCH GmbH & Co. KgaA, Weinheim.

Shang, S., et al., "Comb-Like Ionomeric Copolymer: Itaconic Anhydride-co-Stearyl Methacrylate", ACS Polymer Preprints, 2007, vol. 48(2), pp. 871-872.

Davaran, S., et al, "Release of 5-Aminosalicylic Acid from Acrylic Type Polymeric Prodrugs Designed for Colon Drug Delivery", 1999; Journal of Controlled Release, 58, #3, pp. 279-287.

Bendix, Dieter, "Chemical Synthesis of Polyactide and its Copolymers for Medical Applications" 1998, Polymer Degradation and Stability, vol. 59,pp. 129-135; Elsevier Science Limited.

Menta, Nozer M., "Oral Delivery and Recombinant Production of Peptide Hormones. Part I: Making Oral Delivery Possible" Jun. 2004 Biopharm International pp. 1-6.

Mehta, Nozer M., "Oral Delivery and Recombinant Production of Peptide Hormones. Part II: Recombinant Production of Therapeutic Peptides" Jul. 2004 BIOPHARM International pp. 7-9.

Morgan, V., "NOBEX: No Barriers" Overview. No date. File created Jun. 14, 2006; Nobex Corporation, Research Triangle Park, NC; 2 pp.

Quintana, A., et al., "Design and Function of a Dendrimer-Based Therapeutic Nanodevice Targeted to Tumor Cells Through the Folate Receptor" Pharmaceutical Research, vol. 19, #9, pp. 1310-1316; Sep. 2002.

Henry, C., "Cooking Cancer—Carbon Nanotubes and Near-Infrared Radiation Kill Cancer Cells by Heating" Chemical & Engineering News, vol. 83, #32, p. 16; 2005.

Yan, X., et al., "Cisplatin Delivery from Poly(acrylic acid-co-methyl methacrylate) Microparticles", Journal of Controlled Release, vol. 106, #1-2, pp. 198-208; Aug. 2005.

Nishino, S., et al. "Preparation and Interfacial Properties of a Novel Biodegradable Polymer Surfactant: Poly(ethylene oxide monoolcate-block-DL-lactide)", Macromolecular Bioscience; vol. 5, pp. 1066-1073; 2005.

Anon. "Biodegradable Polymers: A Review" Environment and Plastics Industry Council (EPIC) Technical Report pp. 1-11; Nov. 24, 2000.

Anon. "What Are the Latest Drug Delivery Systems Made of?" Online Publication Science Scotland; The Royal Society of Edinburgh; Issue 2, pp. 9-10; Spring 2004.

Hadlington, S. "Special Delivery", "Chemistry World" (online edition, previously "Chemistry in Britain"), Royal Society of Chemistry, UK; No. 5, pp. 1-3; May 2003.

U.S. Appl. No. 60/856,430, filed May 3, 2008, Schmitt.
U.S. Appl. No. 60/857,546, filed May 8, 2008, Schmitt.
U.S. Appl. No. 60/857,755, filed May 8, 2008, Krumme.
U.S. Appl. No. 60/964,066, filed Feb. 8, 2009, Krumee.
U.S. Appl. No. 60/993,541, filed Mar. 12, 2009, Krumme.
U.S. Appl. No. 61/016,223, filed Jun. 21, 2009, Krumme.
Written Opinion mailed Jun. 8 2010, on PCT/US 2008/013335.

* cited by examiner

US 8,524,259 B2

SYSTEMS AND METHODS FOR DELIVERY OF MATERIALS

CROSS-REFERENCE TO RELATED APPLICATIONS

This application is related to U.S. application Ser. No. 11/999,415, filed Dec. 4, 2007, which claims priority from and the benefit of U.S. provisional Application No. 60/873,234, filed Dec. 5, 2006.

This application is also related to
(1) International Patent Application PCT/US2007/024909, which was (i) filed Dec. 4, 2007, claiming priority from US Provisional Application 60/873,234 filed Dec. 5, 2006, and (ii) published as WO/2008/070118 on Jun. 12, 2008,
(2) International Patent Application PCT/US2007/025032, which was (i) filed Dec. 4, 2007, claiming priority from U.S. Provisional Application 60/873,234 filed Dec. 5, 2006, and (ii) published as WO/2008/070165 on Jun. 12, 2008,
(3) U.S. application Ser. No. 12/284,755, filed Sep. 25, 2008, which is a continuation of U.S. Application No. 11/999,415, and which claims priority from U.S. provisional Application Nos. 61/005,400, filed Dec. 4, 2007, 61/131,123, filed Jun. 4, 2008, and 61/131,716, filed Jun. 10, 2008, and
(4) U.S. application Ser. No. 12/287,520 filed Oct. 10, 2008, which claims priority from U.S. provisional Application Nos. 61/005,400, filed Dec. 4, 2007, 61/131,123, filed Jun. 4, 2008, and 61/131,716, filed Jun. 10, 2008.

Those International patent applications disclose the use of certain polymers (referred to therein as crystalline side chain or CYSC polymers) for the delivery of drugs. The entire disclosure of each of the applications and publications identified above is incorporated by reference herein for all purposes.

This specification incorporates by reference all documents referred to herein and all documents filed concurrently with this specification or filed previously in connection with this application, including but not limited to such documents which are open to public inspection with this specification.

FIELD OF THE INVENTION

This invention relates to systems for the delivery of bioactive and other materials, and for other purposes.

BACKGROUND

There are many known polymeric systems for the delivery of drugs and other materials. A continuing problem is obtaining a desired loading and delivery profile at a desired location and at a desired time.

SUMMARY OF THE INVENTION

This invention provides novel compositions and methods which are useful for the delivery of bioactive and/or other materials. The delivery is effected by associating the material to be delivered with (i) certain polymers which comprise repeating units containing crystalline moieties and/or terminal units comprising crystalline moieties (those polymers being referred to herein as CYC polymers), and/or (ii) certain non-polymeric compounds which contain crystalline moieties (those compounds being referred to herein as CYC compounds), and/or (iii) certain "self-assemblies" which contain crystalline moieties (those assemblies being referred to herein as CYC assemblies). The CYC polymers, CYC compounds and CYC assemblies are collectively referred to herein as "CYC carriers".

This invention also provides novel CYC polymers and CYC assemblies. The novel CYC polymers include, but are not limited to, (i) a sub-class of CYC polymers, referred to herein as SSP polymers, and (ii) other CYC polymers. These novel polymers are not only useful for delivery of bioactive and/or other materials but also in other applications. Definitions of CYC polymers, CYC compounds, CYC assemblies and SSP polymers are given below. Where the disclosure below refers to one of the CYC carriers, a component of one of the CYC carriers, a characteristic of one of CYC carriers, or to a composition or method making use of one of the CYC carriers, that disclosure is also applicable to other CYC carriers, unless the context makes this impossible. The materials that can be delivered in accordance with the invention (which are referred to herein as "release materials") include, but are not limited to, bioactive materials, including but not limited to drugs. Thus, where reference is made herein to the delivery of bioactive materials, it is to be understood that such references are also applicable to other materials.

The sites to which the materials can be delivered (which are referred to herein as "target sites") can be of any kind, and include, but are not limited to, the sites disclosed in the International Applications identified above. For example, the target site can be any animal, vegetable or mineral substrate, part or all of which is affected (e.g. is improved, preserved, identified or damaged, in some cases producing a physiological effect), by delivery of the material to it. The target site can for example comprise a living animal, e.g. an internal or external part of a human being; a cell; a fibrous material, e.g. human hair or a fabric; soil; a seed; a fruit; or a vegetable.

The term "CYC polymer" is defined herein as a polymer which:
(A) comprises polymeric molecules having a backbone and comprising at least one moiety which
  (i) has the formula -b-Cy, and
  (ii) either
    (A) forms part of a repeating unit of the backbone, the repeating unit having formula (1) below

(1)

where $Y_{ch}$ is a moiety forming part of the backbone,
b is a bond or moiety which links the Cy moiety to $Y_{ch}$, and
Cy is a moiety which is associated with other moieties (which may also be Cy moieties) to provide the CYC polymer with crystallinity;
or
    (B) forms part of a terminal unit of the backbone, the terminal unit having formula (2) below

(2)

where $Y_{term}$ is a moiety at the end of the backbone, and b and Cy are as defined in formula (1); and
(B) has a crystalline melting temperature (hereinafter abbreviated to Tp) of at least 0° C. and a heat of fusion (hereinafter abbreviated to ΔH) of at least 3 J/g which result from association of the Cy moieties. In this definition, and throughout this specification, Tp and ΔH are measured on a differential scanning calorimeter (DSC) as hereinafter described.

In many CYC polymers, the backbone of the polymeric molecules comprises repeating units having formula (3) below

(3)

where Z is a moiety forming part of the backbone and Rz represents a moiety which does not comprise a Cy moiety. Many useful CYC polymers have an amphiphilic character, with the Cy moieties providing hydrophobic characteristics and the Z(Rz) moieties providing hydrophilic characteristics.

The term "CYSC polymer" is used herein to denote a CYC polymer in which at least a majority by weight, preferably at least 90% by weight, particularly substantially all, of the Cy moieties are present in repeating units of formula (1). Thus, a CYSC polymer always contains repeating units of formula (1), and optionally contains terminal units of formula (2) and repeating units of formula (3). The term "ECC polymer" is used herein to denote a CYC polymer in which at least a majority by weight, preferably at least 90% by weight, particularly substantially all, of the Cy moieties are present in terminal units of formula (2). Thus, an ECC polymer always contains terminal units of formula (2) and repeating units of formula (3), and optionally contains repeating units of formula (1).

The term "CYC compound" is defined herein as a non-polymeric compound which (A) has the formula $$Q(-b-Cy)_q \quad (4)$$

wherein q is least 2, e.g. 3-8,

Q is a moiety having a valence of at least q, b is a bond or a moiety linking the Cy moiety to the Q moiety, and Cy is as defined in formula (1), and (B) has a crystalline melting temperature, Tp, of at least 0° C. and a ΔH of at least 3 J/g which results from association of the Cy moieties.

The term "CYC assembly" is defined herein as an assembly of (i) a polymer which is a CYC polymer as defined above except that the polymer does not necessarily have a Tp of at least 0° C. and a ΔH of at least 4 J/g, and (ii) a compound which contains a Cy moiety and which is intimately mixed with the polymer but is not covalently linked to the polymer, the assembly having a crystalline melting temperature, Tp, of at least 0° C. and a ΔH of at least 3 J/g which results from association of the Cy moieties.

The term SSP polymer is defined herein as a polymer which (1) has a crystalline melting temperature, Tp, of at least 25° C., e.g. 27-100° C., and a ΔH of at least 5 J/g; and (2) comprises polymeric molecules having a backbone which comprises (a) repeating units which do not contain hydrophilic moieties, and have the formula (1) below,

(1)

where $Y_{ch}$ is a moiety forming part of the backbone,
b is a bond or a moiety linking the Cy moiety to $Y_{ch}$, and
Cy is a moiety is associated with other Cy moieties to provide the SSP polymer with crystallinity;

(b) repeating units which have the formula (2zphil) below,

(2zphil)

where Z is a moiety forming part of the backbone, and Rzphil comprises a hydrophilic moiety;

the molar ratio of the units of formula (2zphil) to the units of formula (1) being at least 2.5:1.

The moiety -b-Cy is also referred to in this specification as an -Rc moiety, i.e. Rc is synonymous with b-Cy.

Various aspects of the invention include:—

(1) Compositions comprising (i) a CYC carrier, and (ii) a release material associated therewith. Such compositions are referred to herein as "release compositions".

(2) Methods of releasing release materials from compositions as defined in (1).

(3) Methods in which (i) a CYC carrier and (ii) a release material are used in association to affect (e.g. improve, preserve, identify or damage) a target site, e.g. to affect the health or appearance of an organism, or to assist in the diagnosis of an organism.

(4) Methods of affecting a target site which comprise administering to a target site (i) a CYC carrier and (ii) a release material, the CYC carrier and the release material being associated with each other before administration or becoming associated with each other during or after administration.

(5) Methods of making a release composition as defined in (1). The composition is often made before the composition is administered, but can be made or modified during administration and/or in situ at the administration site as a result of simultaneous or sequential administration of CYC carrier and the release material.

(6) Devices for administering (i) a CYC carrier and (ii) a release material, the CYC carrier and the release material being (i) in the form of a composition as defined in (1) or (ii) separately administered and becoming associated during or after administration. Such devices are referred to herein as "release devices".

(7) The use of a release composition or release device as defined above.

(8) Methods of making release devices and release compositions as defined above.

(9) Use of a composition comprising (i) a CYC carrier and (ii) a drug associated therewith in the manufacture of a medicament for the treatment of a condition in an organism.

(10) Novel CYC carriers suitable for use in paragraphs (1)-(9) above and for other purposes, for example the SSP polymers.

BRIEF DESCRIPTION OF THE DRAWINGS

The invention is illustrated in the accompanying drawings in which the Figures summarize results obtained in the Examples, as further described below. In each of the Figures, unless otherwise noted, the vertical axis shows the total percentage release ("cumulative release") of the release material, the horizontal axis shows the time in days, and the different curves are identified by reference to the polymer or sample ID #marked on the Figure.

In FIG. 16, Tp is shown on the vertical axis. In FIG. 17, ΔH is shown on the vertical axis. In both Figures, the weight % of one of the polymers (ID #326-1-1 of 3 to 7-42-11) is shown on the horizontal axis. Each of the mixtures has a single Tp indicating co-crystallization through self-assembly; and the ΔH of the mixtures is higher than the theoretical value.

DETAILED DESCRIPTION OF THE INVENTION

Figure 1A:
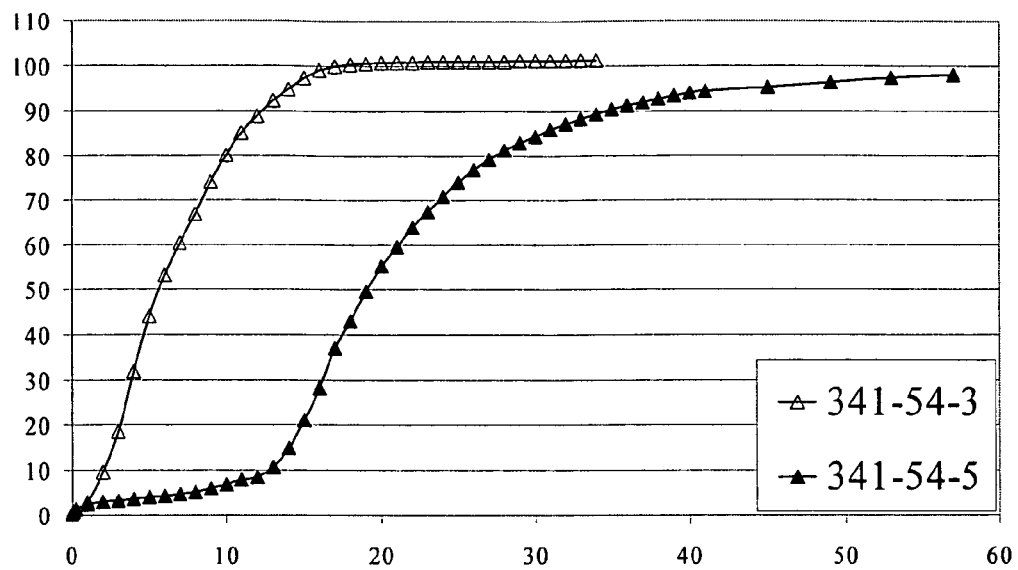
FIG. 1a shows, on the vertical axis, the cumulative release of risperidone from test sample ID #341-54-3 based on the unmodified PLGA polymer ID #341-1-0 prepared in Example EC1(C); and test sample ID #341-54-5, based on polymer ID #341-1-3 prepared in Example EC 1, and, on the horizontal axis, the time in days.

In this specification:—
(1) Reference is made to particular features of the invention (including for example components, ingredients, elements, devices, apparatus, systems, groups, ranges, method steps, test results, etc). It is to be understood that the disclosure of the invention in this specification includes all possible combinations of such particular features. For example, where a particular feature is disclosed in the context of a particular embodiment or claim, that feature can also be used, to the extent appropriate, in the context of other particular embodiments and claims, and in the invention generally.
(2) The singular forms "a", "an", and "the" include plural reference unless the context clearly dictates otherwise. Thus, for example, a reference to "a part" includes a plurality of such parts.
(3) The term "comprises" and grammatical equivalents thereof are used to mean that, in addition to the features specifically identified, other features are optionally present. For example a formulation which comprises a CYC carrier and a drug can contain a single CYC carrier and a single drug, or two or more CYC carriers and/or two or more drugs, and optionally contains one or more other ingredients which are not CYC carriers, for example other ingredients as disclosed herein.
(4) The term "consisting essentially of" and grammatical equivalents thereof are used to mean that, in addition to the features specifically identified, other features may be present which do not materially alter the disclosed and/or claimed invention.
(5) The term "at least" followed by a number is used to denote the start of a range beginning with that number (which may be a range having an upper limit or no upper limit, depending on the variable being defined). For example "at least 1" means 1 or more than 1, and "at least 80%" means 80% or more than 80%.
(6) The term "at most" followed by a number is used to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.
(7) A range written as "(a first number) to (a second number)" or "(a first number)-(a second number)" means a range whose lower limit is the first number and whose upper limit is the second number. For example, "from 8 to 20 carbon atoms" or "8-20 carbon atoms" means a range whose lower limit is 8 carbon atoms, and whose upper limit is 20 carbon atoms.

(8) The terms "plural", "multiple", "plurality" and "multiplicity" are used herein to denote two or more than two features.

(9) When a method is described as comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility).

(10) When reference is made to two or more features, this includes the possibility that the two or more features are replaced by a lesser number or greater number of features providing the same function (except where the context excludes that possibility).

(11) The numbers given should be construed with the latitude appropriate to their context and expression; for example, each number is subject to variation which depends on the accuracy with which it can be measured by methods conventionally used by those skilled in the art.

(12) Parts, ratios and percentages are by weight, except where otherwise noted.

(13) Temperatures are in degrees Centigrade (° C.).

(14) Molecular weights of polymers are in Daltons; are number average molecular weights (Mn) unless stated to be weight average molecular weights (Mw); and are measured by gel permeation chromatography (GPC) with a light scattering detection method, for example using a DAWN DSP laser photometer from Wyatt Technology, unless stated to be measured using GPC against a polystyrene standard.

(15) The terms "melting point" (often abbreviated to Tp), "onset of melting temperature" (often abbreviated to To) and "heat of fusion" (which is a measure of crystallinity of the polymer, is expressed in J/g and is often abbreviated to ΔH) are well known to polymer technologists and refer to quantities determined using a differential scanning calorimeter (hereinafter DSC), e.g. a Q 100 DSC from TA Instruments, at a rate of temperature change of 10° C./min, e.g. from —10 to 150° C. Tp is the peak melting temperature, To is the temperature at the intersection of the baseline of the DSC peak and the onset line, the onset line being defined as the tangent to the steepest part of the DSC curve below Tp, and ΔH is the heat of fusion associated with the endotherm or exotherm as calculated by the DSC and is reported in J/g. Unless otherwise stated, the values of Tp, To and ΔH are measured on the second heat cycle.

(16) Bulk viscosities are given in centipoise and are measured using a Brookfield LVT viscometer with an electronically thermostat controlled thermal heater, controlled for example to 95° C., and small sample adapter using spindles 4 and 7.

(17) Solubility parameters are calculated using the method described in D. W. van Krevelen, "Properties of Polymers" Elsevier, 1997, p. 200-214 especially p. 214 and reported in $J^{1/2}/cm^{3/2}$.

(18) The term "associated" and grammatical variations thereof include any type of interaction, including chemical bonds (for example, covalent, ionic and hydrogen bonds) and/or Van der Waals forces, and/or polar and non-polar interactions through other physical constraints provided by molecular structure, and interactions through physical mixing.

(19) The term "pharmaceutical formulation" means a composition which (i) is suitable for administration to a human being or other mammal or which can be treated, e.g. sterilized, to make it suitable for such administration, and (ii) comprises at least one drug and at least one CYC carrier. The term "drug" means a material which is biologically active in a human being or other mammal, locally and/or systemically.

(20) The term "therapeutically effective amount" or "therapeutically effective dosage" means an amount of a drug which results in a desired therapeutic effect.

(21) The term "agricultural" refers to compositions and methods which are useful in the treatment of plants, seeds and soil. The term "aquacultural" refers to compositions and methods which are useful in the treatment of fresh water or salt water organisms.

(22) The term "Personal Care" refers to compositions and methods which are useful in the treatment of the human body (including human hair) primarily or exclusively for non-medical purposes, for example for cosmetic or hygienic purposes.

(23) The term "organism" includes, but is not limited to, human beings and other mammals, living tissue which is not part of a mammal, freshwater organisms, saltwater organisms, plants, seeds, and soil which contains living organisms. The invention is useful, for example, for delivering drugs to human beings and other mammals; for delivering biocides and/or fertilizers to plants, seeds and soil; for delivering cosmetic ingredients to human beings; and for use as components in cosmetic and other formulations to provide benefits such as thickening and control of rheological properties.

(24) The term "therapeutically effective amount" means an amount of a drug which produces a desired therapeutic effect.

(25) The term "diagnostic agent" means any chemical moiety that can be used for diagnosis or in a diagnostic test. For example, diagnostic agents include imaging agents containing radioisotopes, contrasting agents containing for example iodine, enzymes, fluorescent substances and the like.

(26) The term "treatment" means administration of a composition to a site, e.g the administration of a pharmaceutical formulation to an individual in order to alter a physiological state, whether or not the process includes a curative element.

(27) "Controlled release" of a drug or other bioactive material means release of the material in a pre-determined or adjustable way such that the amount or rate or timing of release is pre-set or is altered in a desired way.

(28) The terms "controlled release device", "controlled release dosage form" and similar terms mean any formulation or device wherein the release rate (e.g., rate of timing of release) of a drug or other desired substance contained therein is controlled by the device or dosage form itself and/or by the environment of use. Controlled drug delivery includes delivery of an amount of drug to a particular target site at a particular time, for example delivery of a bolus of drug to a tumor site.

(29) "Sustained release" of a drug or other material means release over an extended period of time, for example minutes, hours or days, such that less than all the bioactive material is released initially. A sustained release rate may provide, for example, a release of a specified amount of a drug from a pharmaceutical formulation, over a certain time period, under physiological conditions or in an in vitro test.
(30) "Bolus" release means release of a large dose, for example substantially all of a drug at one time or over a short period of time. Bolus release can be preceded or followed by sustained release.
(31) The term "burst effect" is used, often in the context of drug delivery, to mean release of a bioactive material from a composition in an amount or at a rate which is higher than is desired (typically, in drug delivery, higher than the therapeutic window). A burst is generally followed by a rapidly decreasing rate of release. A burst effect may be defined as the release of more than a defined threshold proportion of the bioactive material over a defined time under defined conditions. The defined conditions can for example be physiological conditions (e.g. gastrointestinally for a pill or subcutaneously for an implant) or the conditions in a suitable in vitro test (for example in phosphate-buffered saline at about 20° C. or about 37° C., or a test as described in the Examples below). The threshold proportion can for example be 20%, 30%, 40%, 50%, 60%, 70%, 80%, 90%, or 95%, and the defined time can for example be 30 minutes, 1 hour, 2 hours, 3 hours, 6 hours, 8 hours, 10 hours, 12 hours, 16 hours, 20 hours, 24 hours, 36 hours, or 48 hours. For example, a pharmaceutical formulation which does not display a significant burst effect may be one which releases less than 10% of the drug over a 3 hour period after administration, or over a 24-hour period after administration.
(32) The term "functionalized", as applied to a chemical compound, including a polymer, means that the compound has been treated so that it contains a functional moiety (i.e. a moiety which will undergo a further desired chemical reaction) which was not present on the compound before the treatment, or so that the polarity of the compound is changed, as evidenced, for example, by a change in the solubility parameter.
(33) The term "alkyl" includes alkyl moieties which are straight chain alkyl moieties, branched chain alkyl moieties, cycloalkyl moieties, and moieties which consist essentially of two or more of straight chain alkyl, branched chain alkyl and cycloalkyl moieties.
(34) The term "bioerodable" (sometimes alternatively "biodegradable") as applied to a CYC carrier or to a release composition means that the carrier or composition, when placed in the human body, is eliminated from the human body, the carrier being eliminated without change or as one or more lower molecular weight products resulting from the degradation of the carrier in the human body. The elimination may take place relatively rapidly, e.g. in a period of up to 10 weeks, but is more often longer, for example over a period of up to 1 year or longer, e.g. up to 3 years. Carriers that are not bioerodable may leave the body by voiding if part of an oral formulation, or by explanation if part of an implanted formulation.
(35) Some of the structural formulas given below for CYC polymers show the repeating units in the general form

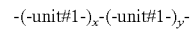

This representation is used to denote polymers in which the different repeating units are distributed randomly and/or are distributed in blocks containing only one of the repeating units. Thus, the polymers represented by these formulas can be either random copolymers or block copolymers.

The tables below sets out other abbreviations used in this specification, and the meanings to be attributed to them.

| Abbreviation | Meaning |
|---|---|
| Cx | a linear moiety containing x carbon atoms |
| CxAcid | An acid of formula Cx-1.COOH, e.g. C22Acid is behenic acid. |
| CxOH | An alcohol of formula CxOH, e.g. C22OH is behenyl alcohol. |
| CxA | an n-alkyl acrylate in which the n-alkyl group contains x carbon atoms, e.g. C16A is hexadecyl acrylate. |
| CxMA | an n-alkyl methacrylate in which the n-alkyl group contains x carbon atoms, e.g. C16MA is hexadecyl methacrylate. |
| (meth)acrylate | an acrylate or methacrylate |
| (meth)acrylic acid | acrylic acid or methacrylic acid |
| AA | acrylic acid |
| MA | methacrylic acid |
| GA | glycolic acid |
| HEA | 2-hydroxyethyl acrylate |
| LA | lactic acid solution (85+%) |
| PLGA | Copolymer of GA and LA |
| PTSA | para toluene sulfonic acid |
| AcAm | acrylamide |
| SUCAN | succinic anhydride |
| SORB | sorbitol |
| MiBK | methyl isobutyl ketone |
| AIBN | azo bisisobutyronitrile |
| DCM | dichloromethane |
| TCM | trichloromethane (chloroform) |
| DMAEA | dimethylaminoethyl acrylate |
| DMAEMA | dimethylaminoethyl methacrylate |
| $PEG_6A$ | $CH_2=CH-CO-(OCH_2CH_2)_6-OCH_3$ |
| $PEG_6MA$ | $CH_2=C(CH_3)-CO-(OCH_2CH_2)_6-OCH_3$ |
| $PEG_9MA$ | $CH_2=C(CH_3)-CO-(OCH_2CH_2)_9-OCH_3$ |
| $PEG_{12}MA$ | $CH_2=C(CH_3)-CO-(OCH_2CH_2)_{12}-OCH_3$ |
| $PEG_{23}MA$ | $CH_2=C(CH_3)-CO-(OCH_2CH_2)_{23}-OCH_3$ |
| $PEG_{25}MA$ | $CH_2=C(CH_3)-CO-(OCH_2CH_2)_{25}-OCH_3$ |
| $PEG_{46}MA$ | $CH_2=C(CH_3)-CO-(OCH_2CH_2)_{46}-OCH_3$ |
| $PEG_{25}-OC_{22}MA$ | $CH_2=C(CH_3)-CO-(OCH_2CH_2)_{25}OC_{22}H_{45}$ |
| $PEG_6-OH\ A$ | $CH_2=CH-CO-(OCH_2CH_2)_6OH$ |

-continued

| Abbreviation | Meaning |
| --- | --- |
| PPG$_6$-OH A | CH$_2$=CH—CO—(OCH$_2$CH(CH$_3$))$_6$OH |
| 2-HEA | CH$_2$=CH—CO—OCH$_2$CH$_2$—OH |
| VP | vinyl pyrrolidone |
| 2-HEMA | CH$_2$=C(CH$_3$)—CO—OCH$_2$CH$_2$—OH |
| IPA | Isopropyl alcohol |
| EtAc | ethyl acetate |
| NMP | N-methyl pyrrolidone |
| MCR | monomethacryloxypropyl alkyl polydimethylsiloxane wherein the alkyl group contains 1-8 carbon atoms. sold by Gelest as MCR-M17 |
| BMP | butyl-3-mercapto propionate |
| Miglyol | Miglyol 812, a triglyceride with a mixture of C8 and C10 |
| Trigonox | Trigonox 428-t-butyl peroxy-3,5,5-trimethyl hexanoate |
| Dexa | Dexamethasone, which has a solubility parameter of 20.85, and which is (9-fluoro-11β,17,21-trihydroxy-16a-methylpregna-1,4-diene-3,20-dione) |
| Prav | Pravachol, which has a solubility parameter of 21.07, and which is (3,5-dihydroxy-7-[6-hydroxy-2-methyl-8-(2-methylbutanoyloxy)-1,2,6,7,8,8a-hexahydronaphthalen-1-yl]-heptanoic acid) |
| Risp | Risperidone, which has a solubility parameter of 17.48 and which is (4-[2-[4-(6-fluorobenzo[d]isoxazol-3-yl)-1-piperidyl]ethyl]-3-methyl-2,6-diazabicyclo[4.4.0]deca-1,3-dien-5-one) |
| Dcl | Diclofenac sodium, which has a solubility parameter of 23.4 and which is (2-[2-(2,6-dichlorophenyl)aminophenyl]ethanoic acid) |
| Tacro | Tacrolimus, which has a solubility parameter of 19.32, and which is (3S3R*[E(1S*,3S*,4S*)],4S*,5R*,8S*,9E,12R*,14R*,15S*,16R*,18S*,19S*,26aR*]]-5,6,8,11,12,13,14,15,16,17,18,19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c] [1,4] oxaazacyclotricosine-1,7,20,21(4H,23H)-tetrone, monohydrate) |
| FTIR | Fourier transform infrared spectroscopy |
| UV vis | Ultraviolet visible spectroscopy |
| Boc-protected | an amine group which has been reacted with di-tert--butyl dicarbonate so that it is no longer reactive. |

CYC Carriers

Crystallinity and Heat of Fusion of CYC Carriers

The crystallinity which is an essential part of the CYC carriers is provided by association of the Cy moieties with each other and/or with moieties in other materials (which moieties may also be Cy moieties). The Cy moieties comprise moieties which can overlap and interact with each other and/or other moieties to form crystalline aggregates or domains. Examples of such moieties include polymethylene moieties containing at least 13, preferably at least 15, particularly at least 17, and up to 50 or even more, methylene moieties, e.g. 15-23 or 17-21 methylene moieties. Many other examples of such moieties are disclosed below. The extent of the crystallinity depends upon the ability of such moieties to overlap and interact. Crystallinity is, therefore, increased by increasing the proportion of Cy moieties, by increasing the proximity of the Cy moieties to each other (for example by placing all or a large proportion of the Cy moieties in a block (e.g. a grafted block) of a copolymer, or in a terminal unit of a polymer or compound), and by minimizing other moieties which are bulky enough to interfere with the ability of the Cy moieties to overlap and interact. In the limited context of the polymers known as side chain crystalline (SCC) polymers, it is known to produce crystallinity by the interaction of polymethylene moieties and the like. Those skilled in the art will have no difficulty, having regard to the disclosure of this specification and their own knowledge, in making and using the crystalline CYC carriers which are useful in this invention. Patents and other publications relating to SCC polymers include J. Poly. Sci. 60, 19 (1962); J. Poly. Sci, (Polymer Chemistry) 7, 3053 (1969), 9, 1835, 3349, 3351, 3367, 10, 1657, 3347, 18, 2197, 19, 1871; J. Poly. Sci, Poly-Physics Ed 18 2197 (1980); J. Poly. Sci, Macromol. Rev, 8, 117 (1974); Macromolecules 12, 94 (1979), 13, 12, 15, 18, 2141, 19, 611; JAGS 75, 3326 (1953), 76; 6280; Polymer J 17, 991 (1985); and Poly. Sci USSR 21, 241 (1979); U.S. Pat. Nos. 4,830,855, 5,120,349, 5,129,180, 5,156,911, 5,254,354, 5,387,450, 5,412,035, 5,469,867, 5,665,822, 5,752,926, 5,783,302, 6,013,293, 6,060,540, 6,199,318, 6,210,724, 6,224,793, 6,255,367, 6,376,032, 6,492,462, 6,540,984, 6,548,132, 6,831,116, 6,989,417, and 7,101,928; and US Patent Application Publications Nos. 2001/0018484, 2002/0090425 and 2002/0127305. The entire disclosure of each of those publications, patents and patent publications is incorporated herein by reference for all purposes.

The value of the heat of fusion, ΔH, of a CYC carrier reflects the extent of its crystallinity, and is at least 3, for example at least 4, at least 10, at least 20, at least 25, at least 30, at least 35, at least 40, or at least 45, J/g., and may be for example 3-50, 4-50, 10-50, 10-40, 15-35, 3-30, 3-22, or 3-10, J/g.

The CYC carrier can, but does not need to, have so-called "main chain crystallinity", i.e. crystallinity resulting from crystallization of the polymer backbone. Thus, in some embodiments, the CYC carrier have main chain crystallinity, for example when a main chain crystalline polymer is modified to include b-Cy moieties at intermediate and/or terminal points. If the CYC carrier does have main chain crystallinity, Tp and ΔH should be assessed solely on the crystallinity provided by the Cy moieties, ignoring the Tp and ΔH resulting from the main chain crystallinity.

Tp, Melting Range (Tp-To) and Mn of CYC Carriers.

The melting point (Tp) of the CYC carriers is primarily dependent on the nature of the Cy moieties, and (unlike main chain crystalline polymers) is not highly dependent on the molecular weight of the carrier. The CYC carrier can for example have a Tp of 22-70, 35-50, 38-50, 37-42, or 40-47° C., or at least 37° C. However, CYC carriers with a Tp below 22° C., for example as low as 2° C., or higher than 70° C., may be useful in certain embodiments. The fact that the molecular weight can be controlled with relatively little change in Tp and Tp–To is important. It means that it is possible, by selection of the Cy moieties (and other moieties) in the CYC carrier, and the method used to prepare the CYC carrier (e.g. making use of chain transfer agents when preparing a polymer), to make a carrier which has a desired Tp, Tp–To and molecular weight. These measures can also be used to control the melting range of the CYC carriers. The melting range can conveniently be quantified by the value of Tp–To (To being the onset of melting temperature, as defined above). In some embodiments, the CYC carrier has a Tp–To<$Tp^{0.7}$, e.g. <$Tp^{0.6}$; for example, in this embodiment, if Tp is 40° C., Tp–To is less 13.2° C., e.g. less than 9.1° C. In other embodiments, Tp–To is less than 15° C., less than 10° C. or less than 5° C. The ability to control these variables is valuable for various purposes. For example, in the case of a pharmaceutical formulation, Tp can be selected with reference to in vivo temperatures. In addition, Tp and Tp–To can be selected to facilitate the preparation and processing of release compositions at relatively low temperatures, particularly when the release material would be degraded by higher temperatures.

Generally, the Tp of a CYC polymer increases as the number of linear carbon atoms in the Cy moieties increases. For example, the homopolymers of n-alkyl acrylates in which the n-alkyl group contains 14, 16, 18, 22, 30, 40 and 50 carbon atoms have Tps of about 20, 36, 49, 65, 76, 96 and 102° C. respectively; and the homopolymers of the corresponding n-alkyl methacrylates have Tps of about 10, 26, 39, 55, 68, 91 and 95° C. respectively. The Tp of a copolymer consisting of two or more —Y(b-Cy)- moieties reflects the relative proportions of the different moieties. Random copolymers of long chain n-alkyl acrylates and n-alkyl methacrylates generally have intermediate Tps in the range of 0 to 85° C. dependent on the length of the n-alkyl chain. The presence of other moieties (i.e. moieties which do not contain Rc moieties) generally reduces Tp and broadens the melting range. Random copolymers with other monomers, e.g. acrylic acid or butyl acrylate, typically have somewhat lower melting temperatures. Longer chain Rz moieties generally depress Tp more than shorter chain Rz moieties, because longer chain moieties have greater potential to disrupt the formation of crystalline domains by the Cy moieties.

The Mn of the CYC carrier can influence the incorporation and/or retention and/or delivery of a release material. Mn can for example be 500-1,000,000, e.g. 1,000-50,000, 2000-40,000, 2000-25,000, 2000-30,000, or 3000-20,000, or 3000-10,000, or 3000-8000. In some cases, it is less than 200,000, or less than 100,000, or less than 80,000, or less than 60,000, or less than 50,000, or less than 30,000, or less than 25,000, or less than 20,000, or less than 10,000, or less than 8000, or less than 7000, or less than 5000, or less than 2500, or less than 1000, e.g. 1,000-20,000, or 1,000-10,000 or 2,000-20,000, or 3,000-5,000. In other cases, it may be greater than 1,000,000. In yet other cases, e.g. when the CYC polymer is a cross-linked hydrogel, it may be infinite. In some embodiments, the CYC carrier has a molecular weight less than 20,000, or less than 15,000 or less than 10,000. In some embodiments, Mn is greater than 600, or greater than 800, or greater than 1000. In some embodiments, the CYC carrier is not charged or crosslinked, so that it can be voided from the body.

In some embodiments, when the composition is a pharmaceutical formulation which is to be administered orally, the CYC carrier preferably has an Mn high enough to limit or avoid absorption of the CYC polymer across the intestinal wall, and/or is charged or crosslinked, and/or is insoluble under physiological conditions. This eliminates, or significantly reduce transportation of the polymer across the gut wall. The CYC carrier, after having released the drug, will be passed through the GI tract and be voided.

The CYC carriers are preferably substantially physiologically inactive. Some are bioerodable. Others are non-absorbable or essentially non-absorbable in a patient's body. The CYC polymers of high molecular weight, e.g. Mn greater than 10,000, and charged or crosslinked polymers, or polymers which are insoluble under physiological conditions, eliminate or significantly reduce transportation of the polymer across a cell membrane or gut wall.

Different Types of CYC Polymer

The CYC polymer can be a homopolymer or a copolymer. If it is a copolymer, it can be a random copolymer, a graft copolymer or a block copolymer (including a thermoplastic elastomer), or a core shell polymer. For example, the polymer can (a) comprise one or more types of —Y(Rc)- moiety and one or more types of —Z(Rz)- moiety, all the moieties being randomly distributed;

(b) be a block copolymer comprising (i) polymer blocks consisting essentially of one or more —Z(Rz)- moieties, and (ii) polymer blocks which comprise one or more types of repeating unit of the formula —Y(Rc)-, and optionally one or more types of repeating units of the formula —Z(Rz)-; or (c) be a graft polymer, for example (i) a polymer comprising a backbone which comprises, or consists essentially of, one or more —Y(Rc)- moieties, and grafted side chains each of which comprises, or consists essentially of, one or more —Z(Rz)- moieties, or (ii) a polymer comprising a backbone which comprises, or consists essentially of, one or more —Z(Rz)- moieties, and grafted side chains each of which comprises, or consists essentially of, one or more -Y(Rc)- moieties.

In some embodiments, it is preferred to use a CYC carrier which is bioerodable (as defined above).

It is generally preferable that the CYC carrier be substantially physiologically inactive.

Y and Z Moieties

The backbone of a CYC polymer can be of any kind. The —Y— moieties (which will be present in a CYSC polymer and will optionally be present in an ECC polymer) and the —Z— moieties (which will be present in an ECC polymer and will optionally be present in a CYSC polymer) can be the same as, or different from, each other. The —Y— moieties and/or the —Z— moieties can for example comprise carbon atoms which are linked to each other directly by covalent bonds or through other elements or combinations of elements, and repeating units can be linked to each other directly by covalent bonds or can contain linking units comprising one or more atoms, e.g ester (including orthoester), amide, ether or phosphate linkages. For example, the CYC polymer can consist essentially of, or can comprise, sections which consist essentially of, polyacrylates, poly-alkyl acrylates, poly-fluoroacrylates, polymethacrylates, polyalkyl methacrylates, poly-N-alkyl methacrylamides, poly-alkyl oxazolines, poly-alkyl vinyl ethers, poly-alkyl 1,2-epoxides, poly-alkyl glycidyl ethers, poly-vinyl esters, poly-acrylamides, poly-methacrylamides, poly-maleimides, poly-α-olefins, poly-p-alkyl styrenes, poly-alkyl vinyl ethers, polyolefins, polyethers, polyurethanes, polysilanes, polysiloxanes, or poly(alkyl phosphazenes). CYSC polymers can for example be obtained directly by addition polymerization of suitable monomers, e.g. acrylic, methacrylic, olefinic, epoxy, esters, amides, vinyl or silicon-containing monomers. ECC polymers can for example be obtained by modification of the terminal units of polyesters obtained for example by the polymerization of monomers such as glycolic acid and lactic acid. Further details of CYC polymers and methods for preparing CYC polymers are given below.

In some embodiments, the backbone of a CYC polymer includes a plurality of bioerodable linkages. In such CYC polymers, a plurality of the —Y— moieties and/or the —Z— moieties can for example have the formula $$-D_{nd}-Q-E_{ne}- \quad (Q1)$$

where Q is —O—, —NH— or —S—,
nd is 0 or 1,
ne is 0 or 1,
D is —CO—, and
E is —CO— or —CO—O—

For example, in an ether linkage, nd is 0, ne is 0 and Q is —O—; in an ester linkage, nd is 1, ne is 0, D is —CO— and Q is —O—; in an anhydride linkage, nd is 1, ne is 1, D is —CO—, E is —CO—, and Q is —O—; and in a carbonate linkage, nd is 0, ne is 1, E=—CO—O—, and Q is —O—. Other biodegradable linkages are those present in polyorthoesters, which have the structure:

—C(OR$^1$)(OR$^2$)(OR$^3$)— where two of R$^1$, R$^2$ and R$^3$ are part of the polymer backbone.

b Moieties b is a bond or a moiety linking the Cy moiety to an intermediate point on the polymer backbone or to a terminal moiety. Thus, b may for example be a covalent bond, or a divalent organic moiety (e.g. an aliphatic, aromatic or mixed aliphatic/aromatic moiety) or inorganic moiety. Examples of b moieties include ester (i.e. —CO.O—), carbonyl, amide, amine oxide, hydrocarbon (for example phenylene), amino, ether, polyoxyalkylene, and ionic salt linkages (for example a carboxyalkyl ammonium, sulfonium or phosphonium ion pair).

Cy Moieties

The Cy moieties (which provide chains pendant from an intermediate location and/or from a terminal location of a CYC carrier) in a particular CYC carrier may be the same or different. The Cy moieties must be such that they are capable of interacting with other Cy moieties, for example other Cy moieties elsewhere on the same carrier and/or on a different compound, which may be a polymer (which may or may not be a CYC polymer) and/or on a non-polymeric compound, to provide crystallinity. The interaction between the Cy moieties is generally through hydrogen bonds or Van der Waals forces, rather via covalent or ionic bonding.

The Cy moieties can be of any kind, for example aliphatic, e.g. alkyl, or mixed aliphatic aromatic. The CYC carriers contain Cy moieties such that the carrier, when examined on a DSC in the manner defined below, has a heat of fusion of at least 4 J/g and a Tp of at least 0° C. resulting from crystallization of the CYC moieties. Some CYSC polymers having these characteristics are known and have been referred to by those skilled in the art as side chain crystalline polymers (sometimes abbreviated to SCC polymers or SCCPs).

The Cy moieties often comprise a linear carbon chain of at least 8 or at least 12 carbon atoms directly linked to each other, e.g. 12-50 or 16-30 carbon atoms. The moiety is generally not branched, but can be branched providing that the branching does not prevent the moiety from being capable of crystallization. Similarly, the moiety can be unsubstituted or substituted predominantly only by fluorine atoms, or can be substituted by other moieties which do not prevent the moiety from being capable of crystallization.

Cy can be for example a moiety comprising 6 to 50, e.g. 12 to 50, preferably 12 to 22 or 16 to 22, substantially linear carbon atoms, e.g. a moiety comprising at least 11 methylene moieties, for example 11-49 methylene moieties and a terminal methyl moiety, or a moiety comprising at least 5, e.g. 5 to 49 linear perfluoro or substantially perfluoro methylene moieties and a terminal perfluoromethyl moiety or hydrogen atom. Specific examples of suitable Cy moieties include C14, C16, C18, C20, C22, C30, C40 and C50, in particular n-alkyl moieties containing 14, 16, 18, 20, 22, 30, 40 and 50 carbon atoms, and partially or fully fluorinated n-alkyl groups containing at least 8 carbon atoms, and mixtures of Cy moieties having similar average chain lengths.

Cy Moieties Containing Polyoxyalkylene Moieties

Some useful Cy moieties include polyoxyalkylene, e.g. polyoxyethylene, units. Such a Cy moiety can for example be derived from alkoxy polyoxyalkylene(meth)acrylates, where the alkyl portion of the alkoxy group is preferably an alkyl, particularly an n-alkyl, group containing 12 to 50, preferably 12 to 22 carbons, and the polyoxyalkylene unit is a homopolymer, random copolymer, or block copolymer containing 2 to 100, e.g. 5 to 100, preferably 5 to 60, oxyalkylene units, preferably 2-20, e.g. 2-4, oxyalkylene units. Specific examples of such monomers include cetyl polyethoxylated methacrylate, stearyl polyethoxylated(meth)acrylate, behenyl polyethoxylated(meth)acrylate, lauryl polyethoxylated (meth)acrylate, cholesterol polyethoxylated(meth)acrylate and the like. The polyoxyalkylene unit can be attached to the alkyl side chain portion, as for example in hydroxypolyalkyleneoxyalkyl(meth)acrylates with similar alkyl and polyalkyleneoxy groups as above, e.g. hydroxypolyethleneoxystearyl acrylate, hydroxypolyethyleneoxycetyl methacrylate and the like.

All the moieties of the formula —Y(b-Cy)- in a CYC polymer can be the same, or there can be a plurality of (i.e. two or more) different types of moiety which differ from each other in one or more of Y, b and Cy. In some CYC polymers containing a plurality of different types of —Y(b-Cy)- moiety, the different types are randomly distributed throughout the polymer; in others, the different types are distributed in a desired non-random fashion in at least part of the polymer, such as in a block copolymer or a graft copolymer. For example, the polymer can comprise at least one polymer block which comprises only one type of repeating unit of a first formula —Y(b-Cy)- and a second polymer block which comprises only repeating units of a second formula —Y(b-Cy)-. Alternatively the polymer may comprise one or more sections which contain a plurality of different —Y(b-Cy)- moieties distributed randomly, and at least one polymer block which comprises (i) only repeating units of one or other of the different —Y(b-Cy)- moieties and/or a third —Y(b-Cy)- moiety, or (ii) a plurality of randomly distributed different repeating units of two or more of the first, second and third moieties.

When there are two or more different —Y(b-Cy)- moieties, the Cy moieties may have, for example, an average length of 6 to 50 linear carbon atoms, the average being calculated by adding all lengths of all the Cy moieties in the polymer (or, in the case of a block, including graft, copolymer, all the Cy moieties in the block) and dividing by the number of Cy moieties. The average length may have, for example, an accuracy of +/−3-10%, e.g. +/−5%.

A CYSC polymer can consist essentially of —Y(b-Cy)- moieties. However, many useful CYSC polymers contain less than 75%, or less than 50%, e.g. 1 to 75%, 5 to 50%, 15-50%, 15-30% or 10 to 25%, of —Y(b-Cy)- moieties, for example less than 1%, 3%, 5%, 7%, 10%, 15%, 20%, 25%, 30%, 40% or 50% of —Y(b-Cy)- moieties. Particularly at the lower end of the —Y(b-Cy)- moiety content, in order to enhance crystallinity, the Cy moiety preferably contains at least 18 linear carbon atoms and/or the —Y(b-Cy)- moieties are present as grafted chains or blocks which consist essentially of the —Y(b-Cy)- moieties.

As briefly noted above, CYC polymers often include other units, in addition to the repeating units of formula (1) and/or the terminal units of formula (2). As noted above, those other units can for example be represented by the formula

 (3)

where Z is a moiety forming part of the polymer backbone and Rz represents a monovalent moiety which does not comprise a Cy moiety. All the repeating units of the formula —Z(Rz)- can be the same, or there can be a plurality of different types of repeating unit which differ from each other in Z, or in Rz, or in both Z and Rz. The moieties of the formula —Z(Rz)- can be randomly distributed throughout the polymer, or they can be distributed in a desired non-random fashion in at least part of the polymer. The Z(Rz) moieties contribute to the chemical and other characteristics of the CYC polymer, and their presence can be valuable for this purpose. For example, many useful CYC polymers have an amphiphilic character, with the CYC moieties providing hydrophobic characteristics and the Z(Rz) moieties providing hydrophilic characteristics. A detailed disclosure of the repeating units of formula (3) follows later in this specification.

Other examples of CYSC polymers consist essentially of or comprise atactic, syndiotactic and isotactic polymers of long chain n-alkyl α-olefins (e.g. the atactic and isotactic polymers of C16 olefin, having Tp's of 30° and 60° C. respectively); polymers of n-alkylglycidyl ethers (e.g. the polymer of C18 alkyl glycidylether); polymers of long chain n-alkyl vinyl ethers (e.g. the polymer of C18 alkylvinylether having a Tp of 55° C.); polymers of long chain n-alkyl-α-epoxides (e.g. the polymer of the C18 alkyl α-epoxide having a Tp of 60° C.); polymers of long chain n-alkyloxazolines (e.g. the polymer of C16 alkyl oxazoline having a Tp of 155° C.); polymers obtained by reacting an hydroxyalkyl acrylate or methacrylate with a long chain alkyl isocyanate (e.g. the polymers obtained by reacting hydroxyethyl acrylate with C18 or C22 alkyl isocyanate and having Tp's of 78° and 85° respectively); and polymers obtained by reacting a difunctional isocyanate, a hydroxyalkyl acrylate or methacrylate, and a long chain fatty alcohol (e.g. the polymers obtained by reacting hexamethylene diisocyanate, 2-hydroxyethyl acrylate, and C18 or C22 alcohols).

—Z(Rz)- Moieties

In CYSC polymers, the —Z(Rz)- units are often derived from monomers that can be easily copolymerized with the monomers which provide the Cy-containing moieties of formula (1), with Rz being chosen to provide the CYSC polymer with desired properties, for example hydrophilic properties. For example, Z and $Y_{ch}$ can both be derived from a monomer containing an ethylenic double bond, e.g. an ester or other derivative of acrylic or methacrylic acid.

An ECC polymer has a backbone which is made up of —Z(Rz)- units, and optionally units of formula (1). As described in detail below, in many ECC polymers, the Z moieties comprised bioerodable linkages, for example ester linkages. In ECC polymers, the Rz moieties (in contrast to their role in CYSC polymers) may simply be hydrogen atoms or other moieties which are not chosen to contribute to the physical or chemical properties of the polymer (though they may of course do so).

In both CYSC and ECC polymers, the repeating units of the formula —Z(Rz)- can be the same, or there can be a plurality of different types of repeating unit which differ from each other in Z, or in Rz, or in both Z and Rz. If the CYC polymer contains different repeating units (of either formula (1) or formula (2) or both), the repeating units can be randomly distributed throughout the polymer, or they can be distributed in a desired non-random fashion in at least part of the polymer.

—Z(Rz)- Units in CYSC Polymers.

The presence of Z(Rz) moieties in a CYSC polymer generally depresses the melting temperature and reduces the crystallinity of the CYSC polymer, to an extent which is dependent on the proportion and distribution of the Z(Rz) moieties and the nature of the Z(Rz) moieties. The Z(Rz) moieties also contribute to the chemical and other characteristics of the CYSC polymer, and their presence can be valuable for this purpose. For example, many useful CYSC polymers have an amphiphilic character, with the Cy-containing moieties providing hydrophobic characteristics and the Rz moieties providing hydrophilic characteristics.

The Z(Rz) moieties in a CYSC polymers can be of any kind, for example aliphatic, e.g. alkyl, or mixed aliphatic aromatic. The Z(Rz) moieties can contain any suitable linking group through which they are linked to each other and to the Y(Rc) moieties. For example the polymer can comprise sections which comprise the Z(Rz) moieties and which are polyacrylate, polymethacrylate, polyalkyl (meth)acrylate, poly-N-alkyl acrylamide, poly-alkyl oxazoline, poly-alkyl vinyl ether, poly-alkyl 1,2-epoxide, poly-alkyl glycidyl ether, polyvinyl ester, poly-acrylamide, poly-methacrylamide, polymaleimide, poly-α-olefin, poly-p-alkyl styrene, poly-alkyl vinyl ether, polyolefin, polyether, polyurethane, polysilane, polysiloxane, or poly(alkyl phosphazene).

All the Z(Rz) moieties can be the same, or there can be two or more different Z(Rz) moieties, randomly distributed and/or arranged in a desired distribution, as for example in a block copolymer in which one of the blocks comprises essentially only one type of Z(Rz) moiety, and another of the blocks comprises essentially only another type of Z(Rz) moiety. The Z moieties (which, when there are two or more different types of Z moiety, can be the same or different) can for example be derived from the addition and/or condensation polymerization of suitable monomers, e.g. acrylic, methacrylic, olefinic, epoxy or vinyl monomers.

The bond between Z and Rz can be any bond as described for the bonds between Y and Rc. The bond may be hydrolytically stable, unstable, or labile to hydrolysis or enzymatic cleavage.

Suitable monomers from which Z(Rz) moieties can be derived can contain the desired Rz moieties, and/or can contain Rz precursor moieties some or all of which are converted into Rz moieties during or after the polymerization. Suitable monomers are for example alkyl (e.g. 2-ethylhexyl, butyl, ethyl, methyl) (meth)acrylates, hydroxyalkyl (meth)acrylates (e.g. hydroxyethyl acrylate, hydroxyethyl methacrylate) alkoxyalkyl (meth)acrylates (e.g. methoxyethyl acrylate, ethoxyethyl methacrylate), and hydroxypolyoxyalkylene (meth)acrylates (e.g.—hydroxypolyoxyethylene methacrylate or acrylate where the ethyleneoxy units are from 4 to 50), other (meth)acrylates (e.g. glycidal methacrylate, (acetoacetoxy)ethyl methacrylate), acrylamides and methacrylamides; styrene; monoacrylic functional polystyrene; alkyl vinyl ethers, and alkyl vinyl esters; and in all of which monomers the alkyl groups are alkyl groups which are not Rc moieties, for example n-alkyl moieties containing less than 12, e.g. 1, 2, 3, 4, 5, 6, 7, 8, 9, 10, 11, or 12 carbon atoms (e.g.

vinyl laurate); and polar monomers, for example acrylic acid, methacrylic acid, itaconic acid, dimethylaminoethyl methacrylate, diethylaminoethyl methacrylate, t-butyl acrylamide, dimethylaminopropyl methacrylamide, N-isopropyl acrylamide, acrylonitrile, methacrylonitrile, maleic anhydride, monobutyl fumarate, vinyl acetate, N-vinyl pyrrolidone, and comonomers containing amine groups.

In certain embodiments Rz may comprise polyoxyalkylene e.g. polyoxyethylene, moieties, for example a polyoxyalkylene moiety which links the Z moiety to an end group which is not an Rc moiety The Rz moieties in CYSC polymers can for example include one or more desired functional groups, including, but not limited to, the functional groups forming part of the compounds listed below (the disclosure of those functional groups being independent of the moiety forming the remainder of the listed compound).

In some embodiments, the CYSC polymer includes Z(Rz) moieties that can form a covalent bond with the drug or other bioactive material. In such embodiments, the extent of covalent linkage between the polymer and the release material will be an important factor in determining release characteristics of the release composition.

In some embodiments, the CYSC polymer comprises functional groups to assist in the transport of the release composition into a biological system e.g., through a membrane or into a cell or through a mucous membrane layer, or to assist in the adherence of the composition to deliver the release material. For example the composition can include mucoadhesives sites, dermal adhesives, or large molecules that enhance bioavailability and reduce immunogenicity, for example, polyoxyalkylene vinyl monomers, e.g., with PEG or PEGylated groups. These PEGylated groupings in the CYC polymer will typically be introduced via comonomers, In some embodiments, the CYSC polymer includes units comprising ionic groups, e.g. units derived from ionic vinyl monomers. The ionic groups can help to stabilize the polymer formulation or help in disassociating the formulation in body fluids. For example, a CYSC polymer containing carboxylate functional groups can reduce or eliminate release of a drug in the acidic environment of the stomach, but can swell in the alkaline environment of the small intestine, thereby releasing the drug in the upper intestine. Other embodiments may employ for example, PEGylated monomers or acidic or other non-ionic or ionic monomers respectively that may be incorporated together as part of the same CYSC polymer or may be present in separate CYSC polymers to be mixed with a drug. The route of drug administration will often be a factor in determining the desirability of the number of ionic or hydrogen bonding groups in the CYSC polymer. For example, a small protein or polypeptide can be mixed with a CYC polymer to make a stable drug formulation and then administered orally. The protein administered by itself orally might be destroyed when exposed to the highly acidic environment of the stomach. When mixed with CYC polymer, the protein would be protected from degradation. Alternatively an acid-stable component may be added such as transferrin. In certain embodiments, a protein may be complexed with an absorption enhancing component such as an organic acid, for example with deoxycholic acid, hydroxypropyl-g-cyclodextrin, cholic acid, etc.

In some CYSC polymers, the Z(Rz) moieties may also enhance the physical surface properties of the release composition. For example, polyoxyethylene (meth)acrylate units can provide beneficial slip or hydrophilic properties to tubing, catheters, probes and other medical devices. In some embodiments, the Z(Rz) moieties may also help in the sustained release or delivery of the drug.

Useful Rz moieties in CYSC polymers include:

(1) Nitrogen-containing side chains, for example the moieties which result from the polymerization of the groups of monomers and specific monomers listed below. It is noted that the identified Rz moieties and/or the functional groups thereon can also be obtained through the use of other monomers: N,N-dialkyl amino(in particular, dimethylamino) (meth)acrylates; ammonium salt-containing (meth)acrylates, for example 2-trimethylammonium methylmethacrylate chloride, methacrylamidopropyl trimethylammonium chloride, N,N-(diethyl or dimethyl)aminoethyl(meth)acrylate methosulfate; N-vinylpyrrolidinone; imides like the ring-closed reaction products of maleic or itaconic anhydride with primary amines; 2-methacryloxy-N-ethylmorpholine; n- or t-butylacrylamide; (meth)acrylamide; dimethylaminopropyl methacrylamide; 2-t-butylaminoethyl methacrylate; (meth)acrylonitrile; t-butylaminoethyl (meth)acrylate; acryloylmorpholine; N-(2-hydroxyethyl)acetamide; 1-piperidinoethyl (meth)acrylate; and amine oxide containing monomers obtained by reacting alkyl amine containing side chain containing monomers with an oxidizing agent to give an amine oxide of the precursor alkyl amine.

In certain specific embodiments, the formulations of the invention specifically exclude Rz side chains derived from N-vinylpyrrolidinone.

(2) Oxygen-containing side chains, for example the moieties which result from the polymerization of the groups of monomers and specific monomers listed below, including carboxyl- and sulfonic acid-containing monomers and salts thereof. It is noted that the identified Rz moieties and/or the functional groups thereon can also be obtained through the use of other monomers: acrylic acid, methacrylic acid; itaconic anhydride; itaconic acid; maleic anhydride; maleic acid; fumaric acid; monoesters and monoamides of fumaric acid, maleic acid, crotonic acid, and 2-acrylamido-2-methylpropane sulfonic acid ("AMPs"); vinyl sulfonic acid; hydroxyalkyl (meth)acrylates, in particular, hydroxyethyl, hydroxypropyl, and hydroxybutyl) (meth)acrylates; tetrahydrofurfuryl (meth)acrylate; glycidyl methacrylate; alkoxyalkyl (meth)acrylates, e.g. methoxyethyl (meth)acrylate; hydroxycaprolactone acrylate; 1-acryloxy-2-hydroxy-3-phenoxypropane; methylol methacrylate; ethoxyethyl (meth)acrylate; 2-(2-ethoxyethoxy)ethylacrylate; acetoacetoxyethyl (meth)acrylate; phenoxyethyl (meth)acrylate; (meth)acrolein; alkoxy or hydroxyl (polyoxyalkylene) alkyl (meth)acrylates, e.g. methoxy- or hydroxypolyoxyethylene (meth)acrylates, for example those in which the moles of ethyleneoxy units are from 2 to 80, preferably 6 to 50; alkoxy- or hydroxypolyoxypropylene-polyoxyethylene alkyl (meth)acrylates, for example those in which the blocks of each oxyethylene and oxypropylene unit are present in 1/1 to 1/3 ratios whereby the amount of oxyalkylene units in each block is 5 to 100, preferably, 5 to 60 units.

(3) Fluorine-containing side chains, for example the moieties which result from the polymerization of the groups of monomers and specific monomers listed below. It is noted that the identified Rz moieties and/or the functional groups thereon can also be obtained through the use of other monomers: trifluoroethyl (meth)acrylate; heptadecafluorodecyl (meth)acrylate; octafluoropentyl (meth)acrylate; eicosafluoroundecyl (meth)acrylate; hexadecafluorononyl (meth)acrylate; and tetrahydroperfluorodecyl (meth)acrylate.

(4) Phosphorus-containing side chains, for example the moieties which result from the polymerization of the monomers listed below and similar monomers. It is noted that the identified Rz moieties and/or the functional groups thereon can also be obtained through the use of other monomers: 2-methacryloyloxyethyl phosphoryl choline; 2-acryloyloxypropyl phosphoryl choline; and stearyl fumaroylethyl phosphoryl choline.

(5) Silicon-containing side chains for example the moieties which result from the polymerization of the groups of monomers and specific monomers listed below. It is noted that the identified Rz moieties and/or the functional groups thereon can also be obtained through the use of other monomers: silyl monomers, e.g. trimethylsiloxy ethyl (meth)acrylate, 3-acryloxypropyl trimethoxysilane, and 3-acryloxypropyl tris(trimethylsiloxy)silane, monomethacryloxymonotrimethylsiloxyterminated polyethylene oxide, monomethacryloxypropyl alkyl polydimethylsiloxane where the alkyl group contains 1-8 carbon atoms, preferably 1 or 4 carbon atoms, and similar materials sold by for example Gelest as MCR-M17 and MCR-M11, and the like.

(6) Ligand groups which bind to target receptor sites. e.g., receptor proteins that are differentially over-expressed on target cells, for example cancerous cells. Ligands can be physically mixed as well as being part of the CYC polymer. Ligands are discussed in detail later.

Some CYSC polymers include Z(Rz) moieties in which at least some of the Rz moieties are hydrophilic, the CYC polymer then being an amphiphilic copolymer having both hydrophobic and hydrophilic characteristics. Formulations comprising such amphiphilic polymers may form micelles or emulsions or liposomes in water, for example containing a hydrophobic drug within the hydrophobic core. It is often convenient to provide CYSC polymers with hydrophilic character by the inclusion of polyoxyethylene oxide units ("pegylation").

Some CYSC polymers include Z(Rz) moieties in which all the Rz moieties are hydrophobic, in which case the CYSC polymer will be a copolymer having only hydrophobic characteristics.

The CYSC polymer generally contains Z(Rz) moieties in amount less than 95%, generally less than 70%, for example less than 50%, e.g. 5 to 25%, based on the weight of the polymer (e.g. about 5, 7, 10, 15, 17, 20, 23 or 25%).

Cross-Linked CYSC Polymers and CYSC Polymer Gels.

The CYC polymers are generally not cross-linked. However, when a cross-linked CYSC polymer is desired, the monomer mixture can include a suitable cross-linking monomer or cross-linking reactant, which can be added at an appropriate time during the process, for example (a) when preparing the polymer in a desired shape, followed later by the addition of a release material, or (B) preparing the non-cross-linked polymer combining that polymer with a release material, and then adding a cross-linking agent to set the mixture in a particular shape.

Gels and hydrogels can comprise a cross-linked CYSC polymer. Also, in some embodiments, the composition comprises a crosslinked CYSC polymer which, because a cross-linked polymer at least partially retains its shape even under conditions which would cause otherwise melting or swelling, e.g. above Tp, tends to hold a release compound longer than the corresponding non-crosslinked polymer. Some embodiments specifically exclude CYSC polymers which are cross linked or immobilized on a support so that they cannot flow at temperatures above their melting temperature.

In some embodiments, a CYSC polymer has a gel structure. A gel structure can be provided by including a crosslinking multifunctional monomer in the monomer mixture used to prepare the CYSC polymer. Such monomers are best employed in emulsion polymerizations, since, in other types of polymerization, they can result in viscosities which are difficult to handle. Exemplary crosslinking monomers are ethylene glycol dimethacrylate, butylene glycol dimethacrylate, trimethylol propane triacrylate, hexane diol diacrylate and the like. These crosslinking monomers are generally employed only in small amounts, e.g. less than 0.5%, or less than 1%, such as 0.1% to 5%, or 0.2 to 2%.

Hydrogels can be hydrophobic, or amphiphilic, and they can be ionic or non-ionic. Non-ionic hydrogels swell when they absorb water. Ionic hydrogels, which can be anionic or cationic, can be caused to swell to varying degrees by a change in pH. An alkaline pH causes swelling of an anionic gel (because ionic groups like carboxyl are ionized at high pH), whereas a low pH causes swelling of cationic gels. These facts, optionally combined with the response of CYSC carriers to changes in temperature around Tp, can be utilized to control release of a release material, and provide a powerful tool for making compositions, particularly pharmaceutical formulations, which will release a release material at a desired location.

In one embodiment, a pH sensitive hydrogel containing units derived from acrylic acid will facilitate protein loading and will protect the protein in the stomach, but swell and release the protein in the small intestine, where the alkaline environment causes hydration and swelling of the hydrogel by interaction with the units derived from acrylic acid. The swelling of the hydrogel can regulate the release of drug, because the hydrogel acts like a membrane, thereby overcoming the normal "burst effect" and allowing slow release of the protein.

In another embodiment, a solid powdered hydrogel is mixed with a solid powdered drug or other release material, and then hydrated for administration.

In another embodiment, a CYSC polymer containing (in addition to the —Y(b-Cy)- units) units derived from a N-isopropyl acrylamide comonomer, either alone or in combination with units derived from acrylic and/or methacrylic acid, can form an amphiphilic hydrogel which can associate with (depending on the percentage of the hydrophobic and hydrophilic portions) either a hydrophobic or a hydrophilic release material.

In another embodiment, the CYSC polymer is in the form of a non-ionic hydrogel prepared by polymerizing a monomer component comprising a Cy-containing monomer and a neutral hydrophilic comonomer, for example, hydroxyethyl methacrylate, together with a small portion of a crosslinking agent, e.g. ethylene glycol dimethacrylate. In a modification of this embodiment, polyoxyethlene glycol methacrylate monomer is also included, thus adding to the gel structure and providing possible antithrombogenic properties to a pharmaceutical formulation. This polymer is also an amphiphilic polymer. As such it can be compatible with release materials which are either or both hydrophilic and hydrophobic.

In another embodiment, the CYSC polymer is in the form of a neutral hydrogel prepared by polymerizing a Cy-containing monomer, acrylamide and t-butyl acrylamide, together with a small amount of methylene bis acrylamide. Such a hydrogel can associate with a hydrophilic or hydrophobic release material.

In another embodiment, the CYSC polymer is in the form of a hydrogel prepared by polymerizing a Cy-containing monomer, acrylic acid and a block polyoxypropylene/polyoxyethylene/polyoxypropylene ester of acrylic or methacrylic acid. The resulting amphiphilic polymer, dependent on the block structure of the oxyalkylene ester, will absorb varying amounts of either or both of a hydrophilic and a hydrophobic release material. These release materials may be released slowly dependent on the hydrophobe/hydrophile balance of the oxyalkylene ester and the hydrophobe from the SCC monomer.

In another embodiment, a CYSC polymer and a drug are formulated as a solution which is of low viscosity before administration, but which, when injected into the body where it is exposed to another pH, forms a hydrogel which provides an in-situ gel reservoir for release of the drug dependent upon the hydrophobic and hydrophilic properties of the CYSC polymer.

CYC Polymers in the Form of Emulsions

In some embodiments, the CYC polymer is in the form of an emulsion. The average size of the particles in the emulsion (and preferably the maximum size of substantially all particles) is preferably less than 1200 nm, e.g. less than 800 nm or less than 500 nm, for example less than 200 nm or less than 100 nm (0.1µ). In many embodiments, the size of emulsion particles is 50-200 nm, or 50-500 nm, or 100-1000 nm. Some such emulsions can be prepared using the techniques described in U.S. Pat. Nos. 6,199,318 and 6,540,984, the entire disclosures of which are incorporated herein by reference for all purposes. Emulsions are for example useful for compositions to be injected, generally intravenously, but in some embodiments, intramuscularly or into other tissues. In general, injectable emulsion particles have a diameter of less than 800 nm, or they can be less than 20µ, or less than 10µ, or less than 1µ in size.

Mixtures of CYC Carriers

A single CYC carrier or a mixture of CYC carriers can be used. A mixture of CYC carriers can provide a CYC assembly. The CYC carrier or carriers can also be mixed with an additional material, for example a polymer which is not a CYC polymer. The additional material can form a CYC assembly. Examples of such additional materials include main chain crystalline polymers, and bioerodable polyesters. Specific examples of such other polymers, particularly for use in combination with the ECC polymers, include poly(epsilon-caprolactone (PCL), poly(dioxanone), polyhydroxybutyrate (PHB), polyhydroxyvalerate (PHV), polyhydroxyalkanoates (PHAs), polyesters from 3-hydroxypropionic acid, polymers derived from methylene carbonate, polyanhydrides, polyorthoesters, naturally occurring polymers or their hydrolysis or degraded products such as sugars, hydrolyzed starches, hyaluronan (also called hyaluronic acid or hyaluronate), chitan, chitosan, and alkyl polylactides, including those disclosed in WO 2007/0142461 (Baker et al.), U.S. Pat. No. 6,469,133, US published application Nos. 20070142461 and 20010044514, the disclosures of which are incorporated herein by reference for all purposes.

The criteria for the selection of a particular CYC polymer or mixture of CYC polymers, and optionally one or more additional polymers, depend upon the release material and its desired loading and/or release, as further discussed below. Some embodiments of the invention make use of a composition containing a mixture of two or more CYC polymers having substantially different Tps, for example Tps which differ from each other by at least 2° C., or at least 4° C. or at least 6° C. or at least 8° C. or at least 10° C. For example, the composition may contain one or more CYC polymers melting at about 37° C. and one or more other CYC polymers melting at about 39° C. and/or one or more other polymers melting at about 41° C. Other embodiments make use of mixtures of CYC polymers having a release material bound through a range of ionic strengths as defined by the pKa or pKb of the drug-polymer pair.

CYSC Acrylate Polymers

Some embodiments of the invention make use of CYSC polymers which are polyacrylates, for example poly(meth)acrylates. In poly(meth)acrylates, the $Y_{ch}$ moieties, and generally the Z moieties, if present, have the formula

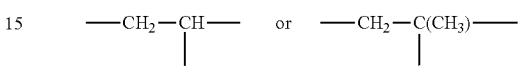

Such polymers preferably comprise units derived from n-alkyl (meth)acrylates in which the n-alkyl group contains at least 16, e.g. 16-50, e.g. 18-22 carbon atoms.

For example, in one embodiment, the CYSC polymer comprises one or more polymers selected from the group consisting of (1) polymers which consist essentially of units derived from at least one n-alkyl acrylate or n-alkyl methacrylate wherein the n-alkyl group contains 16-30 carbon atoms, and (2) polymers which consist essentially of units derived from at least one n-alkyl acrylate or n-alkyl methacrylate wherein the n-alkyl group contains 16-30 carbon atoms, and units derived f 200 and rom at least one acrylate or methacrylate comonomer containing one or more functional moieties selected from the group consisting of carboxyl, hydroxyl, alkoxypolyalkylene, hydroxypolyalkylene and amino moieties.

Other acrylate polymers contain units derived from (meth)acrylate monomers obtained by modifying very long chain mixtures of aliphatic alcohols, e.g. the Unilin alcohols sold by Baker Petrolite, in which the n-alkyl radicals average C30 or C40 or C50 carbon atoms. Such acrylate polymers can have Tps about 80, 90 or 100° C. respectively. Other acrylate polymers include polymers of long chain n-alkyl oxycarbonylamido-ethylmethacrylates (e.g. the polymers of C18 IEMA, C22 IEMA and C30 IEMA, having Tp's of 56° C., 75° C. and 79° C. respectively); and polymers of medium and long chain n-fluoro alkyl acrylates (e.g. the polymer of C8 hexadecafluoroalkylacrylate and the polymer of a mixture of C8-12 alkyl fluoroacrylates, having Tp's of 74° C. and 88° C. respectively).

Other CYSC Polymers

Other CYSC Polymers include polycarbonates, polyesters, polyester oxazolines and polydioxanones, as described for example below CYSC Polycarbonates Side-chain crystalline dimethylol propionic acid polycarbonates:

As an item of commerce used in water dispersible polyurethanes, dimethylol propionic acid (DMPA) is used as a polyol acid. When this acid is first reacted at the carboxylic acid position with a crystalline fatty alcohol, stearyl alcohol, for example, the crystalline diol ester can then be reacted with dimethyl carbonate to give the crystalline trimethylene carbonate analog which is reacted with trimethylene carbonate at different molar ratios to give a side chain crystalline polycarbonate:

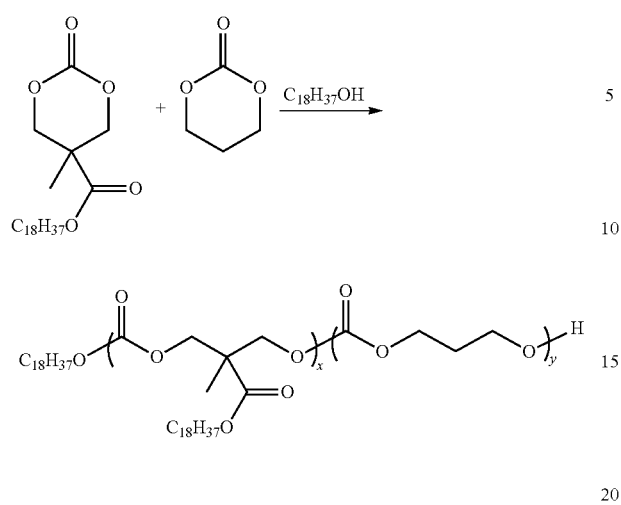

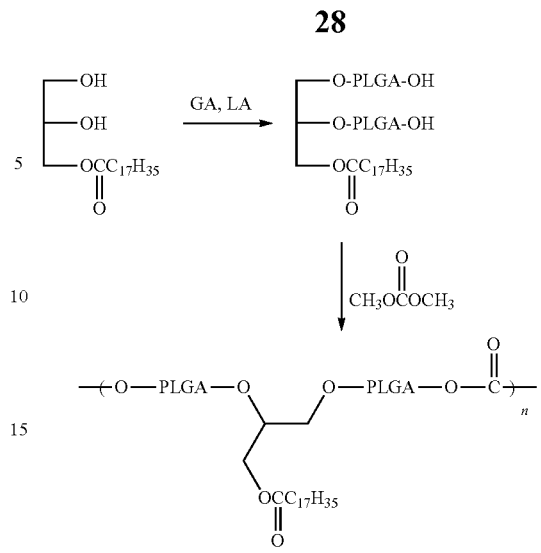

This side chain crystalline polycarbonate provides a high level of hydrophobic alkyl side chains to protect a water sensitive drug, for example, a protein or peptide from degradation during storage in the body and at the same time allows for bioerosion and dissolution of the drug away from the polymer drug matrix once administered.

1) Side-Chain Crystalline Polycarbonates from Glycerin Carbonate:

Glycerin carbonate is an interesting intermediate with a free hydroxyl group. This hydroxyl group can be reacted with stearoyl anhydride to give the ethylene carbonate methylene crystalline fatty ester. Reaction of this intermediate with any diol, for example, 1,3-propanediol, leads to a crystalline fatty ester methylene polycarbonate diol:

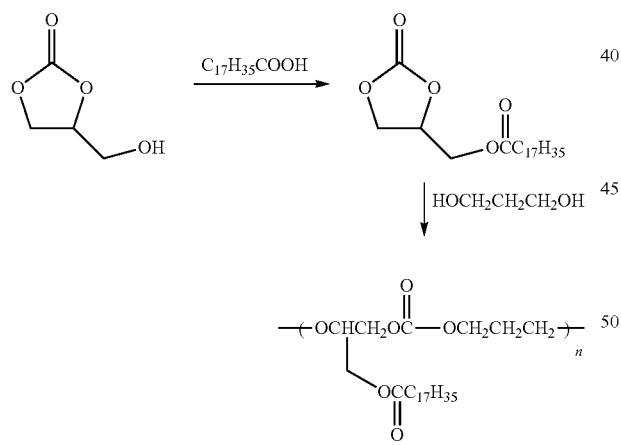

2) Side-Chain Crystalline Polycarbonates from Monoglycerides, Dimethyl Carbonate, and Lactic/Glycolic Acid(s):

A monoglyceride obtained by mono-esterification of glycerin with a crystalline fatty acid, for example, stearic acid, gives a crystalline fatty monoglyceride which can be reacted with at least two moles or more of any combination of lactic, glycolic and 3-hydroxypropionic acids and then this polymeric diol can be reacted with dimethyl carbonate to yield a simple side chain crystalline polycarbonate:

CYSC Polyesters:

a. Side-Chain Crystalline Malic, Citric or Tartaric Acid Polyesters:

These acids—malic, tartaric or citric—contain one or more hydroxy groups. One of these hydroxy groups can be esterified with a crystalline fatty acid to give a polycarboxylic acid crystalline fatty ester which can be then reacted with a simple diol, 1,3-propanediol, for example, to provide a side chain crystalline polyester similar to the well known reaction of a polyol, trimethylol propane with a fatty acid and subsequently with a polycarboxylic acid to give a polyester backbone with pendant fatty acid ester groups. These kinds of polyesters have been used in the industrial coating business:

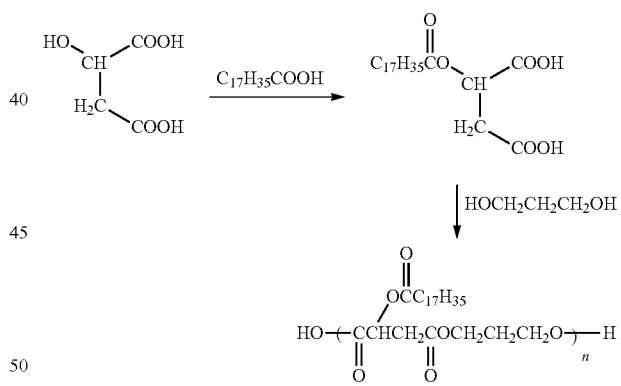

b. Side-Chain Crystalline Malic or tartaric Acid PLGA Polyesters:

Tartaric acid can only be used in small quantities in foodstuffs since at large quantities it is actually toxic. Nevertheless, tartaric acid as its tartrate salt is often used in sour tasting sweet products. It is possible to use in a drug delivery device in small quantities. For example, tartaric acid which is a di-acid has two hydroxyl groups—one adjacent to each of the carboxylic acid groups. Malic acid has one hydroxyl group adjacent to one of the two carboxylic acid groups. If tartaric or malic acid is esterified with a crystalline fatty acid, for example, stearic acid, a crystalline fatty modified polycarboxylic acid is made which can react with a simple diol, 1,3-propanediol, to give a side chain crystalline polyester as in a).

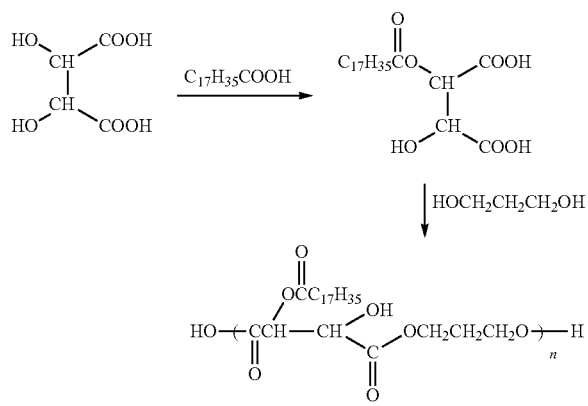

If on the other hand one of the acid groups of tartaric or malic acids is esterified with a crystalline fatty alcohol, a crystalline fatty ester hydroxyl acid is made. This product can then be reacted with stearic acid, stearyl alcohol or the like, to add one or two Cy moieties at the terminal units. This product can then be reacted with lactic and glycolic acids to give a side chain crystalline PLGA:

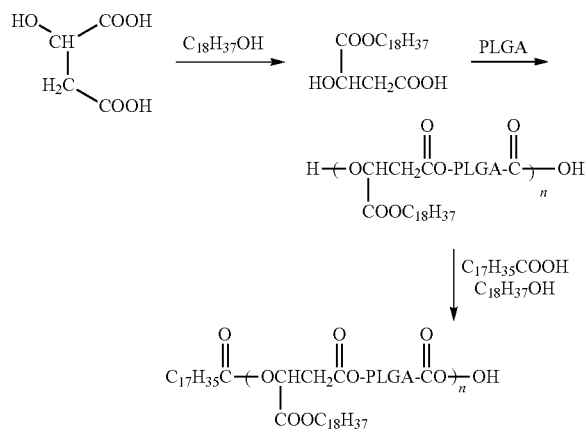

c. Polyesters from Glycidol, Crystalline Fatty Acid and Polybasic Acid:

Glycidol, an epoxy mono-alcohol, can be reacted in a one reaction vessel sequence in the presence of crystalline fatty acid and polycarboxylic acid, for example, succinic anhydride, to give a side chain crystalline polyester:

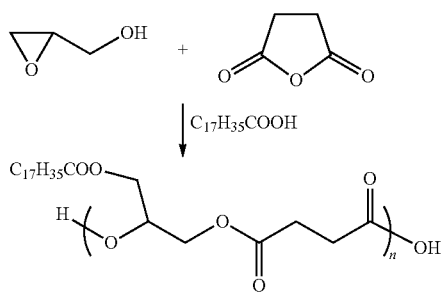

Or, the DMPA fatty crystalline alcohol ester can be reacted with a simple dicarboxylic acid (or precursor), for example, succinic anhydride, to yield a side chain crystalline polyester:

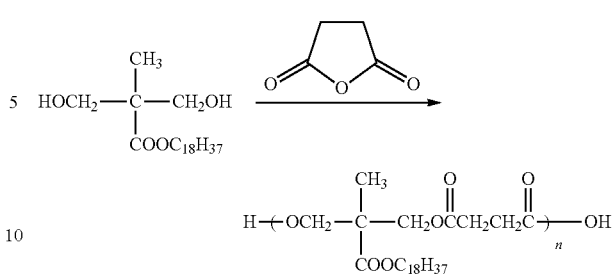

A. Bioerodable Side-Chain Crystalline Oxazolines:

TrisAmino, an amino polyol commercially available from Angus (Dow) and used in many medical applications where bioerodibility is critical can be first mixed and reacted with a fatty acid, for example, stearic acid, to give a fatty amide polyol which on heating cyclizes to a crystalline fatty oxazoline polyol. This polyol is easily reacted with a dibasic (or polybasic acid), in this case a dibasic acid precursor, succinic anhydride to give a side chain crystalline and bioerodable polyester-oxazoline:

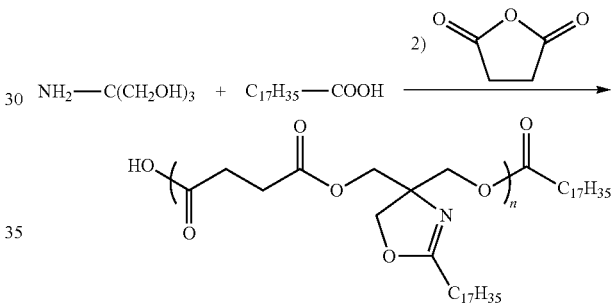

The oxazoline moiety may be desirable for mixing with some types of drugs to insure a uniform, compatible mixture of drug and polymer to provide repeatable and consistent drug delivery results with a low burst profile.

B. Crystalline Alkyl Dioxanones:

It is well known that a p-dioxanone can be prepared from a glycol cyclizing with glycolic acid to give the p-dioxanone. When this intermediate is reacted with a simple diol, 1,3-propanediol or hexanediol, for example, a copolymer of the 1,4-dioxane-2-one with the diol forms. Also, the 1,4-dioxane-2-one under heating and catalyst yields a homopolymer. If we use a long chain crystalline alpha-olefin oxide, and hydrolyze this olefin oxide to the crystalline long chain 1,2-dihydroxy alkane, we synthesize a crystalline substituted p-dioxanone. This crystalline dioxanone once polymerized will give a side chain crystalline polydioxanone:

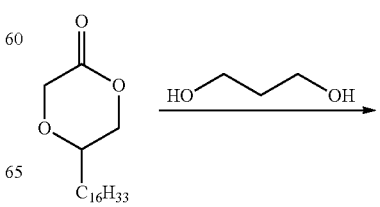

-continued

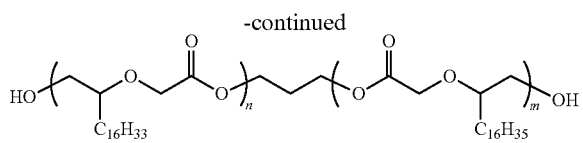

ECC Polymers

In one embodiment, an ECC polymer comprises at least one moiety having the formula $$-Qx(-b-Cy)_q \quad (Q2)$$

wherein Qx is a moiety having a valence of at least (q+1), q is at least 2, for example 2, 3, 4 or 5, and b and Cy are as hereinbefore defined. The ECC polymer can for example contain two, three or four such moieties, which can be the same or different. The ECC optionally has one or more of the following characteristics:—

(1) it has a molecular weight of 3,000-20,000, e.g. 3,000-10,000 or 3,000-8,000;
(2) the backbone of the polymer consists essentially of carbon atoms, e.g. is a polyacrylate;
(3) the backbone of the polymer comprises bioerodable linkages, e.g. is a PGLA;
(4) the value of (Tp–To) is less than $Tp^{0.7}$, e.g. less than $Tp^{0.6}$, or less than 5° C.;
(5) the molar percentage of units comprising Cy moieties is less than 30% e.g. less than 20% or less than 10%, and/or more than 1%, e.g. more than 2% or more than 4%;

in one embodiment, an ECC polymer has a backbone comprising bioerodable linkages, e.g. linkages having the formula $$-D_{nd}-Q-E_{ne}- \quad (Q1)$$

as hereinbefore defined, and optionally has at least one of the following characteristics:—

(1) it has a molecular weight less than 10,000, e.g. less than 8,000, or less than 7,000, or less than 5,000, and/or a molecular weight greater than 600, e.g. greater than 800 or greater than 1000;
(2) the molar percentage of moieties comprising CYC moieties is less than 30% e.g. less than 20% or less than 10%, and/or more than 1%, e.g. more than 2% or more than 4%; and
(3) at least 50 mol percent, e.g. at least 70 mol % or at least 80 mol %, e.g. substantially all, of the repeating units forming the backbone of the polymer are free of Cy moieties;

In one embodiment, an ECC polymer has a backbone which comprises (i) bioerodable linkages having the formula

—O—CO—O—

(ii) methylene moieties, and (iii) substituted methylene moieties in which the substituent is a b-Cy moiety, the polymer optionally having at least one of the following characteristics:

(1) it has a molecular weight less than 20,000, e.g. less than 15,000, or less than 10,000, or less than 8,000, or less than 5,000;
(2) the molar percentage of units comprising Cy moieties is less than 30% e.g. less than 20% or less than 10%, and/or more than 1%, e.g. more than 2% or more than 4%;
(3) it comprises Cy moieties which comprise an n-alkyl moiety containing 16-30, e.g. 18-22, carbon atoms;
(4) it has a value of (Tp–To) which is less than $Tp^{0.7}$, e.g. less than $Tp^{0.6}$, or less than 5° C.;
(5) it has a heat of fusion of 3-50, e.g. 3-30 or 3-22 or 3-10, J/g; and (6) at least 50 mol percent, e.g. at least 70 mol % or at least 80 mol %, of the repeating units forming the backbone of the polymer are free of CYC moieties.

In one embodiment, an ECC polymer comprises repeating units having the formula $$-R_{alkylene}-CO-O-$$

wherein $R_{alkylene}$ is a substituted or unsubstituted straight chain or branched alkylene radical, for example —$(CH_2)_2$— or —$CH(CH_3)$—$CH_2$—; the CYC polymer optionally having one or more of the following characteristics:—

(1) it has a molecular weight less than 10,000, e.g. less than 8,000, or less than 7,000, or less than 5,000, and/or a molecular weight greater than 500 or greater than 1000, e.g. greater than 1500, e.g. 2000-5000;
(2) the molar percentage of units comprising CYC moieties is less than 30% e.g. less than 20% or less than 10%, and/or more than 1%, e.g. more than 2% or more than 4%;
(3) the value of (Tp–To) is less than $Tp^{0.7}$, e.g. less than $Tp^{0.6}$, or less than 5° C.;
(4) at least some of the CYC moieties are present in terminal units having one or more of the formulas (J)-(L) below in which the $R_{alkylene}$ moieties can be the same as or different from the $R_{alkylene}$ moieties in the repeating units $$-R_{alkylene}-CO-O-Cy \quad (J)$$

$$-O-CO-R_{alkylene}-CO-O-Cy \quad (K)$$

$$-O-CO-R_{alkylene}-CO-O-Y_{term}-R_{pbalc}-O-Cy \quad (L)$$

where $R_{pbalc}$ is the residue of a polyol, and has for example the formula

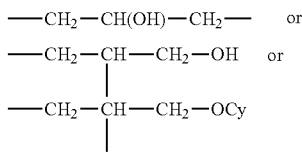

(5) the CYC polymer contains a plurality of polyalkylene ether units, for example a terminal polymeric block having the formula $$HO-(CH_2-CH_2-O-)_{npeg}$$

where npeg is 2-150, e.g. 6-100;
(6) at least some of the CYC moieties are present in repeating units of formula (1) above, for example repeating units having the formula

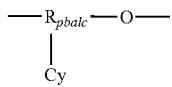

where $R_{pbalc}$ is the residue of a polyol, for example a polyethylene glycol, 1,3-propanediol, glycerin or sorbitol, and optionally contains two or more CYC moieties;
(7) it contains repeating units having the formula and repeating units having the formula $$-R_{alkylene1}-CO-O-$$

and repeating units having the formula $$—R_{alkylene2}—CO—O—$$

wherein $—R_{alkylene1}—$ is different from $—R_{alkylene2}—$, e.g. one is $—(CH_2)_2—$ and the other is $—CH(CH_3)—CH_2—$, and (7a) at least one of $—R_{alkylene1}—CO—O—$ and $—R_{alkylene2}—CO—O—$ is present only in the form of moieties having the formula $$(—R_{alkylene1}—CO—O—)_N$$

or $$(—R_{alkylene2}—CO—O—)_N$$

respectively, wherein N is equal to (1+X) wherein X is zero or an even integer, or (7b) at least some of the units are not derived from a cyclic dimer, or (7c) at least one of $—R_{alkylene1}—CO—O—$ and $—R_{alkylene2}—CO—O—$ is not present only in moieties having the formula $$(—R_{alkylene1}—CO—O—)_2$$

or $$(—R_{alkylene2}—CO—O—)_2$$

respectively;

(9) it has a heat of fusion of 3-50, e.g. 3-30 or 3-22 or 3-10, J/g

(10) it is part of a composition which also contains a material which is bioactive and/or which is known as an ingredient for a drug formulation, a personal care composition, or a composition for application to a plant, seed or soil; and

(11) at least 50 mol percent, e.g. at least 70 mol % or at least 80 mol %, of the repeating units forming the backbone of the polymer are free of CYC moieties.

Preferred ECC polymers for use in this invention (A) comprise a plurality of polymeric molecules each of which consists essentially of
  (i) a polymer backbone which comprises a plurality of repeating units having the formula $$—CF^1F^2—CO—O— \hspace{2em} (ECC\ 1)$$

wherein
  $F^1$ is hydrogen and $F^2$ is hydrogen or methyl, the repeating units being the same or different, and
  (ii) at least one terminal unit which has the formula $$-b\text{-Cy} \hspace{2em} (ECC\ 2)$$

wherein
  Cy is an n-alkyl moiety containing 18-24 carbon atoms, and b is a bond or a moiety which has a valence of at least 2 and which links the Cy moiety to the polymer backbone, and which optionally contains one or more additional Cy moieties;

(B) has a Tp of at least 40° C., a To such that the value of (Tp−To) is less than $Tp^{0.7}$, and a ΔH of at least 5 J/g, and (C) has an Mn of less than 10,000.

In such ECC polymers containing more than one terminal unit of formula (2), and/or a terminal unit containing two or more Cy moieties, for example a total of 2, 3, 4 or 5 Cy moieties in one or more terminal units of formula (2), one or both of b and Cy can be the same or different in the different terminal units, and in a terminal unit containing more than one Cy moiety, the Cy moieties can be the same or different. The ECC polymer can optionally contain, in addition to the units of formulas (ECC 1) and (ECC 2), repeating units and/or terminal units having a different formula. For example, the repeating units can be derived from a mixture of lactic acid and glycolic acid, and the polymer can contain two terminal units of formula (2), each containing at least one Cy moiety, e.g. an n-alkyl moiety containing 18 carbon atoms.

These preferred ECC polymers can for example be prepared by endcapping a preformed PLGA by (i) reaction of the carboxyl end group of the PLGA with an alcohol containing a Cy moiety, e.g. stearyl alcohol or behenyl alcohol, or (ii) reaction of the carboxyl end group of the PLGA with a polyhydroxy compound, e.g. a sugar such as sorbitol, followed by esterification of one or more of the remaining hydroxy groups with a carboxylic acid (or the like) containing a Cy moiety, and/or (iii) by reaction of the hydroxyl end group of the PLGA with an n-alkyl carboxylic acid (or the like) in which the n-alkyl moiety contains 18-22 carbon atoms.

These preferred ECC polymers can consist essentially of the moieties of the formulas (ECC 1) and (ECC 2), i.e. the polymer is derived from a PGA (in which each of $F^1$ and $F^2$ is hydrogen in each of the repeating units), a PLGA (in which each of $F^1$ and $F^2$ is hydrogen in some of the repeating units, and one of $F^1$ and $F^2$ is hydrogen and the other of $F^1$ and $F^2$ is methyl in the other repeating units) or a PLA (in which one of F1 and F2 is methyl and the other of F1 and F2 is hydrogen in each of the repeating units). Alternatively, the polymer can also contain repeating units of a different type, optionally providing further carboxy linkages in the polymer backbone, for example units derived from caprolactone.

The following statements disclose optional characteristics of these preferred ECC polymers. Two or more of the stated characteristics can be present at the same time, except where the context makes this impossible.

(A) the polymer
  (A1) has a molecular weight less than 8,000, or less than 7,000, or less than 5,000;
  (A2) has a value of (Tp−To) which is less than $Tp^{0.7}$, e.g. less than $Tp^{0.6}$, or less than 10° C.;
  (A3) contains less than 30%, e.g. less than 20% or less than 10%, and/or more than 1%, e.g. more than 2% or more than 4%, molar percent of units comprising Cy moieties;
  (A4) has a heat of fusion of at least 10, or at least 20 J/g;
  (A5) at least 50 mol percent, e.g. at least 70 mol % or at least 80 mol %, of the repeating units forming the backbone of the polymer are free of Cy moieties;
  (A6) the terminal units have one or more of the formulas (2A)-(2C) below $$\text{-Cy} \hspace{2em} (2A)$$

$$—CO—O\text{-Cy} \hspace{2em} (2B)$$

$$—R_{pbalc}—CO\text{-Cy} \hspace{2em} (2C)$$

where $R_{pbalc}$ is the residue of a polyol, for example a polyethylene glycol, 1,3-propanediol, glycerin or sorbitol, and optionally contains one or more Cy moieties, the terminal and other Cy moieties, if any, being introduced for example by esterification, transesterification or alkylation of one or more of the hydroxyl groups, e.g. by reaction with an acid or acid chloride containing a Cy moiety; and has for example the formula $$—CH_2—CH(OH)—CH_2—O—CO\text{-Cy}$$

or $—CH_2—CH(O—CO\text{-Cy})—CH_2—O—CO\text{-Cy}$;

(A7) contains less than 170 repeating units of formula $$—CF^1F^2—CO—O—;$$

(A8) is prepared by a process which comprises copolymerizing one or more monomers, i.e. one or more of lactic acid and glycolic acid, and their cyclic dimers, lactide and glycolide, which will result in the repeating units of formula (1) and one or more monomers or components which will result in the terminal units which have formula (2) or which can be converted into terminal units of formula (2). For example, (i) an alcohol containing a Cy moiety can be reacted with lactic acid and glycolic acid, or (ii) a polyol, for example glycerine, 1,3-propanediol or 1,6-hexanediol, can be reacted with glycolic acid and lactic acid to form a PLGA glyceride ester which is end capped with an excess of a carboxylic acid containing a Cy moiety, for example stearic acid or behenic acid;

(A9) is prepared by endcapping a preformed polymer having the formula HO—(—CF$^1$F$^2$—CO—O—)$_n$—H where n is an integer less than 170; the preformed polymer, if prepared by the polymerization of lactide and glycolide, will consist predominantly of pairs of identical repeating units, and if prepared by the polymerization of the monomers (lactic and glycolic acids) will have randomly distributed repeating units; for example (A9a) is prepared by a process which includes the step of reacting the terminal hydroxyl group of a preformed PLA, PLGA or PGA polymer with a monomer or component, e.g. a carboxylic acid or acid chloride which contains a Cy moiety, or with a monomer or component which contains a moiety which can be further reacted so that it comprises a Cy moiety; or (A9b) the polymer is prepared by a process which includes the step of reacting the terminal carboxyl group of a preformed PLA, PLGA or PGA polymer with a component, e.g. an alcohol, which contains a Cy moiety, or with a component which contains a moiety which can be further reacted, e.g. by transesterification, so that it comprises a Cy moiety. For example, the preformed polymer can be reacted with (i) an alcohol containing a Cy moiety, or (ii) a polyol, for example glycerine, 1,3-propanediol or hexanediol, followed by reaction of one or more of the remaining hydroxyl groups of the polyol with an excess of a carboxylic acid containing a Cy moiety, for example stearic acid or behenic acid; or (A9c) is prepared by a process which includes the step of reacting the terminal hydroxyl group of a preformed PLA, PLGA or PGA polymer with a dicarboxylic acid or anhydride, e.g. succinic anhydride or succinic acid (succinylation); the resulting product, which may have a relatively high molecular weight in which case it may be in the form of a gel, facilitates formulation mixing in-situ, and/or may enable easy mixing of a protein or peptide drug at one pH and release at another pH; or (A9d) is prepared by reacting a preformed PLA, PLGA or PGA polymer with methacrylic anhydride and this reaction mixture is copolymerized with an ethylenically unsaturated monomer containing a Cy moiety; or (A10) contains at least 10%, e.g. 10-40%, by weight of the Cy units.

Other ECC Polymers

A polyol reacted in the presence of lactic acid and glycolic acid forms PLGA sequences with OH end groups at each hydroxyl group of the polyol. These terminal hydroxyl groups can be end capped with a crystalline fatty acid, for example, behenic acid:

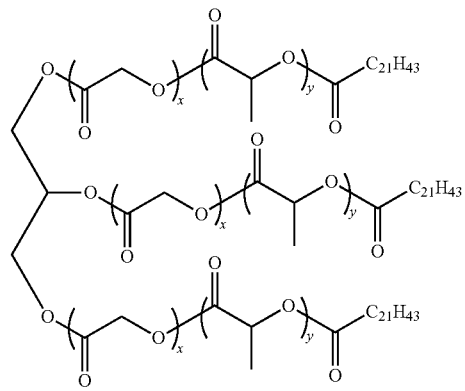

The polymer formed by reaction of a polyol with PLGA monomers (lactic acid+glycolic acid) and end-capping with a crystalline fatty acid gives a fatty acid ester of a hydroxyl PLGA glycerate.

Or, a hydroxyl polycarboxylic acid like citric acid is esterified with a crystalline fatty acid (stearic acid) at the sole remaining hydroxyl group to provide a citric acid stearate. This intermediate is subsequently reacted with lactic acid and glycolic acid to give an acid terminated tri-PLGA citrate which may be end-capped with crystalline fatty alcohol:

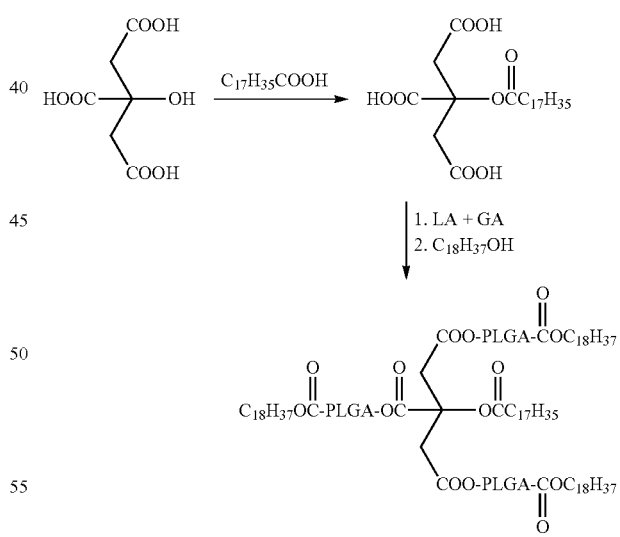

d. End-Cap Crystalline Glycerin Carbonate ECC-PLGA Polyesters:

Glycerin carbonate is easily mixed and reacted with a crystalline fatty acid, for example, stearic acid, to yield a disubstituted hydroxymethyl ethylene glycol diester. This intermediate is then polymerized with lactic acid and glycolic acid or esterified with a preformed PLGA and the larger molecule then optionally end-capped:

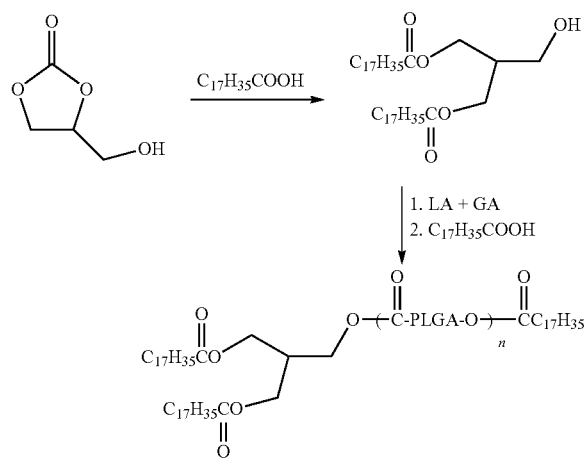

The amount of end capping with fatty acid is dependent on the degree of hydrophobicity and crystallinity desired in the final product. This will be dependent upon the drug which is mixed with the polymer, the drug solubility parameter compared to the polymer solubility parameter and the desired controlled release properties. In general the higher the crystallinity the longer will be the drug release and the slower will be the bioerodibility. Also, the higher crystallinity will exhibit a lower burst effect than a very low amount of crystalline fatty acid end capping.

e. ECC-12-hydroxystearic acid PLGA polyesters:

12-hydroxystearic acid, readily available from castor oil, can be polymerized with lactic acid and glycolic acid and end capped with fatty acid to provide a multi-block PLGA with a hydrophobic center and two end cap crystalline groups for mixing with small molecule insoluble drugs for a slow controlled release drug delivery vehicle:

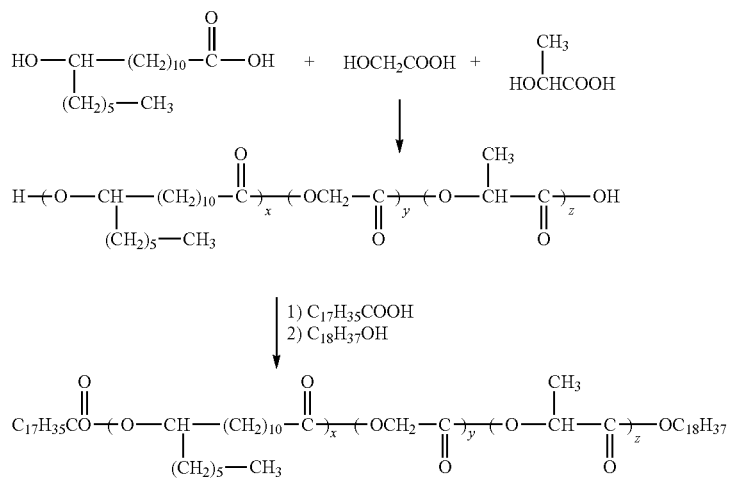

f. Crystalline Fatty Ester Dimethylol Propionic Acid Polyesters:

Dimethylol propionic acid (DMPA) can be esterified with a crystalline fatty alcohol and the resulting crystalline fatty ester polyol reacted with either (a) PLGA components and end-capped with crystalline fatty acid or (b) alkyl functional PLGA to give a novel end cap PLGA with a central and two terminal crystalline, hydrophobic blocks -An A-B-A-B-A block where the A components are hydrophobic and the B component is less hydrophobic and in some cases hydrophilic:

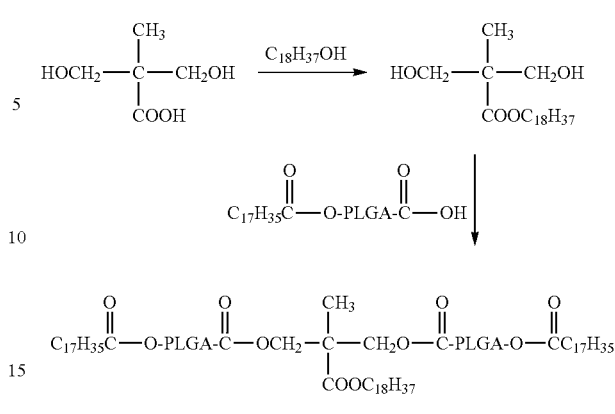

This kind of CYSC polymer by its structure and molecular weight can have different levels of crystallinity—both side chain and end capped to provide easy drug mixing and loading and the desired sustained release properties.

In a similar manner, the preformed polyol may be reacted with lactic acid and glycolic acid to give a crystalline oxazoline PLGA polyester which can be end capped with more crystalline fatty acid if desired:

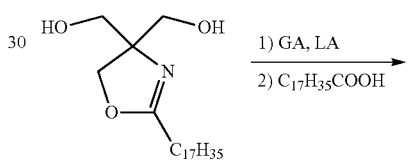

-continued

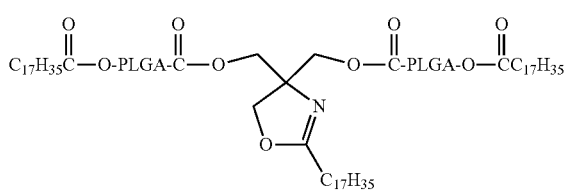

C. Side-Chain Crystalline Hyaluronic Acid:

A dilute hyaluronic acid (HA) solution can transport a CYSC polymer mixed with a drug and suspended in the hyaluronic acid solution as a finely dispersed suspension. If the HA is esterified by reacting one or two free hydroxyl groups on the HA, then a side chain crystalline HA is formed which may function as a drug delivery carrier, the CYSC groups providing a way to regulate dissolution of drug from the normally highly water soluble HA solution:

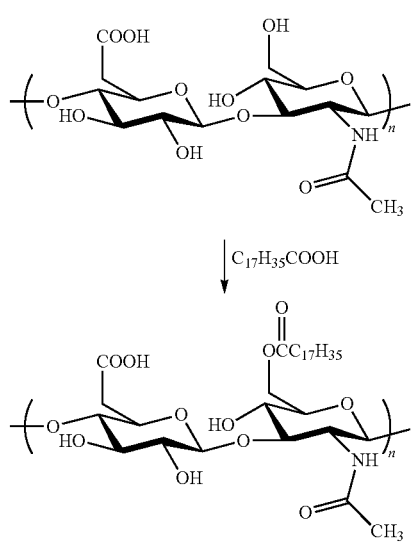

CYC Assemblies

In CYC assemblies, crystalline character is created or enhanced by the non-covalent assembly ("self-assembly") of complementary units in different molecules. Similar self-assembly takes place in nature, for example in peptide architectures and the replication of DNA. The self-assembly can be the result only of non-covalent and non-ionic interaction of complementary units. However, ionic bonding can also be involved. For example an acid-terminated PLGA can be mixed with a crystalline difatty nitrogen amine ($NR_2H$, where R comprises a Cy moiety) to provide an ionic salt which is crystalline as evidenced by DSC but which does not contain a covalent bond.

Any of the CYC carriers can take part in self-assembly, either with another CYC carrier or with another monomer or polymer which includes complementary moieties which will "self assemble" with moieties in the CYC carrier. An entity which is not itself a CYC carrier and which includes the complementary moieties is referred to herein as a "self-assembly additive". Two or more self-assembly additives, neither or none of which is a CYC carrier itself, can form a CYC assembly. The self-assembly results in a product which has a higher ΔH (as compared to the calculated ΔH) and which may have a different Tp than the CYC carrier or the self-assembly additive itself. Because the self-assembly results in a higher ΔH and can result in a higher Tp, the CYC assemblies can make use of components which are similar to the CYC carriers but which do not meet either or both of the requirements that the Tp is at least 0° C. and the ΔH is at least 3 J/g, provided that the CYC assembly does meet those components. The self-assembly can also result in a significant difference in the rate at which a release compound is released from a release composition.

The presence of a self-assembly additive can assist in extending release of a drug or other release material. In many cases, the self-assembly additive will be slowly released from a release composition, for example to be metabolized or excreted by the body.

In one embodiment, the CYC assembly comprises two or more of a CYSC polymer, a CYSC compound and an ECC polymer. The self-assembly can be between the Cy moieties and/or through other complementary moieties, as described below. For example, the CYC assembly can comprise an endcapped PLGA copolymer and a CYSC acrylate polymer. For example in a pharmaceutical formulation, mixing as little as 3% of a CYSC acrylate polymer with an endcapped crystalline PLGA can result in a significantly different release rate.

The complementary moieties in a self-assembly additive can be Cy moieties which self assemble with Cy moieties in the CYC carrier, e.g. n-alkyl moieties containing 14-50, preferably 16-24, e.g. 18 or 22 carbon atoms. Alternatively or additionally, the complementary moieties can be other moieties which self assemble with similar moieties in the CYC carrier, for example polyoxyethylene or other polyoxyalkylene moieties, for example containing, 2-40, 2-20 or 2-10 oxyalkylene moieties. The self-assembly additive can also contain functional groups, e.g. OH, COOH, $CONH_2$ and $CONR_2$. The complementary moieties, and the functional groups if present, can for example be present in alcohols, ethers, acids or derivatives of acids, for example esters or amides. Examples of self-assembly additives include stearic acid, behenic acid, palmitic acid, stearyl alcohol, behenyl alcohol, hexadecyl alcohol, stearamide, N,N,-dimethyl stearamide and the like. Examples of self-assemblies include diblock type structures like polyoxyethylene stearyl alcohol (PEO6 stearyl alcohol) and other block coploymer analogs. For example, a CYC additive (which may also be a CYC carrier) can contain units derived from an amphiphilic monomer and a pegylated or ethyleneoxy-containing side chain (e.g. alkoxypolyoxyethylenemethacrylate where the alkoxy group is C1 to C22 and the number of oxyethylene groups is from 2 to 24) can be blended with a self-assembly additive which is a crystalline alkyl polyoxyethylene alcohol wherein the number of oxyethylene units are from 2 to 40, preferably 2 to 20, and more preferably 2 to 10.

As demonstrated by the Examples below, self-assembly can increase Tp and ΔH by a greater degree than predicted by a simple "rule of mixtures", thus confirming that co-crystallization occurs. It is also possible that self-assembly results in more of the Cy moieties becoming part of crystalline domains. The Examples below also show that the presence of a self-assembly additive can influence the rate of drug release from a pharmaceutical formulation and can also result in a more biodegradable formulation than a formulation composed of the drug and CYSC polymer alone.

For example, a fatty acid, e.g. stearic acid, may be mixed with an end cap fatty crystalline PLA, PGA or PLGA copolymer—to give a crystalline material which has effective capability in the sustained release of a release material in the formulation. For example, a crystalline fatty ether alcohol (e.g. a stearyl polyoxyethylene alcohol containing two moles of EO functionality) can form a non-covalent CYC carrier with enhanced crystallinity when mixed with a crystalline CYSC or end-cap crystalline bioerodable polymer.

Preparation of CYC Carriers

The CYC carriers can be prepared in any way, for example using techniques which are well-known to those skilled in the art. For example, the CYC polymers can be prepared by emulsion, solution, bulk and suspension polymerization techniques using conventional catalysts. Conventional additives and catalysts can be employed to achieve desired molecular weights. For example, in the preparation of CYSC polymers, azo and peroxide catalysts, thiol chain transfer agents (e.g. alkyl mercaptans, hydroxyethyl mercaptan, butyl mercaptopropionate and mercapto acetic acid), or allyl chain transfer agents or regulators (e.g. including alpha-methyl styrene) can be used. The type of polymerisation can often be selected according to the form of CYC release composition to be administered. For example, if a micelle or emulsion form is desired, emulsion polymerisation, optionally in the presence of the release material, can be employed. If a hydrogel is preferred, polymerisation under aqueous or emulsion conditions can be employed. If a spray-dried form is preferred, polymerisation under solvent conditions can be used.

Methods of preparing CYSC graft copolymers include for example preparing a preformed polymer comprising Y(Rc) moieties and optionally Z(Rz) moieties, and then grafting suitable monomers (which may contain Rc and/or Rz moieties) at reactive sites at the end or in the middle of the preformed polymer. Methods of preparing CYSC block copolymers include preparing two or more preformed polymers, at least one of the preformed polymers comprising Y(Rc) moieties and optionally Z(Rz) moieties, and at least one of the other preformed polymer(s) comprising Z(Rz) moieties, each of the preformed polymers having at least one reactive site at an end of, or between the ends of, the preformed polymer, and then reacting the preformed polymers to form the desired polymer.

For example, a CYSC block polymer can be prepared by copolymerising a vinyl type macromonomer with other monomers, or by making a CYSC polymer, and then reacting the functionalized polymer with the second block material, for example a urethane block, or an epoxy block, a polyether block, a polyester block, a polyethyleneoxide, polypropyleneoxide or polytetramethyleneoxide block, a polysiloxane block, or a poly(alkyl or alkoxy)silane block.

Specific Exclusions and Conditions

Certain isolated embodiments of the invention exclude the possibility that the CYC polymer is a CYSC polymer which has one or more of the following characteristics
(1) the polymer is a block co-polymer or a graft co-polymer;
(2) the polymer is a hydrogel;
(3) the polymer is not hydrolytically stable;
(4) the polymer contains moieties derived from a vinyl amide;
(5) the polymer is cross-linked;
(6) the polymer is a thermoplastic elastomer;
(7) the "b" moiety is an anhydride;
(8) the polymer contains 15-20 mol % of methacrylic acid units;
(9) the polymer contains 20-40 mol % of methacrylic acid units;
(10) the polymer contains 15-20 mol % of acrylic acid or alkyl acrylic acid units;
(11) the polymer contains 20-40 mol % of acrylic acid or alkyl acrylic acid units;
(12) the polymer contains side chains containing 18 carbon atoms;
(13) the polymer contains side chains containing 12-18 carbon atoms;
(14) the polymer contains a carbon atom which is directly linked to the Cy moiety and also to a moiety containing a carboxyl or carboxyl salt moiety;
(15) the polymer is in the form of a film;
(16) the polymer is a random copolymer)
(17) the polymer is an elastomer;
(18) the polymer contains a CYC moiety which is attached to the polymer backbone through an anhydride linkage;
(19) the polymer contains a CYC moiety which contains anhydride linkages;
(20) the polymer contains the structure Ra—CO—O—CO—Rb where Ra and Rb may be any moiety;
(21) the polymer does not contain more than 40% of units containing the Cy moieties;
(22) the polymer contains a polybasic acid;
(23) the polymer does not have a pKa greater than 4;
(24) the polymer is used as a gating membrane which is placed between an interior enclosure comprising the drug and an exterior volume into which the drug is to be dispensed;
(25) the polymer is cross-linked or otherwise rendered non-flowable, e.g. by making it part of a block copolymer containing a high melting block, or immobilizing it within a microporous membrane, hollow fiber or fabric mesh;
(26) the polymer is prepared by emulsion polymerization;
(27) the polymer does not contain biodegradable linkages other than ether and ester linkages between repeating units in the polymer backbone, and/or biodegradable linkages other than ester and amide linkages between the polymer backbone and Cy.

Release Materials

Drugs

A wide variety of drugs can be delivered through the use of this invention. The CYC carrier can be associated with one or more hydrophilic or hydrophobic drugs, for example, a small molecule, polypeptide, protein, carbohydrate, polynucleotide, nucleoside, siRNA, immunoglobulin or Fc or Fab fraction thereof, a cyclic compound, alkaloid, beta-lactam, or other antibiotic. The drug may also be an agonist or antagonist of neurotransmitters or hormones, an antipsychotic (for example fluphenazine maleate, chlorpromazine, chlorpromazine hibenzoate, sulpiride, carpipramine hydrochloride, carpipramine maleate, clocapramine hydrochloride, mosapramine hydrochloride, Risperidone (or any compound containing functional groups of benzisoxazole and/or piperidine), clozapine, olanzapine and sertindole and flupenthixole and perphenazine); or an SSRI; or it may comprise cell signalling molecules such as cytokines such as lymphokines, monokines, chemokines, interleukins, prostoglandins etc a statin, a Cox-2 inhibitor, an SSRI, a calcium channel blocker, psychotropic drug, bisphosphonate, anti-proliferative, mitotic inhibitor, angiogenics, antiangiogenics, small molecule such as rapamycin or derivatives, antipain medications, anti-inflammatories, hormones, anti-osteoporosis drugs, cytotoxic agents, chemotherapeutics and contraceptives.

Specific drugs and drug classes include the following, and precursors and pharmacologically active derivatives, congeners, and metabolites thereof:—risperidone, olanzapine, atorvastatin, celecoxib, omeprazole, esomeprazole, quetiapine, metoprolol, budesonide, ibuprofen, uracils (eg., 5-fluorouracil), steroids and esters of steroids or other hormones (e.g., estrogen, progesterone, testosterone, androsterone, cholesterol, norethinidrone, digoxigenin, cholic acid, deoxycholic acid, and chenodeoxycholic acid), boron containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, kedarcidin chromophore), heavy metal complexes (e.g., cisplatin, carboplatin), hormone antagonists (e.g., tamoxifen), non-specific (non-antibody) proteins (e.g., sugar oligomers, insulin), polynucleotodes and oligonucleotides (e.g., mRNA sequence), radio-nuclides, toxins (e.g., ricin, and transcription based pharmaceuticals. In certain embodiments the drug may be or may contain bacterial toxins such as botulinum toxin ("botox").

The table below gives a selection of some drugs that can be incorporated into and delivered by the pharmaceutical formulations of the invention.

| Name | Trade Name | Drug Class | $M_r$/Da | Hydrophobic |
|---|---|---|---|---|
| Atorvastatin | Lipitor | Statin | 1,209 | YES |
| Symvastin | Zocor | Statin | 418 | YES |
| Celecoxib | Celebrex | Cox-2 inhibitor | 381 | YES |
| Sertradine | Zoloft | SSRI | 343 | YES |
| Omeprazole | Losec/Prilosec | PPI | 345 | YES |
| Esomeprazole | Nexium (isomer of Prilosec) | PPI | 767 | YES |
| risperidone | olanzapine atorvastatin | celecoxib | omeprazole | esomeprazole |
| Azithromycin | Zithromax | Antibiotic | 749 | NO |
| Quetiapine | Seroquel | SSRI | 883 | YES |
| Metoprolol | Seloken/Toprol | Beta-blocker | 653 | NO |
| Budesonide | Pulmicort/Rhinocort | Anti-inflammatory-steroid | 431 | YES |
| Clarithromycin | Biaxin | Antibiotic | 748 | YES |
| Paroxetine | Paxil | SSRI | 375 | NO |
| Oxycodone | Oxycontin | Opioid agonist | 351 | NO |
| Risperidone | Risperdal | Psychotrope | 410 | YES |
| Alendronate | Fosamax | bisphosphonate | 325 | NO |
| Venlafaxine | Effexor | SSRI | 314 | NO |
| Amlodipine | Norvasc | Ca-channel-blocker | 567 | YES |
| Olanzapine | Zyprexa | | 312 | YES |
| Lansoprazole | Prevacid | PPI | 369 | YES |
| Fluoxetine | Prozac | SSRI | 345 | NO |
| Finasteride | Proscar | steroid-antagonist | 372 | YES |
| Sildenafil | Viagra | PDE5-antagonist | 667 | NO |
| Rosuvastatin | Crestor | Statin | 1001 | YES |

The drugs that can be used include chemotherapeutic agents used to kill neoplastic cells, for example (1) Alkylating agents, which destroy the cancer cell's DNA e.g., Busulfan, Cyclophoshamide and Melphalan, (2) Nitrosoureas, that inhibit a cancer cell's enzymes needed for DNA repair, e.g., Carmustine and Lomustine, (3) Anti-metabolites, that interfere with both a cancer cell's DNA and RNA, e.g., 5-Fluorouracil, Methotrexate and Fludarabine, (4) Anti-tumor antibiotics that interfere with a cancer cell's DNA in addition to changing its cellular membrane, e.g., Bleomycin, Doxorubicin and Idarubicin, (5) Mitotic Inhibitors, that inhibit enzymes needed for protein synthesis in the cancer cell, e.g. Docetaxel, Etoposide, Vincristine and Vinblastine and Vinorelbine, and (6) Radioactive isotopes, which destroy cancer cells by the production of radioactive emissions, e.g., indium-111 ($^{111}$In), yttrium-90 ($^{90}$Y).

The drugs that can be used for sustained release applications include, for example, anti-pain medications (e.g. morphine analogues), anti-psychotics (e.g. risperidone), anti-inflammatories (e.g. steroids or NSAIDs such as Budesonide), hormones (e.g. testosterone or progesterone) cholesterol lowering drugs (e.g., statins), osteoporosis drugs (biphosphonates), anti-angeogenics (e.g., anti-VEGF) and contraceptives. The drugs they can be used include the derivatives (defined herein as including, but not limited to any pharmacologically active metabolite, or analogue, agonist, derivative, variant, congener, or isomeric form) of any drug described herein.

Ligand-Targeted Polymeric Drug Delivery

In certain embodiments, the CYC carrier incorporates ligands that bind specifically to target receptor molecules. Target receptor molecules are present on the surface of a specific type of target cell, such as a cancer cell. The ligands may be incorporated into the polymer formulation by copolymerization of a comonomer which carries a receptor covalently attached to the monomer. Alternatively a ligand may be incorporated into the pharmaceutical formulations of the invention by any other means which does not involve covalent bonds and which allows the ligand to associate with the polymer, either as a simple physical mixture, or by ionic bonds, hydrogen bonds, Van der Waal's forces or hydrophobic/hydtrophilic interactions. The ligands bind specifically to molecules expressed on the cell surface of a target e.g., receptor proteins that are differentially over-expressed on target cells, for example cancerous cells.

For example, many types of cells express a large number of folate receptors on their cell surface, more so than for non-cancerous cells. Folic acid or derivatives or portions of folate can be physically mixed into the pharmaceutical formulation during its preparation, or added to the outside of particles formed after crystallization or precipitation of the formulation. The folate molecules bind specifically with the folate receptors on a target cancer cell. A chemotherapeutic agent, for example carboplatin or cis-platin or taxol, can be mixed with or bound by hydrogen bonding or otherwise to the CYC carrier, so that it can thereafter be delivered to a specific cell target. Thus, in some embodiments, the formulation comprises, a slightly basic/neutral CYSC polymer derived from a mixture of a SCC monomer, hydroxyethyl methacrylate and dimethylaminoethyl methacrylate and a drug, for example, an anti-cancer drug, e.g. methotrexate. In one such embodiment, during preparation of the formulation, folic acid is mixed with the CYSC polymer and the drug or added to the formulation after isolation of the formulation, so as to concentrate folic acid at the surface of the drug formulation particles. Upon exposure to an external heat stimulus, the encapsulated or bound drug, e.g. methotrexate, is released as the CYC carrier transitions from a crystalline to an amorphous structure. Alternatively, release of the drug may be stimulated by means other than heat, e.g. by one or more of hydration, swelling, osmotic expulsion and by increasing the permeability of the polymer.

This ligand-targeted polymeric drug delivery system can be used to deliver known targeted cancer therapy agents. For example, small-molecule drugs can be used to block specific enzymes and growth factor receptors (GFRs) involved in cancer cell growth. These drugs act as signal-transduction inhibitors. One such drug that may be used with the invention is Gleevec® (STI-571 or imatinib mesylate) to treat gastrointestinal stromal tumours and certain kinds of chronic myeloid leukemia. Another drug that may be used is Iressa® (ZD1839) that is used to treat advanced non-small cell lung cancer. This drug targets the epidermal growth factor receptor (EGFR), which is overproduced by many types of cancer cells.

Apoptosis-inducing drugs may also be incorporated. One such drug is Velcade® used to treat multiple myeloma. Velcade blocks proteasomes, which help to regulate cell function and growth. Other apoptosis-inducing drugs include Genasense™ to treat leukemia, non-Hodgkin's lymphoma, and solid tumours. Genasense blocks the production of BCL-2, which promotes the survival of tumor cells.

Other possible drugs include monoclonal antibodies that bind to growth factor receptors, such as Herceptin® (Trastuzumab).

A number of other tumor-specific targets are discussed below. Many of the ligands describe below are either small proteins (about 30-50 amino acid residues) or have a small active site of only a few residues (often 3-7 amino acids) and can be attached to the CYC carriers used in this invention, for example covalently.

The epidermal growth factor receptor (EGFR) is over-expressed in the majority of colorectal cancers. Also expressed in the gut are gastrointestinal (GI) peptide hormones, such as gastrin, CCK, secretin, glucagon, somatostatin, and their cognate G protein-coupled receptors (GPCRs). EGFR, GI hormones or any related proteins may be used as specific targets by providing a release composition with a ligand, such as a specific antibody, that binds specifically to EGRF or GI hormones or homologous proteins or portions thereof. A number of leukemias and lymphomas, including cutaneous T-cell lymphoma, chronic lymphocytic leukemia, and B-cell non-Hodgkin's lymphoma, express the interleukin-2 receptor (IL-2R) receptor. Antibodies or other ligands (e.g., DAB389IL-2, ONTAK™; Seragen Inc, San Diego, Calif.) targeting the interleukin-2 receptor may be used to target a polymer-drug formulation of the invention. Monoclonal antibodies directed against CD33, a cell surface antigen highly expressed in acute promyelocytic leukemia (APL) may be used as a targeting ligand in the present invention against APL tumor cells.

Rituximab is an anti-cancer monoclonal antibody that binds to CD20 which is expressed on the surface of malignant B cells. Rituximab may be used as a targeting ligand in the present invention.

Antibodies and other ligands that bind OPG or RANKL can be used as targeting ligands in the present invention against multiple myeloma tumor cells.

The expression patterns of folate receptor (FR) isoforms, alpha and beta, in normal and malignant male and female reproductive tissues are well studied. Folate, analogues of folate and other ligands that bind to folate receptors can be incorporated into the pharmaceutical formulations of the invention to provide specific and/or preferential targeting of various tumor tissues.

Prostate-specific membrane antigen (PSMA) is a metallopeptidase expressed predominantly in prostate cancer (PCa) cells. Ligands that bind to PSMA can be incorporated into the pharmaceutical formulations of the invention to provide specific and/or preferential targeting of prostate tumor tissue.

Two protein hormones having activities that are similar to insulin are termed insulin-like growth factor I (IGF-I) and IGF-II. In parallel, there are two receptors, the insulin-like growth factor 1 receptor (IGF1R) and IGF2R that bind with differing affinities to insulin, IGF-I, and IGF-II. IGF2R acts as a cell surface receptor for many proteins relevant to breast cancer biology, including IGF-II. IGF2R could be targeted using sugar moieties and/or polysaccharides attached to the CYC carriers used in this invention.

Ovarian cancer G protein coupled receptor 1 (OGR1) and GPR4, two structurally related receptors are high affinity molecular targets for SPC. Such receptors for phospholipids on tumors would be ideal targets for polymers as used by the invention coupled to lysophosphatidic acid (LPA), sphingosylphosphorylcholine (SPC), and/or phosphatidic acid (PA). Ligands such as phospholipids that bind to these targets may be incorporated into the pharmaceutical formulations of the invention to provide specific and/or preferential targeting of ovarian and other tumor tissue.

Another specific target molecule is fibroblast growth factor (FGF). Activated FGF initiates a kinase cascade resulting in phosphorylation of docking protein fibroblast growth factor receptor substrate 2 (FRS2α). Anti-FGF antibodies or portions of FRS2 domains may serve as ligands for targeting tumors. Programmed death receptor ligand 1 (PD-L1) is abundant on many cancers. Ligands that bind to PD-L1, such as antibodies or IFN-gamma or related molecules could provide specific and/or preferential targeting of cancer cells and tissues.

The glycolipid-anchored receptor for urokinase-type plasminogen activator (uPA) is overexpressed at the invasive tumor-stromal microenvironment in many human cancers. Ligands that bind to uPA, such as antibodies could be incorporated into the formulations of the invention to provide specific and/or preferential targeting of cancer cells.

CXCR4 is a seven-span transmembrane protein that is a native receptor for the alpha-chemokine stromal-derived factor-1 (SDF-1) that is expressed on the surface of cancer stem cells. The SDF-1-CXCR4 axis is also involved in directing their trafficking/metastasis to organs that highly express SDF-1 (e.g., lymph nodes, lungs, liver, and bones). A region of SDF-1 homologous to the receptor-interacting region could be incorporated into the pharmaceutical formulations of the invention to provide specific targeting to cancer cells, particularly to treat or prevent metastasis of tumor cells.

Notch signalling contributes to pre-malignant metaplastic changes that precede pancreatic carcinoma, and it is also likely to be involved in other forms of metaplasia. The Notch receptor ligand can be incorporated into the pharmaceutical formulations of the invention to provide specific targeting to pancreatic carcinoma and other cancer cells.

Additionally, other types of ligands may be incorporated into the formulation of the invention including ligands that recognize Receptor Protein Kinases, G-Protein Coupled Receptors, Nuclear Receptors, Ligand-Gated Receptor Ion Channels, Macrophage Scavenger Receptors, T-Cell Receptors, Netrin Receptors, VPS10 Domain Containing Receptors, Tetraspan Family Proteins, Ion Channels, ABC Transporters, Semaphorins and Neuropilins, Membrane Proteins Associated with Intercellular Communication and Peripheral and Anchored Membrane Proteins.

In many of the above cases, the ligand may be an antibody or portion of an antibody (such as the Fab portion or fragment thereof) that binds specifically to the cancer-associated target molecule. Antibodies may be polyclonal or monoclonal and often may be humanized. Such antibodies can be produced by standard well-known methods. Monoclonal antibodies (MAb's) that bind specifically to tumor-associated antigens have been employed in an attempt to target toxin, radionucleotide, and chemotherapeutic conjugates to tumors. To date, a variety of monoclonal antibodies have been developed that induce cytolytic activity against tumor cells. For example, a humanized version of the monoclonal antibody MuMAb4D5, directed to the extracellular domain of P185, growth factor receptor (HER2), is used to treat human breast cancer. Also, a chimeric antibody against CD20, which causes rapid depletion of peripheral B cells, including those associated with lymphoma, is used to treat low-grade B-cell non-Hodgkin's lymphoma. Other humanized and chimeric antibodies under development or in clinical trials include an anti-CD33 antibody that binds to CD-33, which is expressed on most types of myeloid leukemic cells. Another is a chimeric antibody against the leukocyte antigen CD-45 (cHuLym3). The present formulations of the invention may incorporate any target-specific ligands of any kind, including the antibodies and ligands mentioned herein, and any derivatives and homologues thereof.

The pharmaceutical formulations of the present invention optionally have one or more of the following characteristics:—
(1) The formulation, in vivo, when implanted within a human subject, continuously releases a therapeutically effective dose of drug to the subject over a period of at least 30 days.
(2) The formulation, in vivo, when implanted within a human subject, continuously releases between 0.1 milligram and 100 milligrams of drug per day over a period between 12 hours and 30 days following implantation.
(3) The formulation, in vitro (elution into 1 L phosphate buffered saline (PBS) the PBS being at a pH of about 7.4, at 37° C., stirred at 100 rpm, or in one of the test procedures described in the Examples below, (i) has an average rate of release of drug from the formulation which is no greater than 20 milligrams per day averaged over any 24 hour period during the first 168 hours of elution, and/or (ii) continuously releases between 0.1 milligram and 20 milligrams per day, averaged over any 24 hour period, over a period of at least 30 days, and/or (iii) releases no more than 20% by weight of drug over a period of 24 hours, and/or (iv) releases the drug at an average rate no greater than 25 milligrams per day averaged over any 24 hour period during a period from 12 hours to 168 hours following inception of elution.
(4) The formulation is adapted for oral delivery and the drug has not more than 5, preferably not more than 10, hydrogen bond donors.
(5) The formulation is adapted for oral delivery and the drug has a molecular weight under 500 g/mol.
(6) The formulation is adapted for oral delivery and the drug has a LogP (partition coefficient) under 5
(7) The formulation, in vivo, when implanted subcutaneously or intramuscularly within a human subject, continuously releases a therapeutically effective dose of the drug to the subject over a period of at least 30 days.

Specific Embodiments of Pharmaceutical Formulations

One specific example of a formulation containing the psychoactive (antipsychotic) agent Risperidone, (4-[2-[4-(6-fluorobenzo[d]isoxazol-3-yl)-1-piperidyl]ethyl]-3-methyl-2,6-diazabicyclo[4.4.0]deca-1,3-dien-5-one) is the following. Risperidone may be physically mixed with a CYSC polymer or other CYC carrier, either directly, or after it has been pre-associated, for example with a surfactant, PEG, human (or bovine etc) serum albumin, or with proteins etc. to provide immunological shielding, increased half-life, and improved bioavailability. The formulation may be formed into a shaped solid implant suitable for introduction, e.g. by trocar, under the skin or intramuscularly or by injection above the formulation's melting temperature. It is believed that a dose of Risperidone of about 4 mg/day is sufficient to prevent psychotic episodes in many patients. Individual variations in tolerance and effectiveness, however, can be wide. Therefore the current invention may be formulated to supply from 1 to 60 mg/day over a period of 1 to 200 days. The advantage of an implanted dosage form is increased compliance, which with psychosis, is a major issue. In one embodiment, at least 50 mg of Risperidone is formulated into a single implantable dosage form by mixing the drug in powdered form with a CYSC polymer at a temperature above the Tm of the polymer, for example at between 42° C. and 60° C. in some cases, no solvent is required. In other cases, a solvent is used to improve compatibility and is subsequently removed. The mixture is cooled and shaped into, for example, solid elongated or approximately spherical implants. In other embodiments, the amount of Risperidone formulated into a single implantable dosage form may be at least 100 mg, or at least 200 mg, or at least 500 mg, or at least 1000 mg, or at least 1500 mg, or at least 2000 mg. In some dosage forms, the total amount of drug may be up to 3, 4 or 5 grams. The Risperidone implant is introduced subcutaneously into a subject using a trocar or minor incision. The implant releases Risperidone at an average rate of between 1 and 60 mg (for example no more than 1, 2, 3, 4, 5, 7, 10, 20, 40, 80, 120, 200, or 300 mg) per day over a period of at least 5, 10, 15, 20, 25, 30, 40, 60 or 90 days. In one exemplary embodiment the implant releases Risperidone at an average rate of between 4 and 12 mg per day over a period of at least 7 days. During this period, a desired therapeutic effect is provided for at least 75% of the time. The implant is then removed, or may be left in to erode over time. If a larger bolus of drug is desired, the local area of skin above the implant may be heated by any convenient means.

In other embodiments the implant releases Risperidone at an average rate of between 1 and 20 mg per day, or 3 and 100 mg per day or 4 and 30 mg per day over a period of at least 7 days or at least 14, 21, 30, 45, 60 or 90 days. The Risperidone is delivered in such a manner and rate that the blood plasma level of risperidone is within the human therapeutic window, 1 to 125 ng/ml over the period of 30 or 60 or 90 days.

In certain related embodiments, Risperidone may be pre-associated with a surfactant, PEG, human serum albumin or with proteins. In another embodiment, the CYSC polymer comprises side chains having an average length of, for example, between 6 and 50 monomer units. In another embodiment, the CYSC polymer has side chains with an average length of between about 12 and 50 alkyl ester acrylate or methacrylate monomer units.

In certain embodiments, Risperidone is physically mixed with the polymer and no covalent or ionic bonds are formed between the drug and the polymer. In some embodiments, the drug associates with the polymer via hydrogen bonds and/or van der Waals forces. In various alternative embodiments Risperidone is associated with the CYSC polymer by electrostatic bonds, by hydrogen bonds, van der Waals forces or a combination of one or more of these effects. This exemplary embodiment may be applied to any number of drugs.

In another embodiment designed to release a drug to control pain, the drug of the formulation may be an opioid, opioid antagonist, synthetic opioid, morphine, fentanyl or sufentanyl, or any type of local or systemic analgesic acting on peripheral or central nervous pair receptors. In such embodiments, the polymer may be implanted under the skin such that the drug is released over a period of time to treat pain for a number of hours such as at least 3, at least 6 or at least 12 hours. The formulation may also be an oral formulation, transdermal formulation or depot.

In some embodiments, the formulation is part of a transdermal drug delivery device such as a patch, wherein the drug, mixed into the CYSC polymer, is released from a patch placed against the skin. The formulation may be made to release the drug steadily or increasingly or decreasingly over a period of time, or may be made to release drug in intermittent boluses in response to a stimulus such as heat. For sustained delivery a drug will not be released immediately as a bolus but will be released from the polymer over time in a generally sigmoid pattern, providing a desired therapeutic delivery, e.g. to treat pain over a desired time, such as over at least 1, at least 3, at least 6 or at least 12, 24, 36, or 48 hours. In other embodiments, the drug may be delivered with approximately first order or zero order kinetics, over at least a certain desired time (e.g., over at least 1, at least 3, at least 6, or at least 12, 24, 36 or 72 hours). In such embodiments, the drug is released from the polymer, and the polymer is not transported across the skin.

The release of drug may be induced or increased by the application of heat to the device. The device may be heated by a separate heating device or by an integral heating unit. The amount of drug released from the formulation will depend on the duration of heating and the temperature of the device. Heat-induced drug release may be controlled by the physician, either directly or remotely, or by the patient. This provides controlled self-administration of drug to treat pain and other conditions when needed. The drug released from the formulation may be released onto the surface of the skin, and will then penetrate the skin by various means. Generally transdermal delivery relies on passive diffusion across skin membranes, but penetration may also be improved by using solvents or enhancers such as water, ethanol (EtOH) and l-menthol (LM) that modify the properties of the outermost layers of the skin, or on the use of electrical or thermal technologies to "push" drugs through the skin. Any such means may be used in the present invention, either mixed with the polymer or separate from the polymer. Delivery rates of an opioid such as fentanyl may for example range from about 1.0 to 1000 ng/cm$^2$/hr following application of a transdermal patch.

A transdermal formulation may be made by mixing the CYSC polymer and drug, optionally with an adhesive component, and retaining the formulation produced in or on a flexible film to produce a patch. The flexible impermeable film forms the backing of the patch, and the formulation side to be applied to the skin may be covered with a removable cover, which is removed prior to application to the skin. The formulation side includes at least some adhesive portion, generally on the periphery of the patch so that when applied, the patch forms a seal against the skin, isolating the formulation from the environment. Such embodiments exclude "gating" devices wherein a drug is maintained in a reservoir and is separated from the skin by a polymer membrane the permeability of which may be altered to allow drug delivery. The present invention does not include a drug reservoir separated from the skin by a polymer film. In the present invention, the drug is integrally mixed together with the CYSC polymer to form a drug-polymer formulation. Heat may be produced by chemical or electrical means, or even by physical means such as rubbing with the hand to produce friction-induced heat. The heating element may be functionally linked to a control (lock-out) element that prevents activation without permission, such as by use of a radio frequency signal to control the activation of an electrical heat-generating circuit.

TABLE 3

Polymer-Drug Formulations.

| Polymer | I | II | III | IV | V | VI | VII | VIII | IX | X |
|---|---|---|---|---|---|---|---|---|---|---|
| Atorvastatin | N | H | H | I | I | I | I | N | N | H |
| Symvastatin | N | H | H | N | N | N | N | H | H | H |
| Celecoxib | N | H | H | H | H | H | H | N | N | N |
| Sertraline | N | I | I | N | N | H | H | N | N | N |
| Omeprazole | N | I | I | H | H | H | H | N | N | N |
| Esomeprazole | N | I | I | H | H | H | H | N | N | N |
| Pravastatin | N | H | H | I | I | I | I | N | N | H |
| Azithromycin | N | I | I | N | N | H | H | N | N | N |
| Quetiapine | N | I | I | N | N | H | H | N | N | N |
| Metoprolol | N | I | I | N | N | H | H | N | N | N |
| Budesonide | N | H | H | N | N | N | N | H | H | H |
| Clarithromycin | N | I | I | N | N | H | H | N | N | N |
| Paroxetine | N | I | I | N | N | H | H | N | N | N |
| Oxycodone | N | I | I | N | N | H | H | N | N | N |
| Risperidone | N | I | I | N | N | H | H | N | N | N |
| Alendronate | N | I | I | N | N | H | H | N | N | N |
| Venlafaxine | N | I | I | N | N | H | H | N | N | N |
| Amlodipine | N | I | I | N | N | H | H | N | N | N |
| Olanzapine | N | I | I | N | N | H | H | N | N | N |
| Lansoprazole | N | I | I | N | N | H | H | N | N | N |
| Fluoxetine | N | I | I | N | N | H | H | N | N | N |
| Finasteride | N | H | H | H | H | H | H | N | N | H |
| Sildenafil | N | I | I | N | N | H | H | N | N | N |
| Rosuvastatin | N | H | H | I | I | I | I | N | N | H |
| Methotrexate | N | I | I | I | I | I | I | N | N | H |
| Doxyrubicin | N | I | I | I | I | I | I | N | N | H |
| Nicotine | N | I | I | N | N | H | H | N | N | N |
| Fentanyl | N | I | I | N | N | H | H | N | N | N |
| Paclitaxel | N | H | H | H | H | H | H | N | N | H |
| Cis-platin | N | L | L | L | L | L | L | N | N | N |
| Fluorouracil | N | I | I | H | H | H | H | N | N | N |
| Ibuprofen | N | H | H | I | I | I | I | N | N | H |
| Aspirin | N | H | H | I | I | I | I | N | N | H |
| Dexamethasone | N | H | H | H | H | H | H | N | N | H |
| Leuprolide | N | I | I | I | I | I | I | N | N | H |

(N = neutral polymer-drug interaction; H = hydrogen bonded polymer-drug interaction; I = ionic polymer-drug attachment; L = ligand attached polymer-drug interaction)

Release Compositions, Methods of Making Release Compositions and Methods of Delivering Release Materials The release compositions of the invention comprise a CYC carrier and a release material associated therewith. In some embodiments, the release material is dissolved in the CYC carrier, thus forming a single phase. In other embodiments, the release material is uniformly or non-uniformly distributed as a separate phase in the CYC carrier, for example as a dispersion or emulsion. In some embodiments, the release composition is a single phase composition. In other embodiments, the release composition comprises at least two phases, for example comprising a matrix in which the CYC carrier and release material are uniformly or non-uniformly distributed as a separate phase (which, as indicated above, can comprise a solution of the release material in the CYC carrier or a uniform or non-uniform distribution of the release material as a separate phase in the CYC carrier).

The Tp of a release composition can be the same as the Tp of the CYC carrier, but is more often somewhat lower than the Tp of the CYC carrier. The Tp of a release composition can for example be 22-70, 35-50, 38-50, 37-42, or 40-47° C., or at least 37° C.

The composition can contain any appropriate proportion of the release material, depending on the intended use of the composition. In some embodiments, the weight of the drug or other release material, based on weight of the composition is at least 1%, at least 2%, at least 5%, at least 7%, at least 8%, at least 10%, at least 15%, at least 17%, at least 20%, at least 25%, at least 30%, at least 35%, at least 40%, at least 45%, at least 50%, at least 55%, at least 60%, or at least 70%, e.g. 1-20%, 5-30%, 10-30%, 20-30%, 10-50%, or 20-50%. In other embodiments, the composition contains 0.1-5%, for example up to 2%, up to 3%, or up to 4%, of the release material. High drug loading is particularly useful for sustained release formulations. In some embodiments, the present invention combines high drug loading with reduced burst effect.

The CYC carrier should be selected having regard to the nature of the release material, the way in which the release composition is to be applied to the target site, and the way in which the release material is to be released. For example, in the case of a pharmaceutical formulation, the drug may be delivered as an oral tablet or capsule, as a parenteral subcutaneous injection or intravenous infusion, as a transdermal patch application, as an implant which may later be explanted, as a rectal administration, by pulmonary techniques or as a drug-eluting coating on a medical device, e.g. a drug-eluting stent. Dependent on the application, the release composition may most appropriately be in the form of a solid, a solution, a coating, a particle (e.g. a microparticle or nanoparticle), an emulsion or a suspension.

A simple form of association is a solution of the release material in the CYC carrier. In that case, for example when the solution is a pharmaceutical formulation which is injected, the presence of the carrier will delay only slightly the delivery of the release material, for example the absorption of the drug in vivo. More often, a pharmaceutical formulation is a dispersion, an emulsion or a suspension in which particles comprising the drug and the CYC carrier are uniformly distributed in an aqueous medium.

In some embodiments, the release composition comprises a colloidal dispersion of particles having a size of 1 nm to 0.5 mm. Such a dispersion can be produced by mixing or sonication or homogenization of an aqueous mixture of the drug and polymer matrix in the presence of a surfactant. The drug and/or the CYC carrier may be dissolved in a solvent which evaporates during the sonication or homogenization process. This process can lead to microparticles having a size of from 0.1 to 1000 microns. These colloidal and emulsion mixtures may be suitable for a variety of applications. For example, microsphere particles have a diameter of 0.1-150, e.g. about 50, μm, suspended in suitable aqueous vehicles may be injected through a conventional syringe using an 18-20 gauge needle. The particle sizes can be measured using a Horiba particle size analyzer LA 910.

The type of drug may influence the processing conditions. For example, some drugs, e.g. proteins, are likely to be adversely affected by conventional emulsification used for microsphere production. This invention can make use of techniques to disperse proteins gently in a polymer solution and atomizing this mixture into liquid nitrogen with extraction of the frozen solvent for the polymer, thus producing stable protein microspheres which are suitable for suspension and injection. This invention can also make use of non-aqueous formulation which maintain protein activity and conformation.

In one method for making compositions comprising a CYC carrier and a release material, the CYC carrier is melted, and the drug or other release material is mixed with the CYC carrier, the mixing being carried out at a temperature which is above the To, usually above the Tp, of the CYC carrier. During such mixing, other desired ingredients, e.g. fillers, excipients, dyes, colorings, flavors, disintegrators, stabilizers, can be added. The mixing can optionally be carried out in the presence of another material which is liquid at the mixing temperature and which is not a CYC carrier. This method can result in a uniform mixture which can, if desired, be suspended above the melting point of the mixture in a non-solvent, thus producing, upon cooling, solidification of the release composition as particles. The particles can be washed and filtered, and, for example, suspended in a liquid carrier, e.g. to produce an injectible solution. In another embodiment, in which no solvent is preferably used, the molten mixture, or the solidified mass obtained by cooling the molten mixture, can be processed into desired shapes, e.g. into rods, ovals, and tablets, using known procedures.

Because the CYC carrier can have a relatively low melting point, the ability to carry out mixing at relatively low temperatures is particularly valuable when the release material is a drug, e.g. a peptide or protein drug, or other release material which is damaged (e.g. denatured or partially or completely inactivated) by exposure to a temperature which is more than 15° C., or more than 30° C., above the Tp of the CYC carrier, for example more than 50° C. or more than 65° C. The CYC carrier used in such methods may for example have a Tp about (or alternatively not more than) 30° C., 35° C., 37° C., 40° C., 42° C., 45° C., 50° C., 55° C., 60° C., 65° C., 70° C., 75° C. or 80° C., for example 35-65° C., 40-65° C., 45-60° C., 40-60° C., 50-65° C. For drug delivery, it is generally desirable that the pharmaceutical formulation should have a Tp above the body temperature of the subject (e.g. 37° C. However, in some embodiments, the pharmaceutical formulation has a Tp below 37° C., so that the formulation, after being implanted, maintains a non-solid consistency.

In another embodiment, microparticles are prepared by dissolving a CYC carrier in a solvent, dispersing a solid or liquid drug or other release material into the solution, and dispersing the mixture rapidly into cold water or spray in the mixture into a chamber, thus forming microspheres or microcapsules.

Another method of making microparticles is the water/oil/water double emulsion method. An aqueous phase containing the release material, e.g. drug, for example a protein, is dispersed into an oil phase comprising the CYC carrier dissolved in an organic solvent under high speed homogenization conditions. The resulting water-in-oil emulsion is then dispersed in an aqueous solution containing a polymeric surfactant such as a polyvinyl alcohol and further homogenized to produce a water/oil/water emulsion. The emulsion is stirred for several hours to evaporate the solvent, and the resulting nanoparticles or microparticles are collected by filtration.

In another embodiment, a CYC polymer is prepared as an emulsion copolymer using emulsion polymerization techniques, optionally in the presence of small amounts of co-solvent. The release material can then be added in a compatible solvent for the emulsion, thus allowing migration of drug into the emulsion polymer particles.

Peptide and Protein Drug Delivery

Some of the CYC carriers are particularly well suited for the delivery of protein and peptide drugs, including but not limited to, hormones (such as growth hormones and sex hormones), LHRH, insulin, calcitonin, secreted proteins, alpha-glucosidase, interferons, erythropoietin, antibody drug conjugates, Fc fusion proteins, interferon, anti-CD 20 therapeutics, Factor VII, IX or X, monoclonal antibodies, cytokines, kemokines, cell cycle regulators, BSA protein, and transcriptional modulators.

Protein and peptide drugs are large hydrolytically unstable molecules and are often adversely affected by temperature (typically temperatures above about 60° C.), pH, acids, enzymes and ionic groupings of time found in the cationic and anionic surfactants which are often used in drug formulations of small drug molecules). Consequently, they are typically administered by subcutaneous injection or intravenous (IV) infusion. It is, therefore, desirable to be able to deliver protein and peptide drugs by other means, for example oral administration, and/or to prolong their release after delivery, thereby reducing the number of injections required for administration. We have found that the problems associated with the present methods of delivering protein and peptide drugs can be mitigated through the use of selected CYC carriers. Examples of such CYC carriers are:—
  (1) CYC carriers comprising block copolymers comprising CYSC acrylate blocks and end-capped crystalline PLGA blocks, obtained for example by grafting an end-capped PLGA (ECC PLGA) to a CYSC acrylate), and
  (2) CYC assemblies of CYSC acrylates and/or ECC PLGA's, optionally with another Cy-containing material, for example a crystalline fatty acid, a crystalline fatty alcohol, or a crystalline fatty ethoxylate alcohol.

Use of a CYC carrier can provide:—
a) Improved loading capability. The CYC carriers, in particular the amphiphilic CYSC acrylates and ECC-PLGAs, can be designed to be compatible on mixing with selected release materials, for example peptides and proteins, and other drugs. As a result, high loading can, if desired, be obtained. For example, Cy-containing monomers can be copolymerized with other monomers to provide amphiphilic polymers which are compatible with a selected peptide or protein. Similarly, the ECC-PLGAs can be prepared so that they contain different proportions of units derived from lactic acid and/or glycolic acid (and/or other monomers which can be polymerized to polyesters) in the polymer backbone of the PLGA or other polyester, and the amount of crystalline end capping can be varied, in order to achieve desired amphiphilic properties, resulting for example in a change in the compatibility, e.g. solubility, of the release material and the CYC carrier.
b) Improved mixing capability. Unlike the polymers presently used, e.g. polyethylene-co-vinyl acetate (EVA) and PLGA, which must have high molecular weights in order to provide acceptable delivery rates, the CYC carriers can have relatively low molecular weights and relatively low melting points. The CYC carriers can also contain hydrophilic moieties which assist mixing with the peptide or protein drug. It is often possible, therefore, to mix a CYC carrier with a release material at relatively low temperatures, for example below 75° C., particularly below 60° C. This is particularly desirable when the release material is adversely affected by higher temperatures. CYC carriers can, therefore, be mixed easily with protein and peptide drugs at relatively low temperatures which do not degrade the drug.
c) Improved stability. The presence of the hydrophobic Cy moieties in a CYC carrier enables protein and peptide drugs to be protected from aqueous body fluids, thus preventing bioerosion of the peptide or protein.
d) Repeatable and controllable delivery of drugs, including protein and peptide drugs, with reduced burst, because a stable and uniform mixture of the CYC carrier and drug can be achieved. In some cases, the release composition may be formulated to minimize or substantially eliminate the burst effect and/or to give a zero order, a $1^{st}$ order or a mixture of a zero and first order release of a drug or other release material, including sustained delivery of therapeutically effective levels of drug. Furthermore, in some cases, external heating of the release composition, after it has been delivered to the target site, can result in delivery of the drug or other release material at a desired location and/or time.
e) Bioerodability, as described above.

The CYC carrier can be used in combination with other polymers, for example amorphous polymers. For example, the release composition can also contain simple acrylate copolymers which are good film formers, particularly where film-forming properties in addition to drug delivery properties are important, as for example in a medical stent.

In some embodiments, it is useful to employ a CYC carrier which includes acid groups to enable oral drug administration of a peptide or protein drug. The Cy moieties protect the drug formulation in the highly acidic stomach environment, but at the high pH in the alkaline upper intestine, the presence of the acid groups causes swelling and release of drug by diffusion, and, in the case of bioerodable CYC carriers, also by bioerosion.

The presence of acid groups in the CYC carrier may also make it possible to create a fine suspension of the drug/CYC carrier matrix in a suitable aqueous medium for use in subcutaneous injection. Once injected, the acid-containing CYC carrier swells and forms an "in-situ" gel platform from which the peptide or protein is released through diffusion by pore or channel formation or bioerosion of the bioerodible gel.

In some embodiments, the CYC carrier, preferably, a CYSC acrylate or ECC PLGA, has a Tp slightly above the normal body temperature of the organism into which the release composition is to be injected. Such a product can for example be administered intravenously, and thereafter activated by some external heat source so that the peptide or protein drug is released at a desired location, e.g. in a cancerous area, adjacent to a tumor. By adjusting the external heating, the release of the drug may be intermittent or bolus release.

Methods of Release

In one embodiment of the invention, a pharmaceutical formulation of the invention is released in a controlled manner. The method optionally has one or more of the following characteristics
  (a) the drug is released over an extended period of time;
  (b) no more than 80%, preferably no more than 50%, for example no more than 30%, of the total drug loaded into the formulation is released from the formulation over a period of time of 6 hours following administration of the formulation to a subject;
  (c) less than 50%, or less than 10%, of the total drug loaded into the formulation is released over a period of time of 1 hour, or over a period of time of 2 hours, following administration of the formulation to a subject;
  (d) at least 75% of the total drug loaded into the formulation is released within 30 minutes of activation of the formulation;
  (e) the rate at which the drug is released from the formulation after administration is influenced by (i.e. commenced, increased, reduced or ended) by a change in one or more of the following conditions
    (i) heating or cooling caused by external action, e.g. heating,
    (ii) hydration of the formulation,
    (iii) exposing the formulation to an enzyme,
    (iv) changing the pH of the environment surrounding the formulation.

For example, in some embodiments the formulation releases a therapeutic dose of the drug only at or above a certain pH. For example, a formulation may release little or no drug in an aqueous environment at an acid pH (such as the stomach), but release a therapeutic dose of the drug at a less acid pH such as at pH6, or an alkaline pH, such as pH7, pH8, pH9, or pH10 or above. This application is particularly useful for the oral delivery of acid labile drugs such as proteins or peptides that are damaged by the acid environment of the stomach.

Drug Loading & Release

In preferred embodiments, this invention provides one or more of high drug loading, low burst effect, and sustained release of a drug from a CYSC polymer formulation tailored to provide the desired characteristics for the particular drug.

Total drug loading is the amount (usually expressed as the percentage by weight) of the drug present in the formulation. The drug may be chemically and/or physically bound to the CYC carrier, for example physically entrapped in the formulation. Binding of the drug to the polymer may be through covalent and/or ionic and/or hydrogen bonding and/or van der Waal's forces and/or hydrophobic interactions.

Many known drug formulations contain less than 5% by weight of drug. For example, the polymers conventionally used for sustained release formulations, such as PLGA (co-polylactic acid-co-polyglycolic acid) and amorphous acrylic copolymers accept only relatively low drug loadings of between about 1% and 5%. In contrast, preferred embodiments of the present invention provides formulations with relatively high drug loading.

Tailoring drug loading and release properties for a particular drug may be achieved for example through selecting polymers with a combination of desired features relating to (a) ionic or covalent attachment of drug molecules to CYC carrier, and/or (b) capturing the drug molecules in the crystalline hydrophobic domain, and/or (c) presenting a tortuous path around crystalline domains that drug molecules in the hydrophilic domains must navigate to reach the exterior and/or (d) ensuring that the crystalline domains are preferentially on the outside of the formulation. Methods of preferentially locating the crystalline domains on the exterior include, for example, forming particles in air using a spinning disk allowing the hydrophobic side chains to come to the low energy interface or in a hydrophobic medium that would again draw the hydrophobic side chain to the interface, or actually coating preformed particles.

Drug loading and release properties of CYC carrier formulations can for example be controlled by altering the solubility of the drug in the CYC carrier and/or providing association sites for the drug to interact with the CYC carrier. For example, if the drug is a protein or polypeptide, the CYC carrier can contain ionic groups which are preferably selected from those cationic or anionic groups which naturally associate ionically or through hydrogen bonding with the carboxyl or amide groups of the protein or polypeptide side chains. Such ionic groups can be derived from suitable cationic or anionic comonomers forming part of a CYSC or ECC polymer or can be subsequently prepared on a preformed polymer, for example by quaternization of a tertiary amine moiety on a comonomer. Quaternization can for example be carried out by treatment with a methyl or other alkyl chloride or a dimethyl or other dialkyl sulfate.

A more hydrophobic drug may be associated with a CYC carrier having few or no hydrogen bondable or ionic groups. However, such a CYC carrier may yet contain ionic groups or have hydrogen bonding capability such that it can associate with many drugs, have a lower concentration of hydrogen bondable or ionic group containing monomers.

In the case of sustained release formulations, several days, weeks or even months of therapeutically effective dosage may be required. A formulation of the invention (such as an implanted drug formulation or device, such as a coated stent or solid implant or polymeric drug depot) may provide such dosage for at least 5 hours, at least 12 hours, at least 24 hours, at least 36 hours, at least 72 hours or at least 100 hours, or even longer, for example at least one week, or at least two weeks, or at least three weeks, or at least a month or at least three months, or at least six months, or at least a year. In some embodiments, interactions between the drug and the CYC carrier slow the release of the drug from the polymer into the surrounding physiological environment. For example, the interaction of the hydrophobic side chains of the crystalline side chain polymer with a hydrophobic drug will delay dissociation of the CYC carrier and drug. If the drug is hydrophobic, the drug will tend to associate strongly with the hydrophobic side chains of the CYC carrier, delaying release into a less hydrophobic (e.g. aqueous) environment. The Cy moieties of the CYC carrier influence melting behaviour; and once the carrier has melted, the Cy moieties act somewhat like a plasticizer (although they are of course still attached to the remainder of the CYC carrier). As a general rule, and other things being equal, the rate at which a drug will be released will be decreased by (i) an increase in the crystallinity of the CYC carrier, (ii) an increase in the molecular weight of the CYC carrier, and (iii) an increase in the strength of the bonds between the drug and the CYC carrier.

The drug formulations of the invention can be specifically designed to provide controlled and/or sustained release. For example, a drug formulation of the invention may be designed so as to release no more than a certain amount of drug over a specific period of time under certain defined circumstances. The rate of loading and release will depend on the specific drug-polymer pair. For instance, a single dose of a drug formulation may release no more than 5% of the total drug loaded into the dosage form, or alternatively no more than 1%, 3%, 10%, 20%, 30%, 40%, 50%, 60% or 70% over a period of 1 hour, or alternatively 3 hours, 6 hours, 12 hours, 18 hours, 24 hours, 36 hours, 48 hours, 72 hours or any combination of the foregoing numbers.

The rate of drug released may be approximately zero order during the main period of therapeutic administration, for example over 99% or 95% or 90% or 80% or 75% of the period of therapeutic administration, or over a period defined by the period of implantation. The maximal variation of drug release rate over the main period of therapeutic administration (for example during the period when therapeutic administration is occurring, at least 12 hours following administration, and before drug release falls below a therapeutically effective level) may not be greater than 50% (or 40% or 30% or 20% or 10%) from the mean rate of release during that period.

The plasma concentration of a drug will be related to the rate of release into the blood balanced against the rate of clearing of the drug from the blood (the drug half-life concentration). The aim of sustained drug delivery is to achieve a therapeutic plasma concentration of the drug over a desirable extended period of time. The desired therapeutic plasma concentration will be a concentration within the therapeutic window below which drug is ineffective, and above which the drug is toxic, or alternatively has no additional beneficial effect.

In a typical embodiment of the invention, a therapeutic dose of the drug as measured by plasma concentration (but alternatively as measured by clinical measurements) will be released over a period of time ranging from at least an hour to at least twelve months. Exemplary drugs suitable for sustained release include, for example, anti-pain medications (e.g. morphine analogues), anti-psychotics (e.g. risperidone or olanzapine), anti-inflammatories (e.g. steroids or NSAIDs), cholesterol lowering drugs (e.g., statins), osteoporosis drugs (e.g. biphosphonates), anti-angeogenics (e.g., anti-VEGF) and contraceptives. In the case of certain drugs such as contraceptives and osteoporosis drugs, sustained release may be desirable over a period of more than a year, for example at least 2, 3, 4, or 5 years. Prior formulations (Norplant) have been used to deliver a therapeutic dose of contraceptives over a period of three years. Long term sustained release formulations will generally be formulated for implantation within the body, e.g., subcutaneously.

The amount (weight) of drug released over a period of time will be related to therapeutically effective plasma concentration of the drug, the potency of the drug and drug kinetics including the residence time in the various tissues of interest and the rate of clearing. In use, the rate of release of a drug from the pharmaceutical composition of the invention may be no greater than, for example 10 ng per hour, or alternatively, 50 ng 100 ng 500 ng 1000 ng 2500 ng or 5000 ng or in other embodiments, no more than 10 µg, 50 µg or 100 µg or 500 µg or 1000 µg per hour during the first 6 (or 12 or 24 or 36) hours following implantation. Of course, the desired rate of release of the drug will depend on its potency, its therapeutic window and its half life. For example, Risperidone may be released over a period of time to provide a serum concentration of about 15 ng/ml up to about 100 ng/ml. A release of about 4 mg/day (or in other studies between 1 and 60 mg/day) is found to provide adequate therapeutic serum levels of Risperidone.

In practice, when the drug is released from the formulation, it is released into the surrounding environment, which may be, for example, the intestinal lumen, gastric fluid, subcutaneous tissue, blood, muscle, the colonic space, a body cavity, or any surrounding tissue and/or into interstitial space. The rate of the release is not always easy to measure in practice, and the invention includes methods of determining the rate of release of a drug from a formulation of the invention in vitro, such as by using standard methods such as those described in the United States Pharmacopoeia. One such method, employs a large volume (usually about a liter) of phosphate buffer, pH 7.2, maintained at 37±0.5° C. and stirred at 100 rpm by using a paddle-type dissolution apparatus (such as may be obtained from Electrolab, Mumbai, India). Drug release studies are generally carried out in triplicate and the mean values are calculated. Many standard methods are well known, and when release rates are described and discussed herein, such release rates may be calculated and compared by these standard methods.

In some embodiments, the formulation is such that less than 20%, or less than 15%, or less than 10% (or in other embodiments, less than 1%, 3%, 5% or 7%) of the total drug loaded into the formulation is released from the formulation prior to activation of the formulation by a specified condition which triggers a substantially greater rate of release. Such release triggers include, for example, a change in pH and/or swelling of the polymer by hydration and/or contact with an enzyme and/or heating of the formulation. Such heating can for example make use of one of the means described above. Immediately following the specified condition, the formulation may release drug quickly as a bolus, or steadily over a period of time. For example it may release at least 50% (or 30%, 60% or 75%) of the total loaded drug over a period of not more than 1, 3, 5, 7, 10, 20, 30, 45, 60, 120 or 360 minutes following activation. In embodiments wherein a bolus release is required, substantially all the drug may be released over a very short period of time, such as not more than 1, 2 or 3 minutes, or in other embodiments where longer release is desired, over a period of not more than 30 minutes.

In some embodiments, the rapid melting characteristic of CYC carriers is used to provide formulations which can be administered in the body and transported to a targeted disease site with little or no release of the drug during transport, but which can be triggered to release the drug at the site by targeted radiation which melts the CYC carrier at the site. In this way a large dose of a drug can be delivered specifically at the target site when needed. This is particularly useful when dealing with toxic drugs that are best delivered in a site-specific manner and not systemically. Site-specific delivery also reduces the dose needed. Such drugs include cytotoxic agents such as chemotherapeutics. The external source of radiation may be, for example, a focused beam of radiation, e.g. infra-red (IR) or radiation of a similar wavelength. For example the radiation source may have a wavelength of about 400-1500 nm, e.g. 500-1200 nm or 700-1100 nm. This heat-induced release mechanism may be particularly useful in embodiments wherein the formulation is targeted to a specific site prior to release of the drug. Such embodiments include formulations to target tumour tissue whereby, upon heating, a chemotherapeutic agent is released locally, providing a concentrated bolus of drug at the target site, but minimizing systemic exposure.

For example, a chemotherapeutic agent such as carboplatin may be formulated with a CYC carrier and a targeting ligand such as an antibody or folate that binds selectively to a cell surface receptor differentially expressed on the surface of a specific type tumour cell, for example a colon cancer cell. The formulation may for example be formulated as an emulsion and delivered orally. The emulsion will pass through the stomach and gut to the colon where it will preferentially adhere to tumour tissue. Excess formulation will be voided. An infra-red (IR) source will be used to target the tumour site, heating the adhered formulation and releasing the Carboplatin at high concentration to the target site. Little or none of the drug will be released from the formulation until the formulation is heated. This method of administration reduces the amount of drug delivered systemically and thereby reduces the damaging effects of toxic drugs on healthy cells. In certain embodiments, a material which can be heated by radiation, e.g. carbon nanotubes, may be mixed into the formulation. A similar embodiment might employ venous delivery of a liquid or emulsion formulation wherein the drug formulation specifically binds to a target at any location reachable by the circulation. Initial burst release of a drug is often (but not always) undesirable, and particular embodiments of the present invention provides a reduced burst effect due to the interactions between the drug and the crystalline side chains of the polymeric carrier material. In certain embodiments the formulation of the invention releases a drug so that the initial release of drug does not exceed the upper threshold of the therapeutic window. In other embodiments it exceeds the upper therapeutic window threshold for no more than 1 hour (or alternatively no more than 2, 3, 4, 5, or 6 hours). In certain embodiments the formulation of the invention releases a drug so that the maximum initial release of drug does not exceed by more than 50% the mean rate of release of drug (the mean rate measured over a period from 3-12 hours post administration). Alternatively the maximum initial release of drug does not exceed by more than 20% or 30% or 40% or 70% or 100% the mean rate of release of drug as measured over a period from 6-24 hours or 1-12 hours or 12-48 hours post administration. Often a formulation of the invention may be implanted directly into a subject to provide acceptable burst effect and sustained release. But for some formulations, and particularly with some particularly toxic drugs that have a narrow upper limit to their therapeutic window, pre-treatment of the formulation may be done to reduce burst effect in vivo. Pre-treatment may simply involve soaking the formulation in a biocompatible liquid or elution buffer, for example phosphate buffered saline (PBS) or water for a period of time before implantation. In such an embodiment, the solid polymer formulation would be removed from its packaging, and placed in the elution buffer for, for example 30 minutes to an hour. In some embodiments longer soaking times may be desirable, for example overnight. Soaking may continue for any duration, for example for up to (or alternatively not more than) 1, 3, 6, 9, 12, 24 or 46 hours. This period of soaking will allow the formulation to equilibrate with its liquid environment and may provide some degree of hydration (if hydration does occur), such that any drug that has migrated to the surface, or any drug that would provide a burst release when implanted into the subject will be released during the soaking period. After the soaking period the formulation will be implanted into the subject to provide sustained release of the drug within a therapeutic window.

In one specific embodiment the formulation is provided as part of a kit, wherein the kit comprises a two-chamber blister pack having the formulation in a first chamber and a liquid (an elution buffer, e.g. PBS) in a second chamber, and wherein an operator can break the seal between the first and second chambers allowing the liquid to contact the formulation. The formulation is pre-treated in the liquid for a period of time, for example from 30 minutes to 2 hours to allow any burst to dissipate. The formulation is then removed aseptically from the packaging and implanted into the recipient subject, for example implanted subcutaneously by use of a simple trocar.

Induced Drug Release

Temperature or pH changes may be used to induce drug release at a desired time and/or location. In some embodiments, a small increase in the temperature of the formulation, in situ in an organism, for example from body temperature to a temperature above body temperature, but below a temperature which would damage the organism around the formulation, causes the CYC carrier to melt, so that it changes from a crystalline to an amorphous structure. The combination of the loss of crystallinity, and in the case of a hydrogel, loss in volume, are factors which are useful in the delivery of the drug.

Focused infrared radiation, for example, can be applied from outside the body to selectively heat a target within the body. In some embodiments a formulation may be delivered to a particular location within a patient without appreciable release of drug. When and where desired, an IR beam can be used to heat the target, causing a bolus release of drug at the desired location and time. One such embodiment uses a formulation that includes a ligand that binds specifically to a target. Such ligands may be, for example, antibodies, and are discussed further herein. The formulation is delivered to the patient, for example intravenously; the ligand allows the formulation to bind to and accumulate at a target, such as cancer tissue; a focused IR beam is applied to the target tissue, thereby releasing a bolus of drug.

Another method of promoting the release of a drug associated with a CYC carrier inside a human body or other organism is to supply heat to the CYC carrier, for example through one or more of a hot compress, hot water, hot contact wand, hot pad, infrared radiation, and penetrating heat via near infrared radiation; and/or by generating heat within the formulation. For example, the formulation can include a component which will generate heat when exposed to electromagnetic radiation of a particular range of wavelengths. Such components include for example carbon fiber nanotubules or particles which absorb near-IR light in the range of about 700-1100 nm, silver particles or gold particles.

In various other embodiments a transdermal formulation may be applied to the skin and heat may be produced by chemical or electrical means, or even by physical means such as rubbing with the hand to produce friction-induced heat, to provide a bolus release of drug. Such embodiments are further described herein.

The formulations may include a remotely controlled release mechanism to trigger release of the drug, e.g., an electromechanical mechanism that allows an operator to release drug by use of a radio-frequency signal, sent, for example, over a computer network such as the Internet or a hospital intranet. Such a mechanism may employ, for example, solenoids, electromagnetic gates or other microfluidic flow control mechanisms. Such mechanisms are well known in the microfluidic and MEMS industry. A remotely operated heating element may be provided to heat the formulation and thus release a bolus of drug.

In some embodiments a therapeutically effective dose of the drug may be released at a predetermined time wherein the drug is released from the formulation by one or more of the following changes in condition (i) heating the formulation, (ii) hydration of the formulation, (iii) exposing of the formulation to an enzyme, or (iv) changing the pH of the environment surrounding the formulation.

Methods of Administration of the Formulations and Diseases that May be Treated Using the Formulations of the Invention.

The formulations of the invention may be administered in various ways. Exemplary types of administration include: ingestion, injection, parenteral administration, oral, subdermal, transdermal, transmucosal, intrathecal, intramuscular, inhalation, and application to the skin. Compositions and devices of the invention include lozenges, capsules, tablets, pills, pessaries, lavages, suppositories, inhalable powders, creams, solutions, suspensions, oral suspensions, emulsions, micelle systems, nanoparticles, vesicles, nanocapsules, microcapsules, microparticles, microspheres, microparticles, particles, hydrogels, pills, tablets, including sub-lingual tablets, depots and injectables. Hydrogels are sometimes a preferred form in that they can be mixed as a powder with the drug in a solvent medium to hydrate the hydrogel/drug mixture.

The preferred formulation and route of application will depend upon the drug and the desired application. Sustained release formulations will need to reside in or on the body for the period of desired release, therefore such formulations will be implants, implanted devices and patches, for example transdermal, or transmucosal. Pills, capsules and syrups are typical for oral/gastro-intestinal formulations that are resistant to acid degradation. Because of their susceptibility to acid or severe environments, polypeptides and proteins are often administered by injection as suspensions or solutions. Topical application of other drugs will typically be in suspension or cream form.

Diseases that may be treated by the formulations of this invention include, but are not limited to, cardiac diseases, cardio-vascular diseases, neoplastic diseases, inflammation and all diseases associated with the inflammatory process such as arthritis, auto-immune diseases such as lupus, allergies, infectious diseases (viral, bacterial, fungal, protozoan and prion), endocrine diseases such as diabetes, obesity and all forms of weight-related diseases and disorders whether clinically significant or not, hypertension, psychosis, anxiety, depression or any psychological disease, addiction, erectile dysfunction or any sexual dysfunction, blood-lipid diseases such as high cholesterol, Alzheimer's, alopecia, propecia, mange, incontinence, pain, Meniere's disease, migraine, tinnitus, osteoperosis, fertility problems and any other disease of an organism for which administration of a drug is warranted.

Organisms that can be treated by the present invention include for example human beings and other mammals including bovines, primates, equines, ovines, porcines, canines and felines, and also birds, fish, ungulates and members of the Mustelidae family such as Meles meles.

Other Medical Applications

Other medical applications of the invention are described below. They are:—
1) Delivery of polynucleotides including RNA interference (RNAI) using cationic CYC polymers.
2) Biodegradable CYC polymers as tissue scaffolds.
3) Biodegradable CYC polymers as ocular inserts
4) Biodegradable CYC polymers in drug eluting stent applications 1. Delivery of Polynucleotides Including Rna Interference (RNAi) Using Cationic CYC Polymers It is known to deliver polynucleotides by complexing cationic polymers such as poly(lysine) with negatively charged polynucleotides. Such cationic polymers usually have amines at the terminal ends of short conformationally flexible side chains. These polymer delivery systems have limitations such as non-biocompatibility/biodegradability or poor gene transfection efficiency. Cationic CYC polymers can be formulated so that the backbone and/or the terminal groups contain amine groups which are available to interact with polynucleotides or their derivatives to form polynucleotide/polymer complexes for efficient delivery of polynucleotide. Such complexes, and methods of using such complexes to deliver polynucleotides, are novel and form part of the present invention. Delivery systems using cationic CYC polymers may have several potential advantages. First, the polymers can be biocompatible, biodegradable or excretable from the human body. Secondly, the interaction of the polymer with the polynucleotide will stabilize the polynucleotides and prevent the degradation of the polynucleotide. Thirdly, the versatility of CYC polymer chemistry allows one to prepare a neutral or slightly-positively-charged complex that more easily crosses through the hydrophobic membranes (e.g., cytoplasmic, lysosomal, endosomal, nuclear) of the cell, thus increasing transfection efficiency. Finally, the versatility of CYSC polymer chemistry enables preparation of a variety of polymers which complex well with polynucleotides and therefore, potentially further improve transfection efficiency.

The CYC polymers for this application are preferably the ECC-PLGA polymers and salts thereof. In one embodiment, the cationic CYC polymer is preferably at least partially protonated to form a complex with the negatively charged polynucleotide. The polymers can be biodegradable or non-biodegradable. Typically, the polymers have one or more amines in the backbone of the polymer. Preferred polymers have one or more amines per repeating backbone unit. In another aspect of the invention, polymers may have amines at the terminal ends of side chains or terminal positions of the backbone chains. The polymers may be homo-polymers or co-polymers.

The cationic CYC polymer is preferably biocompatible and biodegradable, as defined above.

A polynucleotide can be complexed with the CYC polymer by any means known in the art. The complex can be in the form of particles, for example ranging in size from 100 micrometer to 10 nanometers, and can be prepared using known techniques. Preferably the complexes are combined with pharmaceutical excipients to form pharmaceutical compositions suitable for delivery to animals including humans. In one embodiment, the polynucleotide/polymer complexes form nanoparticles that are useful in the delivery of polynucleotides to cells. The polynucleotides used in this application may be any nucleic acid, including but not limited to, RNA, RNA interference (RNAi), DNA, ribozyme, DNA-RNA hybridizer, and oligonucleotides. The polynucleotides may be of any size or sequence, and they may be single- or double-stranded. Polynucleotides may be modified by any means including but not limited to methylation, phosphorylation, end-capping, etc. These derivatives may also be prepared by modification of functional groups of a polynucleotide, including but not limited to, the bases, sugars, and/or phosphate linkages, by techniques known in the art. The polynucleotides may contain any sequence which encodes a protein or a peptide. The polynucleotide may also contain regulatory regions that control the expression of a gene. In a preferred embodiment, the polynucleotide in the invention is an antisense agent or small interfering RNA (siRNA).

2. Biodegradable CYC Polymers as Tissue Scaffolds

It is known to use synthetic biomaterials as a matrix for cell or tissue scaffolds for tissue engineering in orthopaedic, soft tissue, cartilage and nerve repair.

Typically those scaffolds are prepared by seeding biomaterials with cells in culture. An interaction of biomaterials with cells yields a three-dimensional scaffold/biological composite with functional tissue equivalents. Those scaffolds can then be grafted into the same patient to function as a replacement tissue. Some such systems are useful for organ tissue replacement where there is a limited availability of donor organs or where, in some cases (e.g. young patients) inadequate natural replacements are available. Various materials including biodegradable polyesters—in particular poly(lactide-co-glycolide)s—have been used in the studies.

This application makes use of a biocompatible or bioerodable CYC polymer as a scaffold for tissue engineering applications. The CYC polymers are useful for this purpose because they can comprise a macropore structure with a high level of interconnectivity between macropores.

The preferred ECC polymer for use in this application is an ECC-PLGA type block copolymer, for example as described above.

The CYC polymer for use in this application is biocompatible, and preferably biodegradable, as defined above. It may be in any physical configuration, including but not limited to, bead, disk, particle, film, rod, body shape, etc. A preferred matrix is three dimensional, and is permeable to body fluids.

In one embodiment, the CYC polymer matrix has a macroporous structure including interrupted pore walls and polymer struts, since such a structure allows cell growth which is crucial for the development of three-dimensional tissue. In one aspect of this application, a polymer scaffold comprises macropores in the millimeter size range, preferably, ranging in size between 0.1 mm to 5 mm. In another aspect, the polymer scaffold has a porosity of 50-90%. Preferably, macropores in the polymers are interconnected, and the voids of the macrostructure are substantially continuous.

In one embodiment, the porous polymer matrix changes its size less than 50% after cells are seeded into the matrix, and/or changes in porosity size less than 50% when cells are seeded on the matrix.

In order to promote cell attachment to a polymer matrix, a preferred matrix may contain any moieties that enhance cell adhesion to the matrix. Those moieties include, but are not limited to cell-binding peptides/proteins such as Arg-Gly-Asp (RGD) and Tyr-Ile-Gly-Ser-Arg (YIGSR), etc. The cell-binding compounds may be attached to a polymer chain, or a surface of a preferred matrix by electrostatic forces, covalent bonding, or any other mechanisms using techniques known in the art.

The CYC polymer matrix may have a coating. The coating may be attached to the matrix by electrostatic forces, covalent bonding, or any other mechanism. Coating materials include, but are not limited to, hydrophilic polymers such as PEG, PVE, PEO, amphiphilic polymers such as Pluronics, and biological agents such as bone morphogenetic protein (BMP), etc.

The CYC polymer matrix optionally also includes one or more of the following:—

(1) Synthetic or naturally occurring polymers (hydrophobic or hydrophilic); examples include, but are not limited to, PLGA, poly(ethylene glycol), poly(ethylene oxide), polypropylene oxide, polypropylene glycol, poly(vinyl alcohol), polyurethane, collagen, gelatin, chitasan, sugar, and various derivatives of cellulose, etc.

(2) Amino acids, organic or inorganic compounds and salts, including but not limited to polylysine, collagen, gelatin, fibronectin, glycosaminoglycan, hydroxyapatite, sodium carbonate, sodium phosphate, calcium carbonate, and calcium phosphate.

(3) A compound selected from the group consisting of transition metal oxides, transition metal sulfates, transition metal carbonates, transition metal phosphates, and transition metal nitrates.

(4) Pharmaceutically acceptable additives or excipients.

(5) A living cell or a bioactive agent, including but not limited to proteins, peptides, vaccines, DNA, RNA etc.

This application of the invention includes a method of making a porous polymer matrix using a composition including a solvent, a porogen, and a CYC polymer. Preferably, the porogen is biodegradable or biocompatible or excretable or of natural origin. Typically, the method of making a porous polymer matrix includes (a) combining a CYC polymer solution and a porogen to form a mixture, and (b) extracting the porogen from the mixture and precipitating the polymer substantially simultaneously.

This application of the invention includes a method of making a tissue scaffold using a biocompatible and/or bioerodable CYSC polymer matrix in this invention. Typically, cell seeding of the polymer scaffold is performed using conventional methods well known to those of skill in the art. Cells are seeded onto the polymer scaffold and cultured for three-dimensional growth on polymer scaffolds under suitable growth conditions. The cultures are fed with media appropriate to establish the growth thereof.

The introduced cells attach to the connective tissue within the matrix and are fed by the blood vessels. The elements of these materials can be overlaid with a second material to enhance cell attachment. The polymer matrix is configured to provide access to ingrowing tissues to form adequate sites for attachment of the required number of cells for viability and function and to allow vascularization and diffusion of nutrients to maintain the cells initially implanted. Cells of various types can be grown throughout the present polymer scaffold. In an embodiment, cell types include, but are not limited to, cells selected from the group consisting of hepatocytes, pancreatic islet cells, fibroblasts, chondrocytes, osteoblasts, exocrine cells, cells of intestinal origin, bile duct cells, parathyroid cells, thyroid cells, cells of the adrenal-hypothalamic-pituitary axis, heart muscle cells, kidney epithelial cells, kidney tubular cells, kidney basement membrane cells, nerve cells, blood vessel cells, cells forming bone and cartilage, and smooth and skeletal muscle cells.

In one embodiment, a biodegradable CYC polymer matrix serves as a support or scaffold on which cell growth occurs in vitro prior to implantation in vivo (pre-seeding). In another preferred embodiment, the scaffolds may also be used directly in vivo, without being pre-seeded with cells.

In an embodiment, biodegradable CYC polymer scaffolds in the present invention are suitable for the growth of connective tissues, like bone, cartilage, paradontal tissue, as well as dental tissues and other organs, such as liver or breast tissue.

In one embodiment, a CYC polymer scaffold is may be used for biomedical applications, such as bone or tissue replacement. The CYC polymer can be biodegradable, or biocompatible but not biodegradable, when a permanent scaffold is needed to support other tissue or in applications where the scaffold is used as a filter.

The scaffold can contain therapeutic agents and act as a delivery vehicle for biologically active moieties, e.g. from growth factors, genes and drugs.

3. Injectable and Biodegradable CYC Polymers as Ocular Inserts

Pharmaceutical formulations comprising CYC carriers can be used in ocular treatments, e.g. in injectable and biodegradable ocular inserts. The formulations can be biologically inert, biodegradable, non-allergenic, and insoluble in tear liquid.

The CYC polymers which can be used for this purpose include, but are not limited to, ECC-PLGA polymers.

The CYC polymer is preferably biodegradable (as hereinbefore defined) and insoluble in tear liquid. The CYC polymer may be a mixture of one or more bioerodable CYSC polymers with one or more one synthetic or naturally occurring polymers (hydrophobic or hydrophilic). Examples include, but are not limited to, PLGA, poly(ethylene glycol), poly(ethylene oxide), polypropylene oxide, polypropylene glycol, poly(vinyl alcohol), polyurethane, collagen, gelatin, chitosan, sugar, kaolin, talc, magnesium trisilicate, and various derivatives of cellulose, etc.

The CYC polymer can optionally be mixed with one or more of (1) a Cy-containing compound, including, but not limited to a fatty acid/alcohol containing the same or different Cy moieties;

(2) amino acids, inorganic salts or organic compounds, including but not limited to sodium carbonate, sodium phosphate, calcium carbonate, and calcium phosphate;

(3) pharmaceutically acceptable additives or excipients well known in the art.

The CYC polymer can be cross-linked.

The drug may be incorporated in several ways into the CYC polymer.

In one embodiment, an ocular insert and method include the covalent attachment of a drug, to a CYC polymer that contains functional groups, through labile linkages such as an ester linkage. The drug is released over time by hydrolysis of the labile bonds.

In another embodiment of the invention, a drug is dissolved or dispersed in the CYC polymer and the mixture is formed into an appropriately shaped article for ocular delivery.

An ocular insert containing an active substance to be delivered is typically prepared in one of several ways. For example, the polymer can be melted, mixed with the active substance and cast or injection molded into a device. Such melt fabrication requires a CYC polymer having a melting point that is below the temperature at which the drug degrades or is otherwise damaged.

An ocular insert containing a drug can be prepared by solvent casting where the CYC polymer is dissolved in a solvent and the drug dissolved or dispersed in the polymer solution and the solvent is then evaporated. Solvent processes require that the CYC polymer be soluble in organic solvents.

Another method is compression molding of a mixed powder of the CYC polymer and the drug or polymer particles loaded with the active agent.

The ocular insert is preferably sized, shaped and adapted for easy insertion and prolonged retention in the eye for administration of a therapeutically effective amount of the substance to be delivered. The insert can be any desired shape, including but not limited to a thin flexible film, a bead, a microparticle (a microsphere, nanosphere, or microcapsule), a rod, and a disc, etc. The insert can be prepared in any desired thickness and width.

The ocular insert may have a coating. The coating may be attached to the matrix by electrostatic forces, covalent bonding, or any other mechanism.

Coating materials include, but are not limited to hydrophilic polymers such as PEG, PVA, PEO, amphiphilic polymers such as Pluronics, and any other materials for desirable properties.

One embodiment, the delivery device provides the controlled release of a drug for 1-7 days or longer after a single administration, without the need to remove the device after the compound has been released.

Any drug can be delivered in this way. Examples include, but are not limited to, water soluble or water insoluble drugs such as nonsteroidal anti-inflammatory compounds, anesthetics, chemotherapeutic agents, immunosuppressive agents, steroids, antibiotics, antivirals, antifungals, steroidal antiinflammatories, and anticoagulants.

In a different aspect, this invention provides an ocular insert as described above except that it does not contain a drug and the method of using such an ocular insert to provide benefits which are not related to the delivery of a drug.

4. Biodegradable CYC Polymers in Drug Eluted Stent Applications

Various families of drug polymer chemistries have been used for coating a stent to increase the effectiveness of stenting procedures and control drug-elution properties. Polymeric coatings of polymers such as a polyamide, parylene or a parylene derivative, poly(butyl methacrylate), poly(ethylene-co-vinyl acetate), PLA-PEO and PLA-PCL have been reported. However, drug-eluting stents using such polymers exhibit deficiencies such as poor biocompatibility, unsatisfactory mechanical properties during roll down and expansion of the stent, and undesirable drug release profiles. A beneficial drug-polymer system needs to be biocompatible, have satisfactory mechanical properties, and provide a desired elution rate for a specific drug. The versatile chemistry of the biocompatible and/or bioerodable CYC polymers allows for the selection of desired properties, thus providing versatility in geometric design, strut size and drug delivery options to mitigate the deficiencies of the known procedures.

This application relates to the use of a biocompatible and biodegradable CYC polymers in drug-eluting stent applications as either a drug-polymer coating on a stent or a drug-polymer stent.

One aspect of this application for use of CYC polymers provides a stent coated by a coating of drug and a biocompatible, more preferable biodegradable, CYC polymer or a polymer mixture. Such a drug eluting stent coated by a CYC polymer is flexible for insertion into a body lumen in an expanded configuration, and is also rigid for support of the body lumen, and achieves a desirable drug release profile.

Another aspect of this application provides a biodegradable stent for implantation into a body lumen. Specifically, the present invention provides a stent formed from a CYC polymer or a polymer mixture allowing for manipulation of material properties, thus providing satisfactory and desired performances.

In one embodiment, the polymeric material used for making a stent or coating a stent of the present invention may be a CYC polymer, preferably an ECC-PLGA, including any bioerodible and biocompatible polymers described above. In a particularly preferred embodiment, polymers in the invention may be a mixture of one or more CYC polymers.

In various embodiments, the CYC polymer is mixed with one or more of the following
 (1) synthetic or naturally occurring polymers (hydrophobic or hydrophilic), for example PLGA, poly(ethylene glycol), poly(ethylene oxide), polypropylene oxide, polypropylene glycol, poly(vinyl alcohol), polyurethane, collagen, gelatin, chitosan, sugar, and various derivatives of cellulose, etc.,
 (2) a crystallizable small additive, for example a fatty acid/alcohol, alkylated PEG and the like, optionally containing the same or different Cy moieties,
 (3) pharmaceutically acceptable excipients including, but not limited to carbon nanotubes, hydroxyapatite and other biodegradable additives that can improve the mechanical properties of the polymer composition, and
 (4) pharmaceutically acceptable additives or excipients known in the art to assist targeted drug release.

One aspect of this application of the invention provides a system for treating a vascular disease, including a catheter; a stent that is coupled to the catheter; a polymeric coating of a CYC polymer or a polymer blend that is dispersed on the stent framework. A therapeutic agent is in contact with the polymer matrix. One aspect of this application of the invention is a method of manufacturing a drug-polymer coated stent, including the steps of forming a polymeric solution containing CYC polymers; applying the polymeric solution onto a stent framework; and drying the polymeric solution.

One aspect of this application for CYC polymers is a method of treating a vascular condition, including the steps of inserting a drug-polymer coated stent within a vessel of a body, and eluting at least one therapeutic agent from the drug-polymer coated stent into the body. The drug-polymer coated stent comprises CYSC polymers and at least one therapeutic agent in contact with the blended matrix.

Another aspect of this application of the invention is a system for treating a vascular disease, including a catheter; a biodegradable stent, comprising a CYSC polymer or polymer blend that is coupled to a catheter. A therapeutic agent is in contact with the polymer matrix.

Another aspect of this application of the invention using a biodegradable stent is a method of manufacturing a drug-biodegradable polymeric stent, including the steps of melting CYSC polymers, dispersing therapeutic agents into the polymer melt, and applying the process of casting or injection molding into a device to from a stent.

Another aspect of this application is a method of treating a vascular condition, including the steps of inserting a drug-biodegradable polymeric stent within a vessel of a body, and eluting at least one therapeutic agent from the drug-polymeric stent into the body. The drug-polymeric stent comprises a CYC polymer and at least one therapeutic agent in contact with the blended matrix.

Devices Employing the Invention

Various devices can make use of the pharmaceutical formulations of the invention. Such devices include coated devices, prosthetic devices, implanted devices, pills, depots and patches. In some embodiments a formulation of the invention is coated onto an implantable medical device. Such implanted devices include stents, pacemakers, catheters, screws, staples, sutures, prosthetic devices etc. Such devices can be made by applying the formulation to an interior or exterior surface of a device by dipping, painting, spraying, misting, rolling, or other method. In some methods, the formulation is heated to above its melting temperature and applied to the device and then dried to form a solid coating.

In another aspect, the devices are implanted depots such as solid, liquid and gelatinous depots that can be deposited into the tissue of a subject, for example by subcutaneous injection. In some embodiments, the formulation is heated to above its melting temperature and injected (or otherwise flowed) into the desired location, e.g. subcutaneously, where it cools and forms a depot which will then release drug in situ. In some such embodiments, Tp is only just above body temperature, e.g. less than 55° C., preferably less than 48° C., so that the formulation may be implanted with minimal discomfort or tissue damage. Once implanted, the formulation cools and crystallizes. Such an application may be of particular use in providing an implanted device that moulds to fit the internal shape of a cavity such as within an ablated area of an infracted heart, within bone tissue or subdermally.

In some embodiments, e.g. some depot embodiments, the formulation includes a non-polymeric substance, e.g. sucrose acetate isobutyrate (SAIB) and non-water soluble liquid materials having a viscosity of at least 5,000 centipoise at 37° C. that do not crystallize neat under ambient physiological conditions, for example those described in U.S. Pat. No. 6,992,065 (Okumu) which is hereby incorporated by reference in its entirely for all purposes. Such substances, for example SAIB, which are preferably highly hydrophobic, can enhance drug loading and/or modify drug release profiles. In some embodiments the material is physically mixed with the CYC polymers; in other embodiments it may be used as is or incorporated into the CYC polymer.

In some embodiments, devices include a formulation containing a radio-opaque dye or other marker so that the formulation can be imaged by fluoroscopy or X-ray. Many radio-opaque substances are commonly known and used such as barium, silver and gold.

Drug Delivery Devices

There are many drugs which can be administered by implanting a specific device into a patient. There are today commercial devices which work by swelling pressure from a polymer which forces a drug to be dispersed from a small cylindrical implanted container. In a similar manner a drug can be administered according to the present invention by implanting a CYC carrier/drug matrix, the CYC carrier optionally formulated with other polymers and/or formulating ingredients known for drug delivery devices. Or, a drug associated with a CYC carrier could be dispensed from a cylindrical metal or plastic tube or device with holes in the device to allow passage of fluid into, and dissolution of drug from, the device. Using implanted devices is particularly of interest for delivery of drugs over a long period of time, for example 1-2 months or longer, e.g. up 6 months, up to a year or in some cases for more than a year. As examples of drugs that might be dispensed are hormones, for example birth control drugs which can be administered like many hormones in very minute quantities, so that a reasonably sized device can be implanted into a patient, for example, in the upper arm, to dispense drug over the long desired time. Particularly if the device has to be explanted, this kind of an implant is only contemplated where long term delivery of small amounts of drug is desirable from a relatively small device which does not cause discomfort to the patient once it is implanted.

Another area where this kind of a device would be suitable is in the drug delivery of compliance drugs, for example, antipsychotic drugs, used by patients who often have difficulty in complying to simple oral pill administration on a regular basis. The implanted device would provide a constant and desirable release of a small amount of anti-psychotic drug as prescribed to assure patient compliance and avoid incidences which are costly to the medical system if the patient does not comply with the dosage schedule of an oral administered pill form. Also, the use of an implanted device may be suitable for patients with chronic or severe pain either from a terminal disease—e.g. cancer—or from a painful and chronic back, hip or other nerve-induced pain issue. Also, the melting behavior of the CYC carriers makes it possible to design an implanted device such that, at body temperature substantially no drug is released but at slightly above body temperature, for example 42° C., a small release of drug will occur. The release can for example be triggered by a radio signal to a very small responder in the device which heats only a potion of the polymer drug matrix to release a dosage amount of drug. It is also well known that many patients, especially elderly patients, often overdose on medications or take medications on incorrect schedules resulting in emergency hospitalization. There is, therefore, need for a device which will deliver a drug (or in some cases multiple drugs) over a long period, or at triggered intervals over a long period, in the dosage required.

This invention provides a drug delivery device which comprises, a pharmaceutical composition comprising an ECC carrier and a drug, and which has one or more of the following characteristics.

a) It can be implanted into a patient. For convenience, the device would always be implanted at the same location in a patient (in the inside area of an upper arm) so that it could be easily located by, for example, doctors.

b) It is biocompatible, but generally is not bioerodable so that it can be more easily explanted.

c) It delivers one or more drugs over a long period, e.g. 3-6 months, or at triggered intervals over a long period, in the dosage required.

d) It is capable of delivering a plurality of drugs e) it comprises a plurality of segments which are connected to each other, preferably in a way that makes it possible to replace each segment with a similar or different segment. Optionally, some or all of the segments can deliver the same drug, optionally in the same dosage, thus enabling delivery of a desired dosage (e.g. as a multiple of the dosage delivered by each segment, so that a doctor could specify a particular number of segments of a particular drug to raise or lower the dose). Optionally, some or all of the segments can deliver different drugs to treat a number of infirmities simultaneously (e.g. to treat depression, schizophrenia, anemia, high cholesterol or heart disease). Each segment can for example comprise a solid molded section of the drug/ECC carrier, optionally supported by a biologically inert structure which permits delivery of the drug and which connects adjacent segments f) one or more of the segments could contain a radiopaque additive, so that it would show up on an x-ray scan, and/or an RFID tag.

Personal Care Applications

The use of SCC polymers in personal care applications, e.g. hair care, skin care, sun care, color care and body care has been disclosed for example in U.S. Pat. Nos. and Patent Publications U.S. Pat. Nos. 6,540,984, 6,989,417, 7,101,832 and 7,175,832 (Landec Corporation); U.S. Pat. No. 5,736,125

(National Starch Corporation); U.S. Pat. Nos. 5,622,694, 5,662,892, 5,916,547, 5,919,439, 6,074,628 and 6,113,883 (Procter and Gamble Corporation); and U.S. Pat. Nos. 6,503,494, 6,572,869, 6,361,781, 6,569,409, 6,464,969, 6,565,839, 7,335,348, 6,789,550, 6,811,770, 6,949,504, 7,129,276, 7,255,870, 6,946,518, 7,090,420, 7,083,347, 2002041857, 2002127251, 2003039621, 2004005279, 2005188474, 2005191262, 2005172421, 2005191258, 2004180021, 2004191200, 2004228890, 2005031656, 2005013838, 2005142082, 2005123493, 2005008667, 2005031565, 2005169949, 2005169865, 2005261159, 2005175570, 2005180936, 2006078519, 2005287093, 2005287183, 2005287100, 2005287101, 2006078520, 2006130248, 2006233732, 2006216257, 2006292095, 2006263438, 2007134192, 2005137117 and 2003039671 (L'Oreal).

The SCC polymers disclosed in those patents and publications can be used to "structure" or thicken the oil phase of various anhydrous formulations (like lipsticks or underarm formulations) as well as thicken the oil phase of formulations containing an oil and a water phase, e.g. lotions, creams etc. They function by associating in the oil phase to create a network. This results in thickened formulations having improving sensory properties (e.g. texture, touch and feel). The SCC polymers can also be used in hair care styling and restyling formulations, using an SCC polymer having a Tp such that the hair can if desired be repeatedly styled and restyled by heating/reheating.

The CYC carriers, in particular the bioerodable CYC polymers, disclosed in this specification can be used in personal care applications, and can have significant advantages over the SCC polymers known for use in such applications. In particular, their bioerodability makes them environmentally acceptable ("green"), particularly bearing in mind that personal care compositions are often disposed of through household sinks and drains, and thus immediately become part of the ecosystem. Often the bioerodable CYC polymers degrade to natural materials like lactic acid, glycolic acid, fatty acids, glycerol, etc. The components of bioerodable CYC polymers can be selected to exhibit longer or shorter degradation rates, e.g. by selection of the blocks in a block copolymer. Even when it is desirable for a personal care composition to contain a polymer which is not bioerodable, a part of such polymer can often replaced by a bioerodable CYC polymer.

The CYC carriers suitable for use in personal care compositions include, but are not limited to, bioerodable CYC polymers, e.g. the following:—
(a) ECC-PLGA polymers—End capped crystalline PLGA copolymers containing 1, 2, 3, 4, or more Cy moieties.
(b) Alkyl polylactide polymers in which the methyl group of the lactide monomer has been substituted by Cy moieties.
(c) CYSC-PLGA block copolymers, in which the PLGA portion degrades leaving only a small amount of non-biodegradable polymeric units.
(d) Other polymers in which the main chain can be hydrolyzed (and is therefore bioerodable), for example
 1) Polycarbonates
  i. Side-chain crystalline dimethylol propionic acid (DMPA) polycarbonates
  ii. Side-chain crystalline polycarbonates from glycerin carbonate
  iii. Side-chain crystalline polycarbonates from monoglycerides, dimethyl carbonate, and optionally lactic/glycolic acid(s).
 2) Polyesters
  i. Side-chain crystalline malic, citric or tartaric acid polyesters
  ii. Side-chain crystalline malic or tartaric acid PLGA polyesters
  iii. Polyesters from glycidol, crystalline fatty acid and polybasic acid
  iv. End-cap crystalline PLGA polyol polyesters
  v. End-cap crystalline glycerin carbonate ECC-PLGA polyesters
  vi. ECC-12-hydroxystearic acid PLGA polyesters
  vii. Crystalline fatty ester dimethylol propionic acid polyesters
 3) Side-chain Crystalline Oxazolines
 4) Crystalline Alkyl Dioxanones
 5) Side-chain Crystalline Hyaluronic acid Personal care compositions can optionally also have one or more of the following features.
(a) The composition can contain a compound containing a long chain n-alkyl component which will "self assembled" with the biodegradable CYC polymer such components include for example fatty acids, fatty alcohols, modified PEG's, and polyhydroxy compound, e.g. sorbitol, which have been esterified or otherwise modified by reaction with an n-alkyl carboxylic acid or acid derivative in which the n-alkyl group contains at least 14, methods, preferably 18-30 or 18-22 carbon atoms.
(b) The composition can contain, in addition to the CYC biodegradable polymer, one or more other synthetic or naturally occurring polymers, e.g. PLGA, poly(ethylene oxide), polypropylene oxide, poly(vinyl alcohol), polyurethane, collagen, gelatin, chitosan or sugar.
(c) The composition can contain additives, which may be inorganic or organic, e.g. kaolin, talc, magnesium trisilicate, and various derivatives of cellulose.

Personal care compositions of the invention can be of any kind, including those disclosed in the patents and patent applications incorporated by reference herein. They can be used, for example, in any personal care application on the face, body, hair, eyelashes, lips, skin, scalp, nails, etc. They can, for example be deodorants, anti-perspirants, lipsticks, makeups, lotions, creams, oil-in-water emulsions, water-in-oil emulsions, hair care, color care, skin care, sun care, hair styling, hair restyling, shampoos, conditioners, nail varnishes, gels and oils, creams, hand creams, night renewal creams, body milks and lotions, light facial creams, protective day creams, liquid moisturizing emulsions, and products designed to remove makeup/personal care products.

The compositions can also contain any of a wide range of additives including those disclosed in the patents and patent applications incorporated herein by reference. The additives can for example be UV absorbers, fragrances, biocides, anti-microbial agents germicides, antioxidants, preservatives, disinfectants, enzymes, nutrients, minerals, and drugs (including pharmaceuticals which are active physiologically or pharmacologically, either topically or systemically.

Agricultural and Aquacultural Applications.

The CYC carriers used in the present invention are useful in compositions for agricultural and agricultural applications. The compositions can, for example, contain (in addition to the CYC carrier) any of the numerous bioactive materials which are known to be useful in agricultural and agricultural applications. Such bioactive materials include, but are not limited to, fertilizers, biocides, insecticides and fungicides. Specific examples of bioactive materials include Thiram, Fludioxaonil, Captan, Rival, and Apron and insecticides such as imidacloprid, chlothianidin, dinotefuran and thiomethoxam. The release compositions of the invention can be used to treat a wide variety of substrates, including for example seeds and soil. The CYC carrier can be used as part of a known treatment composition, or a CYC release composition can be applied in a separate step to improve a known treatment, for example as described in U.S. Pat. Nos. 5,129,180 and 7,175,832 (Landec Corporation), the entire disclosures of which are incorporated by reference herein.

By appropriate selection of the CYC carrier, the rate of release of the bioactive material can be controlled, often by reference to the ambient temperature and moisture content of the substrate itself or of the medium surrounding the substrate. The ability to control the release of bioactive materials, often so that they are released over a long period. It is important, for example, in the early stages of seed germination and seed emergence and early plant growth, such control may be achieved by a single application of a composition, or fewer applications of the same or different compositions, as compared to multiple applications to achieve the same benefits.

In some embodiments, particularly for seed coatings, the CYC carrier is a CYC emulsion polymer having a relatively high molecular weight. In other embodiments, particularly for seed treatments, the CYC carrier is a relatively low molecular weight CYC polymer which is useful in compositions for the controlled release of pesticides in the early treatment—during seed germination and emergence and early plant development of the agricultural crop involved.

The CYC carrier can be bioerodable, for example as disclosed herein in connection with the personal care applications.

The CYC carrier can for example be added directly to a preformed composition comprising a bioactive material, or a mixture of a CYC carrier and the bioactive material can be added to a preformed composition, for example as a solid suspension of particles.

The CYC carrier can be selected so that its Tp and its melting range are appropriately related to the temperature at which the substrate is most likely to be subject to undesirable influences, e.g. from pests, for example so that there is a bolus release of a pesticide to attack crop pests at the time when the pests are most active.

An advantage of the present invention is that, because all or most of the bioactive material is retained by the CYC carrier and is released only at a desired time, or over a desired period of time, the required amount of bioactive material is reduced. As a result, environmental contamination, e.g. in runoff water to streams and ponds, is reduced.

SSP Polymers

In the SSP polymers, the moieties $Y_{ch}$, b and Cy can be of any kind (within the definitions given). In SSP polymers containing different moieties of formula (1), the moieties can differ from each other in one or more of Ych, b and Cy. A wide variety of $Y_{ch}$, b and Cy moieties is described above. The moieties Z and Rzphil can be of any kind. In SSP polymers containing different moieties of formula (2zphil), the moieties can differ from each other in one or both of Z and Rzphil. A wide variety of suitable units of formula (2zphil) is described above, including, for example, units derived or derivable from one or more of acrylic acid, methacrylic acid, acrylamide, methacrylamide, AMPS (2-acrylamido-2-methylpropane sulfonic acid), acrylonitrile, methacrylonitrile, and other oxygen-containing and nitrogen-containing monomers. The moieties of the formulas (1) and (2zphil) can be derived from monomers which are randomly copolymerized together. However, the fact that the molar ratio of the units of formula (2zphil) to the units of formula (1) is at least 2.5:1 ensures that there will be at least some blocks containing a plurality of (2zphil) units. Alternatively, the polymerization can be carried out in a way that there are distinct blocks of each type of unit.

An SSP polymer will of course contain terminal units having a formula different from formulas (1) and (2zphil). The terminal units can for example be terminal units derived from one or more of the monomers from which the repeating units of formulas (1) and (2zphil) are derived, or modifications of such terminal units. In addition, an SSP polymer can optionally contain, in addition to the repeating units of formula (1) and (2zphil), and the terminal units, repeating units having a different formula. Purely by way of example, $Y_{ch}$ can be a

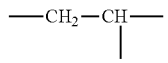

moiety, b can be a —$CO_2$— moiety and Cy can be an n-alkyl moiety containing 16-30 carbon atoms, for example derived from stearyl or behenyl acrylate or other n-alkyl acrylate or methacrylate; and the (2zphil) unit can be a moiety, derived from acrylic acid.

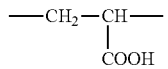

Known crystalline polymers whose crystallinity derives from long chain alkyl side chains are opaque. Surprisingly, however, some of the SSP polymers are transparent when solid. Such polymers are referred to herein as nanocrystalline polymers. The term "nanocrystalline polymer" is used herein to denote a polymer which, when formed into a thin film and tested by ASTM D 1003, has a haze value less than (preferably less than 0.8 times or 0.5 times) the haze value of a thin film which is composed of a copolymer of C18A and AA in a 1:1 molar ratio and which is formed and tested in the same way. The tested film exhibits a first order melt transition when measured by a DSC on the first heating cycle. The inventors believe that the crystal size of the nanocrystalline polymers is smaller than is required to scatter visible light, probably less than 100 nanometers. The parameters influencing the formation of a clear crystalline polymer are not only related to the co-monomers, chemical composition, molecular weights and viscosity, but are also influenced by the kinetic process of crystallization. Those skilled in the art will have no difficulty, having regard to their own knowledge and the disclosure of this specification, in determining whether or not a particular SSP polymer is a nanocrystalline polymer, and if it is not, what changes should be made to the polymer in order to increase the likelihood of obtaining a nanocrystalline polymer.

The SSP polymers of the present invention can optionally have at least one of the following characteristics.

(1) The molecular weight (Mn) of the polymer (measured as hereinbefore described) is at least 2000, e.g. at least 3,000, and/or at most 100,000, e.g. at most 50,000, or at most 25,000, or at most 12,000, particularly at most 10,000, e.g. 3000 to 12,000, or 3000 to 8000, or 4000 to 6000, if a nanocrystalline polymer is desired.

(2) The polymer is a polyacrylate.

(3) The repeating units of formula (1) comprise a straight chain polyalkylene moiety containing 17-21 —$CH_2$— moieties, for example derived from C18A and/or C22A.

(4) The polymer has a Tp of 40-80° C., preferably 42-63° C.

(5) The polymer has a Tp which is not more than 12° C. lower than, preferably not more than about 10° C. lower than, the Tp of a polymer which consists essentially of units of the same formula (1).

(6) The polymer has a (Tp−To) value of less than 10° C., preferably less than 8° C., for example 5-8° C., e.g. about 6° C.

(7) All the Ych and Z moieties are the same.

(8) The Rzphil moiety preferably has an $F_p$; value greater than 300 $J^{1/2}cm^{3/2}$ $mol^{-1}$ highly polar (for example —COOH and —CN moieties have $F_{pi}$ values of 420 and 1100 respectively where Fpi is the polarity component of the solubility parameter as described in van Krevelan's "Properties of Polymers"). Examples of suitable Rzphil moieties include —COOH, —$SO_3H$, —$CONH_2$, —CONHR and —$CONR_2$, where R is for example lower alkyl, and —CN.

(9) The Rzphil moieties contain less than three carbon atoms, preferably 1 or 2 carbon atoms.

(10) The units of formula (1) consist essentially of units of the formula

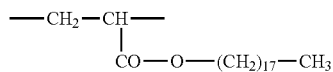

the units of formula (2zphil) consist essentially of units of the formula

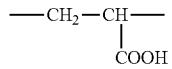

the molar ratio of the units of formula (2zphil) to the units of formula (1) is 2.5:1 to 4.5:1, e.g. 2.8:1 to 4.2:1; and the Mn of the polymer is preferably less than 7,000, particularly about 5,000.

(11) The units of formula (1) consist essentially of units of the formula

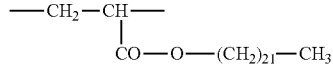

the units of formula (2zphil) consist essentially of units of the formula

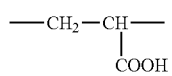

the molar ratio of the units of formula (2zphil) to the units of formula (1) is 3.5:1 to 4.5:1, e.g. 2.8:1 to 4.2:1; and the Mn of the polymer is preferably less than 7,000, particularly about 5,000.

(12) The units of formula (1) consist essentially of a mixture of units of the formula

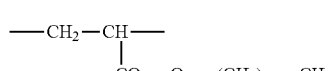

and units of the formula

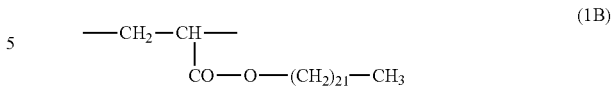

the molar ratio of the units of formula (1B) to the units of formula (1A) is 2.1:1 to 2.5:1; the units of formula (2zphil) consist essentially of units of the formula

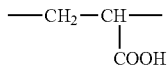

the molar ratio of the units of formula (2zphil) to the units of formula (1) is 2:1 to 3:1, e.g. 2.2:1 to 2.6:1; and the Mn of the polymer is preferably less than 7,000, particularly about 5,000.

The normal effect of large amounts of added comonomer in a CYSC polymer is to significantly reduce Tp, to significantly increase (Tp−To) and to significantly reduce the heat of fusion, because there are not as many side chain crystalline groups to develop large crystalline domains in below Tp. Surprisingly, in the nanocrystalline copolymers of this invention, this does not happen, in spite of the fact that the molar ratio of the units of formula (2zphil) to the units of formula (1) is more than 3, e.g. 3-6. Thus, the melting point is depressed only by a modest amount—about 10° C. or less—from the melting point of the same polymer without the units of formula (2zphil). It would have been expected that the Tp would have been depressed by much more than 10° C. at such molar ratios. In addition, the melting range of the nanocrystalline copolymer is about as sharp as the same polymer without the units of formula (2zphil).

It appears that in the nanocrystalline polymers, the Cy moieties crystallize together in much the same way as in a homopolymer. The inventors theorize, although the invention is in no way dependent on the correctness of the theory, that the nanocrystalline copolymers have a morphology-driven structure with short block runs of each comonomer to give a multi-block morphology, and that the different blocks are long enough to phase-separate before crystallization takes place, perhaps with the highly structured Cy groups close packing around clusters of the hydrophilic units (e.g. the highly polar units derived from acrylic acid, with their high potential for hydrogen bonding of the carboxylic acid group hydrogen atoms). In addition, the polymer crystal morphology may be significantly influenced by the polymer viscosity as crystallization takes place.

The SSP polymers of this invention often have molecular weights of 2,000 to 100,000, preferably 2,000 to 50,000, more preferably 3,000 to 25,000 and most preferably 3,000 to 12,000. The preferred nanocrystalline polymers generally have molecular weights less than 10,000, since higher molecular weights tend to result in increased opacity and haziness when observed in a small hardened film, indicating the presence of crystals large enough to refract light. Annealing the polymers at a temperature around $T_o$ results in an increase of the opacity of the nanocrystalline polymers, presumably because the size of the crystalline domains increases during the annealing process, thereby highlighting the influence of viscosity in allowing the crystallizing side chains to co-crystallize.

The SSP Examples below indicate how variation of the different repeating units and the molecular weight influences the presence or absence of nanocrystallinity in the polymer.

Uses of the SSPs

These new polymers are suitable for the following exemplary uses.

1) Use as a Thickener, Particularly in Personal Care Compositions

SSP polymers can thicken a water phase to form stable gels and emulsions when mixed with oils including simple vegetable oils, like canola oil to make a water-in-oil emulsion or oil-in-water emulsion. Depending on the composition of the SSP polymer, it may (a) be a good thickener of water-based compositions, in that it forms a gel in water as well as forming a stable emulsion under acidic conditions (generally SSP polymers with a molar ratio of repeating units of formula (1) to repeat units of formula (2zphil) of about 4;

(b) form a gel in water as well as stabilize emulsions under acidic conditions (generally SSP polymers with a wider range of a composition; and (c) only under acidic conditions, form a gel in water as well as stabilizing emulsions (SSP polymers generally).

Normally, one benefits by using polar comonomers to provide water phase solubility with the molecular weight of the polymer providing the thickening mechanism. In this case the thickening is a result of the intermolecular and intramolecular interaction of the long side chain groups on the polymer which overlap forming crystalline domains or associating domains and providing an associative thickening effect for the water-in-oil or oil-in-water emulsion. Because this effect has nothing to do with pH, this thickening can occur at low pH, below the normal pH of neutralization of pH=6 to 7. Thus, the SSP polymers are highly attractive as thickeners for skin care formulations which are formulated to a pH of 4 to 6, close to the pH of natural human skin. These skin care formulations thickened by these nanocrystyalline polymers will are stable once formulated and have soft and unusual texture when applied to dry skin. These simple but powerful nanocrystalline structures offer an interesting thickening alternative for skin care formula thickening in the pH=4 to 6 range, normally requiring a cationic thickener to provide the thickening effect now provided by the unneutralized SSP polymers of this invention.

After neutralization in a pH=7 or greater solution, the strong affinity of the highly polar acid groups will cause initial swelling and disruption of the crystalline regions. As a result the solutions will become amorphous and non-crystalline and still with the high concentration of acid groups retain some thickening quality similar to low molecular weight polyacrylic acid suspending agents and solutions, but such thickening is less than at the lower pH.

2. Use in Warm-off Adhesives

It is known that an SCC polymer can be used as an ingredient in a pressure sensitive adhesive (PSA) which has strong adhesion in use but which, when heated above the melting temperature of the SCC polymer, will lose adhesion rapidly, as a result of the SCC polymer migrating to the polymer/substrate interface. A disadvantage of the known PSA's of this kind is that they tend to be hazy. PSAs containing SSP polymers, in particular the nanocrystalline polymers, can likewise be removed by heating, but have improved properties, and in particular give a clear non-hazy film when cast as a PSA. This is desirable in a number of applications, for example clear bottle labels. The PSA is easily removed upon elevating the temperature above the Tp of the SSP polymer especially when the SSP polymer contains a high concentration of units derived from acrylic acid or methacrylic acid. Alternatively or additionally, PSA films containing SSP polymers containing acid groups can be easily broken down by exposure to an agitated alkaline wash bath which causes swelling of the polymer. For further details of warm-off adhesives to which the SSP polymers can be added, reference can be made to Landec U.S. Pat. No. 5,412,035.

3. Use in Cool-off Adhesives

It is known that an SCC polymer can be used as an ingredient in a pressure sensitive adhesive (PSA) which has strong adhesion in use but which, when cooled well below the melting temperature of the SCC polymer, will lose adhesion. A disadvantage of the known PSA's of this kind is that they tend to be hazy. PSAs containing the SSP polymers, in particular the nanocrystalline polymers, likewise may be removed by cooling, but have improved properties, and in particular give a clearer film when cast as a PSA.

4. Use as an Ionic Membrane Tunnel

If the acid or polar groups of the nanocrystalline SSP polymers are concentrated close to one another in the central core of the polymer molecules, then these concentrated ion centers could act as ion tunnels for transport of ions across a solid or supported coated membrane. These ion tunnels could be of interest in organic semi-conductors, e.g. in separator plates for batteries. Because of this high ion transport capability, these polymers might be suitable as solid electrolytes.

5. Use as a Clear Suspending Agent

The nanocrystalline SSP polymers will form a clear suspension with particulate nanoparticles, which is often desirable in the dispersion of nanoparticles in an emulsion or solution phase. For example, the formulation of clear sunscreen gels containing nanocrystalline zinc oxide particles suspended with the assistance of a nanocrystalline SSP polymer of this invention in an oil-in water or water-in-oil suspension is possible. The clear suspension of the zinc oxide nanoparticles in the nanaocrystalline polymer associative thickened polar phase would be a preferred form of spray or solution which is made possible by the clear nanocrystalline associative thickener of this invention. As a water in oil emulsion, a more water resistant sunscreen formulation would be obtained, desirable for a more permanent sunscreen yet upon alkaline washing by soap in a shower this clear sunscreen would be easily removed.

6. Use as a Drug Delivery Agent

The SSP polymers can be used as carriers for drugs, in the ways described in detail above. In particular, the SSP polymers, in particular the nanocrystalline polymers can be used as carriers for water insoluble small molecules to form stable small particles or gels that can be injected easily through narrow gauge needles. Injection could occur at low pH=4 to 5 and then, once the particles are in the body, the higher pH of the body will allow slow hydration and dissolution of the drug over a sustained time into the body.

7. Use as an Epoxy Cross-Linking Agent

The SSP polymers, in particular the nanocrystalline polymers, can serve as a stable crosslinking and latent crosslinking agent dispersed in a reactive diluent easily crosslinked by the polymer once melted above the temperature switch of the polymer. For example, a 1/4 molar ratio of C18A and AA can be mixed at room temperature with an epoxy resin to form a stable one package epoxy curing system. A Bisphenol A epoxy resin, for example, Epon 828, can be mixed with a stoichiometric or catalytic amount of a nanocrystalline polymer to form a stable epoxy solution at room temperature. Normally an epoxy resin mixed in this manner would slowly cure in storage to a hard crosslinked polymer. The nanocrystalline polymer of this invention forms a stable one component curing system with an epoxy resin. Once the temperature is raised above the melting temperature of the nanocrystalline polymer, rapid curing to a thermoset epoxy resin will occur.

The preferred epoxy resin to mix with the acid containing nanocrystalline polymer of this invention is a cycloaliphatic epoxy resin with internal oxirane functionality, for example, Unox 201 and the like, which because of the internal oxirane cures more rapidly than an external oxirane linkage with an acid containing polymer curing agent. In addition, epoxidized soybean oil or an epoxidized Poly BD resin can also be mixed with the nanocrystalline polymer of this invention to give a latent curing epoxy resin adhesive or coating system. In addition to being a clear crystalline toughener and crosslinker, the polymer may also act as a catalyst or contain an attached or matrixed catalyst whereby an epoxy catalyst is attached either covalently or ionically or by association, thereby, curing to a clear epoxy formulation.

8. Use as a Hair Styling Additive

It is known to use a conventional SCC polymer as an ingredient of a hairstyling formulation. The SSP polymers, in particular the nanocrystalline polymers, can be used in the same way, but give advantageous results. For example, the styled hair will have a shinier appearance, and the styling formulation will have better adhesion, allowing the hair to remain shiny and brilliant and non-flaking as a hair styling additive. Moreover, when the SSP polymer has a high acid content, it will be readily washed out of the hair.

9. Use as a Latent Active Scale Remover

The SSP polymers, in particular the nanocrystalline polymers, can form a stable suspension solution which is latent but which upon heating can remove scale or divalent cations from piping and containers.

10. Use as an Isocyanate Crosslinking Agent

The SSP polymers, in particular the nanocrystalline polymers can be used as a latent polymeric isocyanate crosslinking agent optionally in the presence of polyurethane reinforcing agents.

11. Use as Clear Floor Coating

A clear floor coating which can be repolished and reformed above its temperature switch is possible with the SSP polymers, in particular the nanocrystalline polymers. A conventional SCC polymer which is not nanocrystalline will form an undesirable hazy floor finish. Also, the nanocrystalline polymer of this invention can be removed easily as an additive in a floor finish by application of an alkaline removing system containing a dilute alkaline solution of ammonia or sodium hydroxide.

12. Use as a Reactive Metallic Paint Suspending Agent

A nanocrystalline SSP polymer can be employed as a metallic flake suspending agent for metallic paint finishes based on, for example, a thermoset acrylic or polyester binder and an aminoplast crosslinking resin. When heated above Tp during the curing cycle the nanocrystalline polymer would react with the binder to become part of the final coating system. Any unreacted residual nanocrystalline polymer would not crystallize to an opaque crystalline structure and detract from the brilliance of the metallic coating film.

13. Use as a Reactive Acrylate Nanocrystalline Polymer

A nanocrystalline SSP polymer can be used as part of an aminoplast crosslinking system in textile, paper and finishing systems. The nanocrystalline polymer can be mixed with an aminoplast resin at pH of 4 to 5 to give a stable suspended solution of the reactive nanocrystalline acid containing copolymer for coating and subsequent curing once the polymer is raised above its Tp.

14. Use as a Colloidal Dispersant or Suspending Agent

An SSP polymer can be used as a pigment or dispersing agent with properties of dispersing differently below and above the melting point, thus allowing thickening and dispersing below the melting temperature (in storage) and thinning and flow above the melting point while retaining good dispersing properties.

15. Use as a Low Foaming Surfactant

An SSP polymer can be used as a low foaming surfactant that below the Tp of the polymer emulsifies and forms a paste for a water-in-oil or oil-in-water dispersed system and above the melting point continues to emulsify to form a stable working solution of the emulsion.

16. Use as a Repulpable Additive for Adhesives/Paper Coatings

The SSP polymers, in particular the nanocrystalline polymers, could be added to a coating to provide a stable and dispersed suspension of the polymer in the coating used to coat paper to make a liner board or corrugated base stock which is resistant to water and provides assistance in the repulpability of itself and other resin binders in the corrugated or linerboard base. Once the polymer forms a film by itself or with other resins it is very water resistant, but under alkaline treating solutions, the polymer with high acid content readily dissolves, helping to float other binders away from the base stock paper material.

17. Use as a Temperature or Other Indicator

If a transparent solid, e.g. silica, is dispersed in an SSP nanocrystalline polymer, then the solid will not be visible. As the temperature goes up, the refractive indices will become mismatched and the silica will become visible. The refractive index may, for example, change dramatically over 10° C. and then follow a more normal change.

EXAMPLES

The International Patent Publications referred to above contain detailed examples of the preparation and testing of pharmaceutical formulations containing CYSC polymers. Those examples can be repeated, replacing the drugs used therein by other release materials and making corresponding modifications, to illustrate release compositions containing CYSC polymers and other drugs and other release materials which are not drugs.

Examples EC1-EC10

Examples EC1-EC10 describe the preparation of ECC polymers, and are summarized in Table EC1 below. Table EC1 identifies the starting materials and the amounts thereof in grams, and molecular weight and DSC characteristics of the various products. In the PLGA polymers used in the Examples, the molar ratio of (units derived from) GA to LA was 1:1. After the Table, there is a detailed account of the procedures used in each of Examples EC1-EC10. The heading of each detailed example includes an abbreviation indicating the polymer produced in the example, in the form "PLGA", indicating that the polymer is an unmodified PLGA [in comparative Example EC1(C)], or "nECC-PLGA", where n is 1, 2, 3, 4 or 6, indicating that the polymer is an end-capped PLGA containing 1, 2, 3, 4 or 6 Cy moieties.

TABLE EC1

| Ex. #.  | EC1     | EC1(C)  | EC2      | EC3       | EC4     | EC5    | EC6(a) | EC6(b) |
|---------|---------|---------|----------|-----------|---------|--------|--------|--------|
| #       | 341-1-3 | 341-1-0 | 338-80   | 341-41-5R | 338-55  | 338-56 | 338-75 | 338-77 |
| GA      | 51.925  | 57.011  | —        | 55.53     | —       | —      | —      |        |
| LA      | 70.291  | 77.175  | —        | 75.18     | —       | —      | —      |        |
| C6 PLGA |         |         |          |           | 5.034   | —      | —      |        |
| C22 A   | 11.15   | —       | —        | —         | —       | —      | —      |        |
| C22 OH  | —       | —       | —        | 5.53      | 1.145   | 2.071  | —      | 1.272  |
| EC1     | —       | —       | 16.055   | —         | —       | 5.033  | —      |        |
| SUCAN   | —       | —       | 2.002    | —         | —       | —      | —      |        |
| EC2     | —       | —       | —        | —         | —       | —      | 6.73   |        |
| Glycerol| —       | —       | —        | —         | —       | —      | 60 mL  |        |
| EC6(a)  | —       | —       | —        | —         | —       | —      |        | 1.27   |
| To      |         |         | 50.55    |           | 45.95   | 54.77  |        | 52.11  |
|         |         |         | Tg16.2   |           |         |        |        |        |
| Tp      | 58      | Tg18.7  | 57.06    | 59.8      | 54.17   | 59.89  |        | 58.46  |
|         |         |         | Tg19.2   |           |         |        |        |        |
| Mn      | 812     | 1165    | 633      | 665       | 4986    | 3912   |        | 6091   |
| Mw      | 981     | 1484    | 879      | 1184      | 7080    | 7119   |        | 14,235 |

| Ex. #.  | EC7(a)  | EC7(b)  | EC8     | EC9(a)  | EC9(b)  | EC9(c)  | EC10(a) | EC10(b) |
|---------|---------|---------|---------|---------|---------|---------|---------|---------|
| ID #    | 338-91  | 338-93  | 338-92  | 338-85  | 338-87  | 338-88  | 338-83  | 338-84  |
| C22 acid|         | 2.044   |         |         |         | 2.504   |         | 1.583   |
| SUCAN   |         |         |         |         | 1.465   |         |         |         |
| EC1(C)  |         |         |         |         | 15.027  |         |         |         |
| EC2     |         |         |         |         |         |         | 7.049   |         |
| Glycerol| 35 mL   |         | 0.282   |         | 25 mL   |         | 30 mL   |         |
| EC3     | 15.077  |         | 8.133   |         |         |         |         |         |
| EC7(a)  |         | 3.16    |         |         |         |         |         |         |
| EC9(a)  |         |         |         |         |         | 9.85    |         |         |
| EC9 (b) |         |         |         |         |         |         | 2.2     |         |
| EC10(a) |         |         |         |         |         |         |         | 1.86    |
| To      |         | 56.69   | 25.37(1)|         |         | 51.34   |         | 51.54   |
|         |         | Tg9.96  | 44.48(2)|         |         |         |         |         |
| Tp      |         | 60.35   | 30.72(1)|         |         | 57.16   |         | 57.15   |
|         |         | Tg18.97 | 49.29(2)|         |         |         |         |         |
| Mn      |         | 4774    | 2479    |         |         | 45,370  |         | 6893    |
| Mw      |         | 18,385  | 3373    |         |         | 160,900 |         | 15,545  |

Example EC1

Preparation of 1ECC-PLGA (ID #341-1-3)

The GA, LA and C22OH were placed in a 1000 mL vessel equipped with a mechanical stirrer and heated to 140° C. After stirring for 15 to 25 min, vacuum was applied to remove water. The reaction was continued under reduced pressure at 140° C. for at least 16 hrs. A clear pale yellow viscous liquid was removed from the vessel while it was still hot. After cooling to room temperature, 85 gram of opaque solid (341-1-3) was obtained.

Example EC1(C)

Preparation of PLGA (ID #341-1-0)

The GA and LA were reacted following the procedure of Example EC1. A clear solid, 84 g, (341-1-0) was obtained.

Example EC2

Preparation of 1ECC-PLGA (ID #338-80)

The ECC-PLGA (ID # 341-1-3) and SUCAN (molar ratio of 1:1), and a catalytic amount of PTSA were combined with 200 mL toluene in a 250 mL round bottom flask fitted with a condenser and Dean-Stark trap. The mixture was stirred under reflux with a magnetic stir bar under nitrogen in a 135° C. oil bath overnight. The temperature was increased to 150° C. and stirring continued for 2 days, after which toluene was removed by distillation over 4.5 hours. Reaction progress was monitored by FTIR through loss of anhydride peaks at 1864 cm-1 and 1782 cm-1, loss of broad PLGA alcohol peak from 3600-3400 cm-1, and increase in broad acid OH peak from 3300-2400 cm-1. The product was purified by first dissolving in 50 mL warm DCM and adding 50 mL water. The layers were separated in a separatory funnel and the water layer was extracted 1× with 25 mL DCM. The organic layers were combined and washed 3× with 25 mL water. The DCM layer was dried over anhydrous magnesium sulfate which was removed by gravity filtration. The resulting filtrate was condensed under reduced pressure to give 16.3 g of product (338-80).

Example EC 3

Preparation of 1ECC-PLGA (ID #341-41-5R)

The GA (55.53 g), LA (75.18 g) and C22 acid (5.53 g) were reacted following the procedure of Example EC1. An opaque solid, 90 g, (341-41-5R) was obtained.

Example EC4

Preparation of 2ECC-PLGA (ID #338-55)

The PLGA (polymer having Mn 3127 obtained from Durect, Pelham, Ala.) and the C22 acid (molar ratio 1:2) and a catalytic amount of PTSA were combined in a 100 mL round bottom flask with 30 mL toluene. The mixture was stirred with a magnetic stir bar under nitrogen and heated for 1 hour until all solids dissolved and the toluene was refluxing. Toluene was removed under reduced pressure over 4 hours followed by continued heating under nitrogen at 140° C. for 3.5 days until completely reacted. Reaction progress was monitored by FTIR through loss of the 1708 cm-1 carboxylic acid carbonyl peak and conversion to an ester carbonyl peak at about 1757 cm-1 (overlap with PLGA ester carbonyl at the same shift), and loss of the broad acid OH peak from 3300-2400 cm-1. The product was purified by first dissolving in 35 mL of warm DCM followed by cooling for 5-10 minutes on dry ice until visibly cloudy with a white precipitate. Gravity filtration over fluted filter paper was performed to remove a white solid. Solvent was removed from the solution under reduced pressure yielding 4.3 grams of product (338-55).

Example EC5

Preparation of 2ECC-PLGA (ID #338-56)

The polymer ID #341-1-3 and the C22 acid (molar ratio 1:1) and a catalytic amount of PTSA were placed in a 250 mL round bottom flask with 50 mL toluene. The mixture was stirred with a magnetic stir bar under nitrogen in a 140° C. oil bath for a quarter hour until all solids dissolved. Toluene was removed under reduced pressure over 2.5 hours followed by continued heating under nitrogen at 140° C. for 3.5 days until completely reacted. Reaction progress was monitored by FTIR as in Example EC4. Any residual toluene was removed under reduced pressure for 1 hour. The product was purified by first dissolving in 40 mL of warm DCM followed by cooling for 5-10 minutes on dry ice until cloudy with white precipitate. Gravity filtration over fluted filter paper was performed to remove a white solid. Solvent was removed from the solution under reduced pressure yielding 3.5 grams of product (338-56).

Example EC6

Preparation of 3ECC-PLGA (ID #338-77)

(a) The polymer ID #338-80 and the glycerol were combined in a 250 mL round bottom flask. The reaction was stirred with a magnetic stir bar under nitrogen in a 130° C. oil bath overnight, until reacted. Reaction progress was monitored by taking small samples of the reaction mixture and extracting with DCM, and monitoring by FTIR through the loss of the broad acid OH peak between 3200-2400 cm-1 and the appearance of the glycerol alcohol peak from 3600-3100 cm-1. The product was purified by addition of 100 mL DCM and 100 mL water, stirred and shaken vigorously, and added to a separatory funnel. The resulting layers were separated, and the water layer extracted 3× with 50 mL DCM. The organic layers were combined and washed 3× with 20 mL water, and then dried over anhydrous magnesium sulfate, which was subsequently removed by gravity filtration through fluted filter paper. This extraction and washing process was repeated on the water layers a second time to remove any remaining product, with all resulting organic layers combined and solvent removed under reduced pressure to yield 1.27 grams of intermediate product (ID #338-75).

(b) The intermediate product ID #338-75 and the C22 acid, and a catalytic amount of PTSA and 200 mL toluene when mixed in a 250 mL round bottom flask fitted with a Dean Stark trap. The mixture was stirred under reflux with a magnetic stir bar under nitrogen in a 130° C. oil bath overnight. The temperature was then increased to 135° C. and stirred under reflux for 24 hours until complete. Reaction progress was monitored by the loss of the broad glycerol OH peak from 3600-3100 cm-1, the disappearance of the broad acid OH stretch from 3200-2400 cm-1, and the loss of the C22 acid carbonyl peak at 1706 cm-1 and conversion to ester carbonyl peak at about 1754 cm-1 (overlap with PLGA ester carbonyl peaks). The product was purified by dissolving in warm DCM and cooled over dry ice for 5-10 minutes until a white precipitate was formed, which was removed by gravity filtration through fluted filter paper. The filtrate was condensed under reduced pressure to produce 1.93 g of product (ID #338-77).

Example EC7

Preparation of 3ECC-PLGA (ID #338-93

(a) The polymer ID #341-41-R, the glycerol (large molar excess) and a catalytic amount of PTSA were combined in a 100 mL round bottom flask. The mixture was stirred by magnetic stir bar under nitrogen and heated in a 130° C. oil bath overnight until reaction was complete. Reaction progress was monitored by taking small samples of reaction mixture and performing a mini-extraction with DCM, with progress monitored through FTIR through the loss of broad acid OH peak from 3300-2300 cm-1 and appearance of broad glycerol OH peak from 3700-3100 cm-1 in product. For purification 50 mL water and 20 mL DCM was added to the reaction flask, warmed, and stirred vigorously until all was dissolved. Using a separatory funnel, the organic layer was isolated and the water layer extracted 2× with 30 mL DCM. The organic layers were then combined and washed 3× with 20 mL water, then dried over anhydrous magnesium sulfate which was then removed by gravity filtration through fluted filter paper. Solvent was removed under reduced pressure to give 3.42 g reaction intermediate (ID #338-91).

(b) The reaction intermediate ID #338-91 and the C22 acid (molar ratio about 1:2.4), 65 mL toluene, and a catalytic amount of PTSA were combined in a 100 mL round bottom flask fitted with condenser and Dean-Stark trap. The mixture was stirred by magnetic stir bar under nitrogen and placed in a 135° C. oil bath, and allowed to reflux for 4.5 days until reaction was complete and yielded approximately 4 grams of product (ID #338-93). Reaction progress was monitored by FTIR through the loss of broad glycerol OH peak from 3700-3100 cm-1, loss of broad C22 acid OH peak from 2800-2300 cm-1, and loss of C22 acid carbonyl peak at 1707 cm$^{-1}$ and strengthening of 1750 cm$^{-1}$ ester peak due to acid conversion to ester bond.

Example EC8

Preparation of 3ECC-PLGA (ID #338-92)

The polymer ID #341-41-5R and the glycerol (molar ratio about 2.25:1) and a catalytic amount of PTSA were combined in a 3 neck 250 mL round bottom flask. The reaction was stirred by magnetic stir bar and heated under nitrogen in a 135° C. oil bath. The reaction was stirred for 1.5 days until reaction was complete and removed from heat to produce the final product (ID #338-92). Reaction progress was monitored by FTIR through the loss of the broad acid OH peak especially from 2800-2400 cm-1, the loss of the glycerol OH peak from 3700-3100 cm-1, and the slight shift of acid carbonyl peak from 1749 cm-1 to 1753 cm-1 due to ester formation (overlap with PLGA ester carbonyl peaks).

Example EC9

Preparation of 4ECC-PLGA (ID #338-88

(a) The polymer ID #341-1-0 and the SUCAN (molar ratio 1:1.1) and 150 mL toluene were mixed in a 250 mL round bottom flask fitted with a condenser and Dean-Stark trap. The mixture was stirred by magnetic stir bar under nitrogen in a 135° C. oil bath while refluxing. The mixture was stirred for 3 days until fully reacted. Reaction progress was monitored by FTIR through the loss of SUCAN peaks at 1864 cm-1 and 1782 cm-1 and loss of PLGA OH peaks from 3700-3300 cm-1. For purification about 50 mL warm DCM and about 50 mL water were added to the reaction flask and stirred vigorously. The layers were then separated by separatory funnel, with the water layer extracted 2 times each with 30 mL with DCM. The DCM layers were combined and then washed with about 30 mL of water once only. The resulting organic layers were dried over anhydrous magnesium sulfate that was subsequently removed by gravity filtration through fluted filter paper. Solvent was removed under reduced pressure to yield 15.08 g of Intermediate 1 (ID #338-85).

(b) The intermediate ID #338-85 and the glycerol (large excess) were combined in a 250 mL round bottom flask. The mixture was stirred by magnetic stir bar under nitrogen in a 130° C. oil bath for 20 hours until complete. Reaction progress was monitored by FTIR through loss of the broad acid OH peak between 3200-2500 cm-1 and the appearance of the glycerol alcohol peak from 3700-3200 cm-1. The reaction was purified by adding ~50 mL warm DCM and ~50 mL water to the flask and stirring vigorously. The layers were then separated in a separatory funnel, and the water layer extracted 2 times each with 50 mL DCM. All organic layers were combined and washed 3 times each with ~40 mL of water. The organic layer was then dried over anhydrous magnesium sulfate, which was then removed from gravity filtration through fluted filter paper. Solvent was removed under reduced pressure to give 2.41 g of Intermediate 2 (ID #338-87).

(c) The intermediate ID #338-87 and the C22 acid (molar ratio 1:4.5) and a catalytic amount of PTSA were combined in a 250 mL round bottom flask with 150 mL toluene. The mixture was stirred with a magnetic stir bar under nitrogen and stirred in a 135° C. oil bath under reflux, while fitted with a condenser and Dean-Stark trap. The mixture was stirred overnight, at which point solvent was drained and the flask placed under reduced pressure to remove the remaining toluene. The reaction was then stirred in the 135° C. oil bath under nitrogen for 24 hours until complete and removed from heat. The reaction progress was monitored by FTIR through the loss of the broad glycerol OH peak from 3700-3200 cm-1, the loss of the broad acid OH stretch from 3100-2400 cm-1, and the loss of the C22 acid carbonyl peak at 1703 cm-1 and conversion to ester carbonyl peak at about 1757 cm-1 (overlap with PLGA ester carbonyl peaks). The product was purified by dissolving the sample in warm DCM to dissolve and cooled over dry ice for 5-10 minutes until cloudy with white precipitate. Precipitate was removed by gravity filtration through fluted filter paper and the filtrate was condensed under reduced pressure to produce the final product (ID #338-88) with yield of 2.91 g.

Example EC10

Preparation of 3ECC-PLGA (ID #338-84)

The procedure of Example EC6 was followed, but using the product from Example EC2 (338-80, 7.049 g) and 30 mL of glycerol to obtain intermediate 338-83. The intermediate 338-83 (1.86 g) was reacted with C22 acid (1.583 g) as in Example EC6 until the reaction was complete. After purification, 2.84 g of product (338-84) was obtained.

Preparation and Testing of Pharmaceutical Formulations Containing ECC Polymers and Comparative Polymers.

Mixtures of drug (either risperidone or diclofenac sodium) and polymer were prepared at 9.1% drug loading by mixing the drug with the polymer in TCM at the ratio of drug/polymer/TCM=1/10/35 (wt/wt/wt) at 70° C., followed by evaporation of TCM in a 70° C. oven, and removal of residual TCM under reduced pressure at 70° C. The drug/polymer mixtures formed a single phase above the Tp of the polymer. Release samples were prepared as a thin flat disc in a 20 mL scintillation vial (28×61 mm=OD×H) by loading 0.5 gram of the prepared polymer/drug mixture into the vial and warming to 65-80° C., allowing the mixture to flow and fuse together. After cooling the mixture to a temperature below Tp, a solid disc with a smooth uniform surface formed at the bottom of the vial.

Release Test for Risperidone Samples

The risperidone samples were tested by covering the polymer/drug disc with 12.6 grams of a buffer solution at pH=5.5 (50 mM ionic strength, 150 mM NaCl and containing 0.01% w/v Tween-20). The buffer solution was removed and replaced by 12.6 grams of fresh buffer solution at scheduled sampling times, e.g. at 1 min, 2 hr, 6 hr, daily, weekly, or as necessary. The amount of risperidone released into the sample solution was measured by UV-Vis against a standard curve established by using the absorption signal at $\lambda$=276.93 nm.

The buffer solution used to test the risperidone/polymer samples was prepared by adding to 100 mL DI water, 0.16 g of monosodium phosphate monohydrate and 1.04 g disodium phosphate, followed by NaCl and Tween-20 to a final concentration of 0.9% and 0.01% w/v, respectively. The pH was adjusted to 5.5 with 0.1N HCl as necessary.

Release Test for Diclofenac Sodium Samples

The diclofenac sodium samples were tested by covering the polymer/drug with 5 grams of buffer solution with pH=7.4 (50 mM ionic strength, 150 mM NaCl and containing 0.01% w/v Tween-20). The buffer solution was removed and replaced by 5 grams of fresh buffer solution at scheduled sampling times, e.g. at 1 min, 2 hr, 6 hr, daily, weekly, or as necessary. The amount of diclofenac sodium released into the sample solution was measured by UV-Vis against a standard curve established by using the absorption signal at $\lambda$=276.93 nm.

The buffer solution used to test the diclofenac sodium samples was the same as that used to test the risperidone polymer samples, except that its pH was adjusted to 7.4 with 0.1N HCl or 0.1N NaOH as necessary.

FIGS. 1-8

Figure 1B:
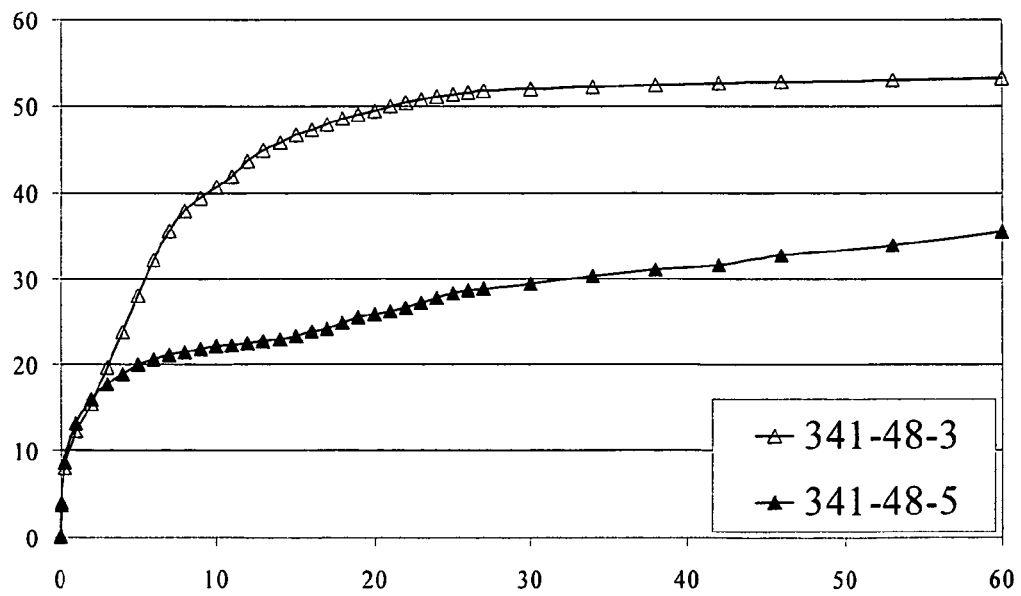
FIG. 1b shows, on the vertical axis, the cumulative release of diclofenac sodium from test sample ID #341-48-3 based on a commercially available unmodified PLGA, and from test sample 341-48-5 based on polymer ID#341-1-3 prepared in Example EC1, and, on the horizontal axis, the time in days.
Figure 2:
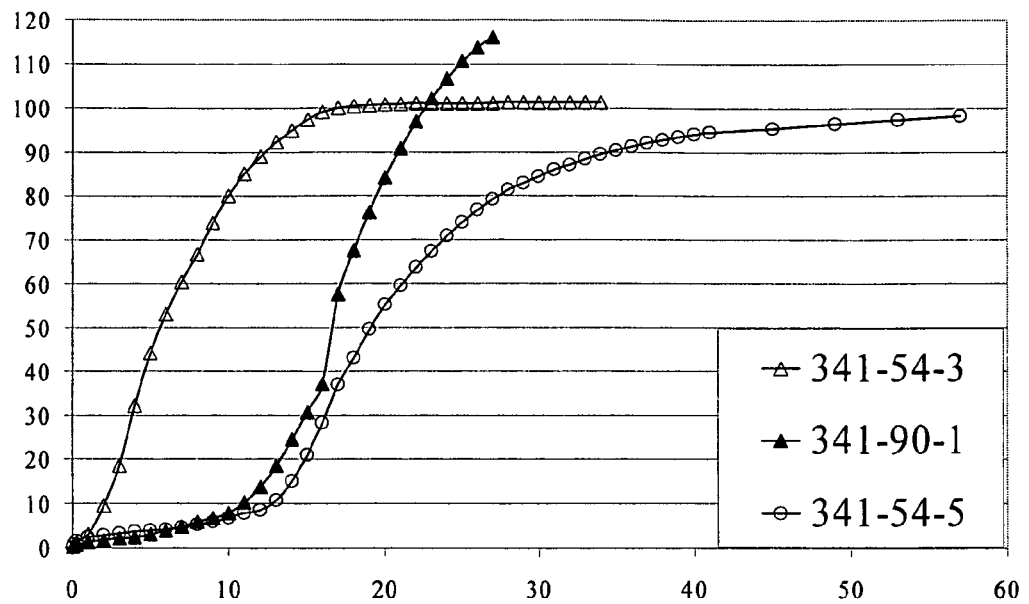
FIG. 2 shows, on the vertical axis, the cumulative release of risperidone from test sample ID #341-54-3 (above), from test sample ID #341-90-1, based on polymer ID #338-80 prepared in Example EC3, and from test sample #341-54-5 based on polymer ID #341-1-3 prepared in Example EC1, and, on the horizontal axis, the time in days.
Figure 3:
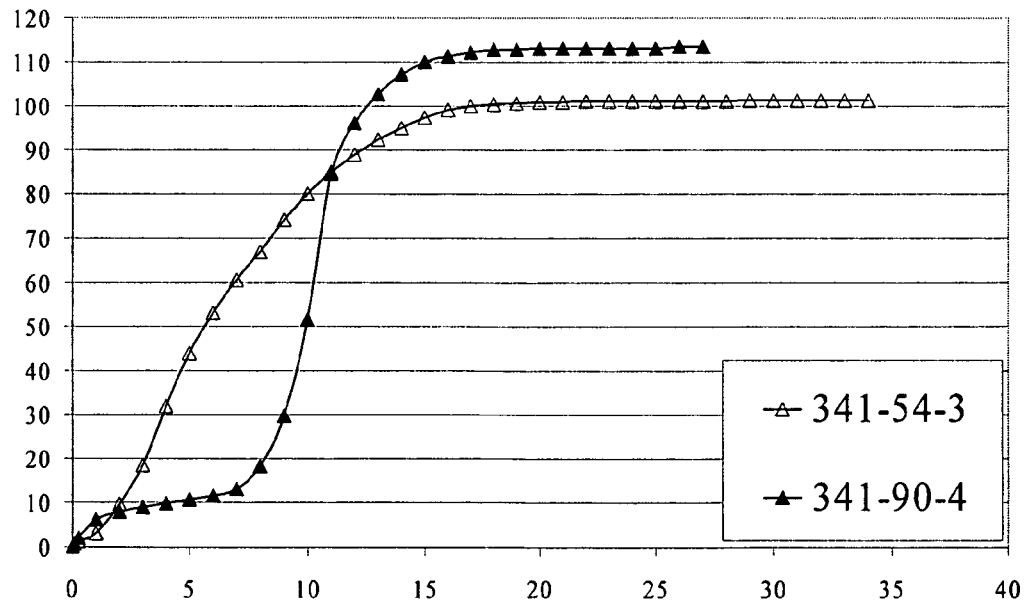
FIG. 3 shows, on the vertical axis, the cumulative release of risperidone from test sample #341-54-3 (above) and from test sample 341-90-4 based on polymer ID number 341-41-5R prepared in Example EC 3, and, on the horizontal axis, the time in days.
Figure 4:
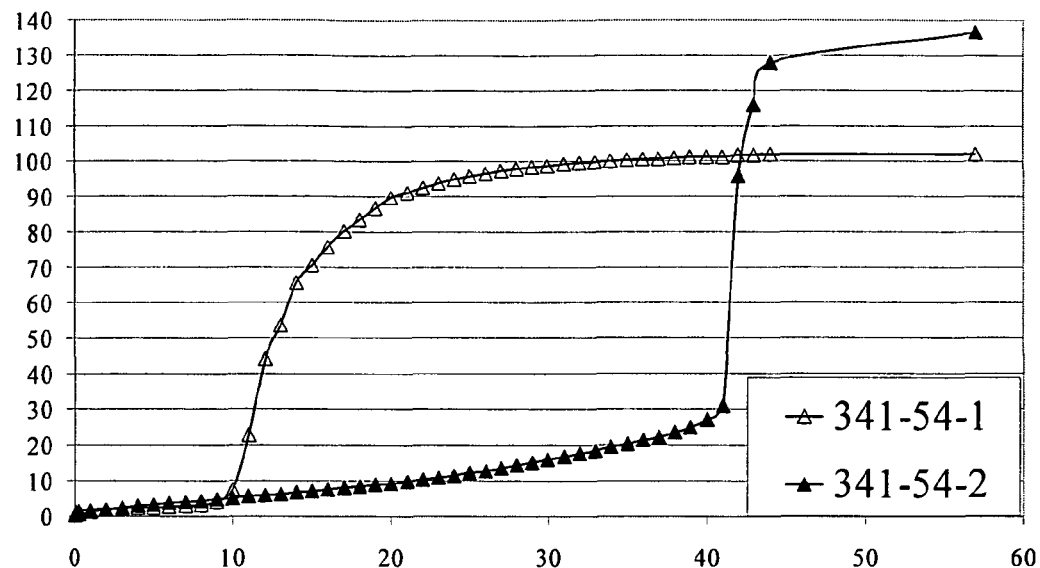
FIG. 4a shows, on the vertical axis, the cumulative release of risperidone from test sample ID #341-54-1 based on a commercially available unmodified PLGA, and from test sample ID #341-54-2, based on polymer ID number 338-55 prepared in Example EC 4, and, on the horizontal axis, the time in days.
FIG. 4b shows, on the vertical axis, the cumulative release of diclofenac sodium from test sample ID #341-48-1 and from test sample ID #341-48-2 based on polymer ID #338-55, prepared in Example EC 4, and, on the horizontal axis, the time in days.
Figure 4B:
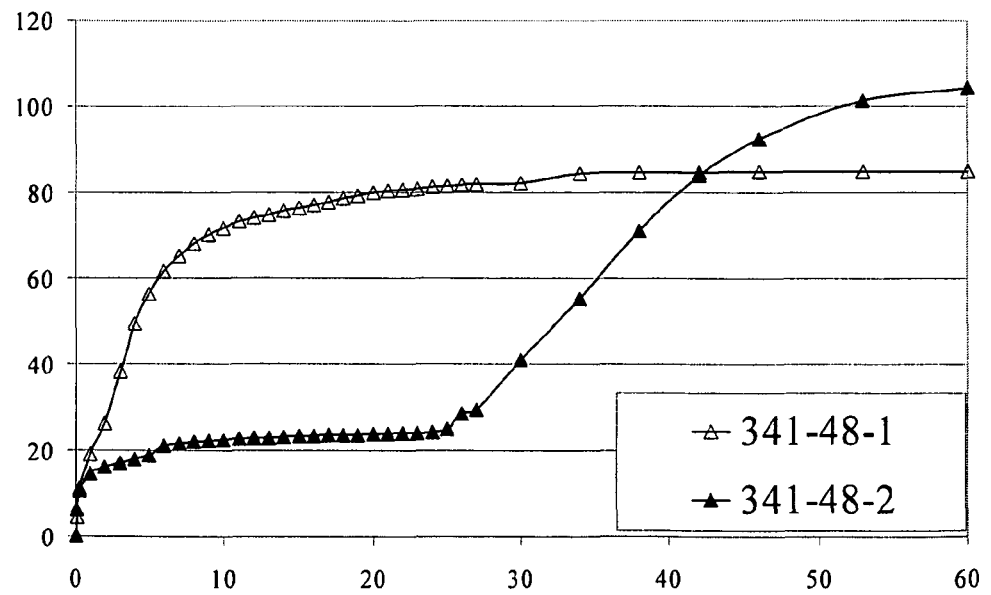
Figure 5A:
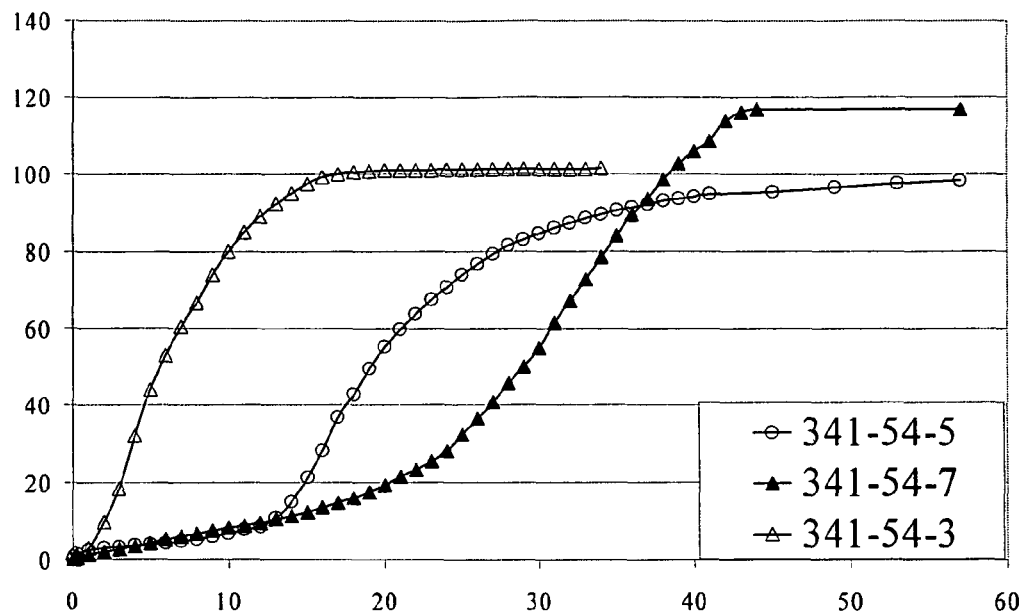
FIG. 5a shows, on the vertical axis, the cumulative release of risperidone from test sample #341-54-5 based on polymer ID #341-1-3 prepared in Example EC1, from test sample ID #341-54-7 based on polymer ID #338-56 prepared in Example EC5, and from test sample ID #341-54-3 (above), and, on the horizontal axis, the time in days.
Figure 5B:
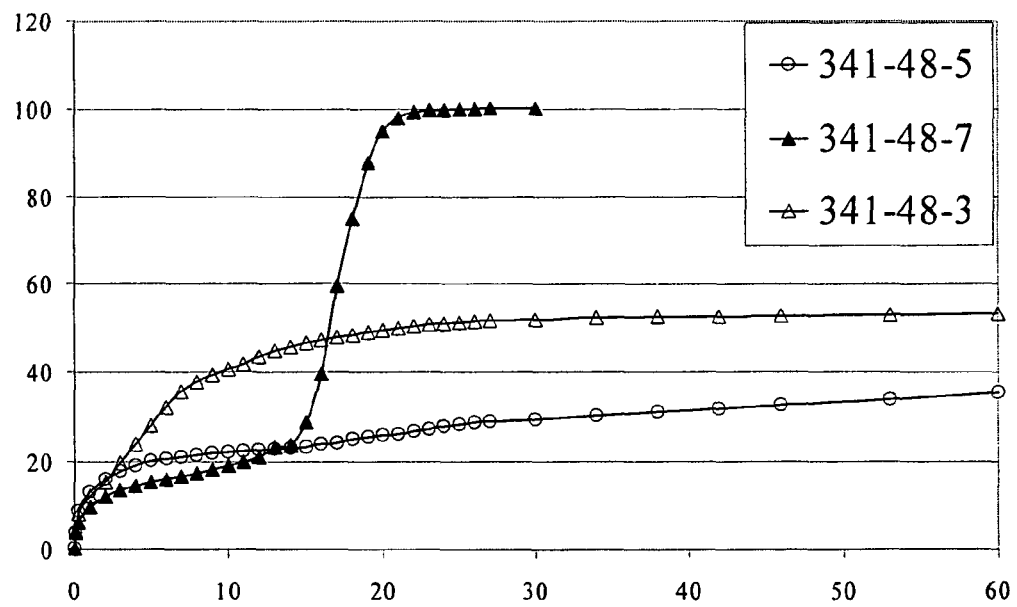
FIG. 5b shows, on the vertical axis, the cumulative release of risperidone from test sample #341-54-5 based on polymer ID #341-1-3 prepared in Example EC1, from test sample ID #341-54-7 based on polymer ID #338-56 prepared in Example EC5, and from test sample ID #341-54-3 (above), and, on the horizontal axis, the time in days.
Figure 6:
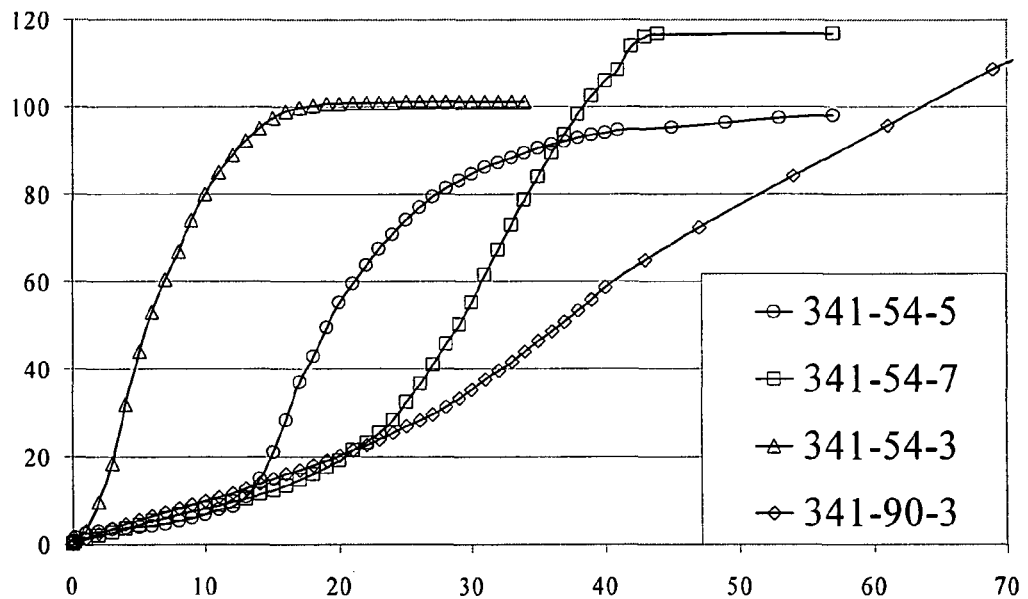
FIG. 6 shows, on the vertical axis, the cumulative release of risperidone from test sample ID #341-54-5 based on polymer ID #341-1-3 prepared in Example EC1, from test sample ID #341-54-7 based on polymer ID #338-56 prepared in Example EC5, from test sample ID #341-54-3 based on polymer ID #341-1-0, prepared in Example EC1 (C), and from test sample #341-90-3 based on polymer ID #341-1-3 prepared in Example EC1, and, on the horizontal axis, the time in days.
Figure 7:
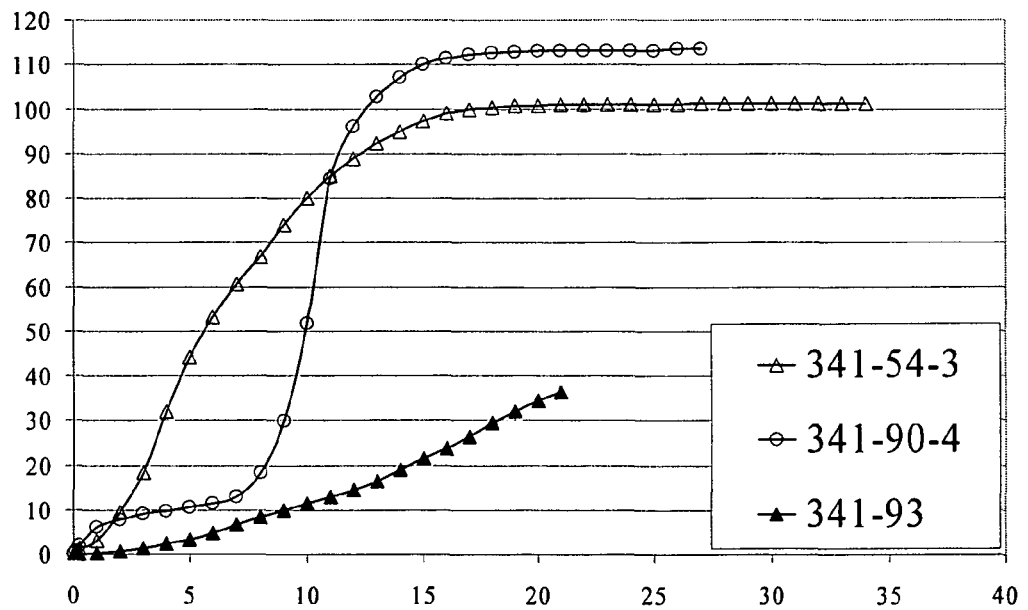
FIG. 7 shows, on the vertical axis, the cumulative release of risperidone from sample ID #341-54-3 based on polymer ID #341-1-0 prepared in Example EC1(C), from sample ID #341-90-4 based on polymer ID #341-41-5R prepared in Example EC3, and from test sample ID #341-93 based on polymer ID #338-93 prepared in Example EC7, and, on the horizontal axis, the time in days.
Figure 8:
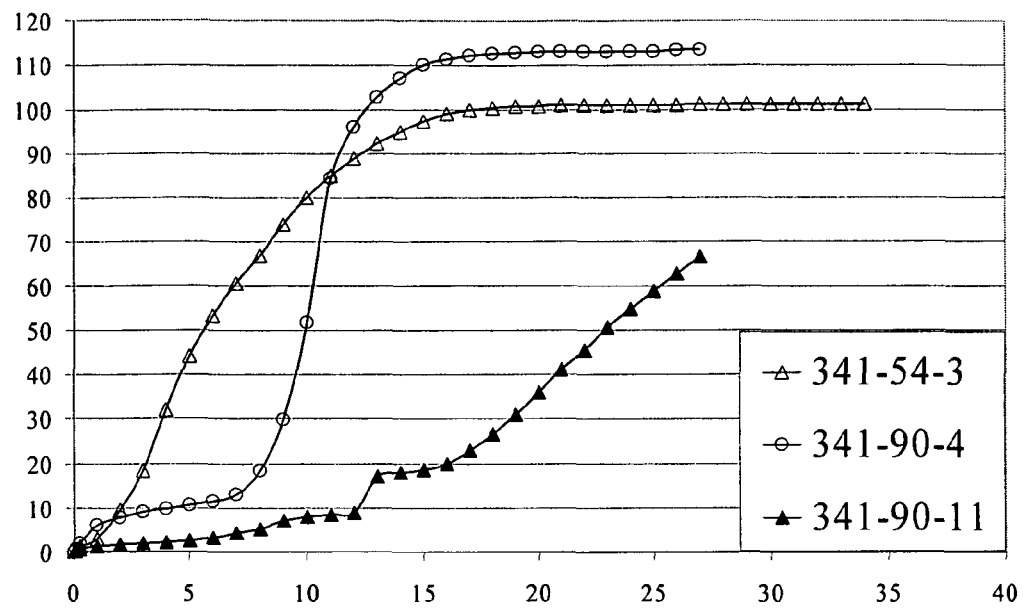
FIG. 8 shows, on the vertical axis, the cumulative release of risperidone from test sample ID #341-54-3 based on polymer ID #341-1-0, prepared in Example EC1, from test sample ID #341-90-4 based on polymer ID #341-41-5 R prepared in Example EC3, and from test sample ID #341-90-11 based on polymer ID #338-92, prepared in Example EC8, and, on the horizontal axis, the time in days.

The results of the testing are shown in FIGS. 1-8, in which the vertical axis shows the total percentage release ("cumulative release") of the drug, and the horizontal axis shows the time in days. Thus, the Figures show the cumulative release of (i) in FIG. 1a, risperidone from test sample ID #341-54-3 based on the unmodified PLGA polymer ID #341-1-0 prepared in Example EC1(C); and test sample ID #341-54-5, based on polymer ID #341-1-3 prepared in Example EC 1;

(ii) in FIG. 1b, diclofenac sodium from test sample ID #341-48-3 based on a commercially available unmodified PLGA, and from test sample 341-48-5 based on polymer ID#341-1-3 prepared in Example EC1;

(iii) in FIG. 2 risperidone from test sample ID #341-54-3 (above), from test sample ID #341-90-1, based on polymer ID #338-80 prepared in Example EC3, and from test sample #341-54-5 based on polymer ID #341-1-3 prepared in Example EC1;

(iv) in FIG. 3, risperidone from test sample #341-54-3 (above) and from test sample 341-90-4 based on polymer ID number 341-41-5R prepared in Example EC 3;
(v) in FIG. 4a, risperidone from test sample ID #341-54-1 based on a commercially available unmodified PLGA, and from test sample ID #341-54-2, based on polymer ID number 338-55 prepared in Example EC 4;
(vi) in FIG. 4b, diclofenac sodium from test sample ID #341-48-1 (above) and from test sample ID #341-48-2 based on polymer ID #338-55, prepared in Example EC 4;
(vii) in FIG. 5a, risperidone from test sample #341-54-5 based on polymer ID #341-1-3 prepared in Example EC1, from test sample ID #341-54-7 based on polymer ID #338-56 prepared in Example EC5, and from test sample ID #341-54-3 (above);
(viii) in FIG. 5b, diclofenac sodium from test sample #341-48-5 based on polymer ID #341-1-3 prepared in Example EC1, from test sample #341-48-7, based on polymer ID #338-56 prepared in Example EC5, and from test sample ID #341-48-3 based on polymer ID #341-1-0 prepared in Example EC1 (C);
(ix) in FIG. 6, risperidone from test sample ID #341-54-5 based on polymer ID #341-1-3 prepared in Example EC1, from test sample ID #341-54-7 based on polymer ID #338-56 prepared in Example EC5, from test sample ID #341-54-3 based on polymer ID #341-1-0, prepared in Example EC1 (C), and from test sample #341-90-3 based on polymer ID #341-1-3 prepared in Example EC1;
(x) in FIG. 7, risperidone from sample ID #341-54-3 based on polymer ID #341-1-0 prepared in Example EC1(C), from sample ID #341-90-4 based on polymer ID #341-41-5R prepared in Example EC3, and from test sample ID #341-93 based on polymer ID #338-93 prepared in Example EC7; and
(x) in FIG. 8, risperidone from test sample ID #341-54-3 based on polymer ID #341-1-0, prepared in Example EC1, from test sample ID #341-90-4 based on polymer ID #341-41-5 R prepared in Example EC3, and from test sample ID #341-90-11 based on polymer ID #338-92, prepared in Example EC8.

Examples EC11-EC13

Examples EC11-EC13 illustrate the preparation of CYC compounds, and are summarized in Table EC 2 below, which shows the starting materials and the amounts thereof in grams, the residual amount of the C22 acid, and the DSC characteristics of the products.

In Examples 11A-11F, the C22 acid and D-sorbitol (in the percentages and molar ratios shown in Table EC2), and a catalytic amount of PTSA were placed in a 1000 mL vessel equipped with a stirrer. The vessel was heated in a 120-140° C. oil bath. After stirring for about 30 minutes, a cloudy two-phase liquid formed. The reaction was continued under reduced pressure at 120-140° C. for at least 16 hours. A clear light yellow-brown one-phase liquid formed and was removed while hot. Some dark particles were formed during the reaction as a result of decomposition of the sorbitol. After cooling to room temperature, an off-white or light brown opaque solid was obtained.

In Examples 12A-12C, the C22 acid and the glycerol (in the percentages and molar ratios shown in Table EC2) and a catalytic amount of PTSA were placed in a 1000 mL vessel equipped with a stirrer. After stirring for about 30 minutes, a cloudy two-phase liquid formed. The reaction was continued under reduced pressure in a 120° C. bath (Examples 12A and 12B) or a 140° C. bath (Example 12C) for at least 16 hours. A clear light yellow-light brown one-phase liquid formed, and was removed while hot. After cooling, a light yellow or light brown opaque solid was obtained. In Example 13, the C22OH and the boc-Asp (boc-protected aspartic acid (in the amounts in grams and molar ratio shown in Table EC2), a catalytic amount of PTSA and 200 mL of toluene were placed in a 250 mL three necked round bottom flask fitted with a condenser and Dean-Stark trap. The vessel was heated in a 140° C. oil bath, with stirring, under nitrogen in refluxing toluene, for 3.5 days, by which time most of the toluene had been removed. Reaction progress was monitored by FTIR through loss of the broad acid OH peak from 3300-2600 $cm^{-1}$ and shifting of the acid carbonyl peak from 1697 $cm^{-1}$ to 1726 $cm^{-1}$ due to formation of the ester bond. The remaining toluene was removed under reduced pressure at 125° C. to yield 15.73 g of final product. The product had an Mn of 887 (which is consistent, within the margin of error, with the expected Mn of 850).

Examples EC14-EC17

Examples EC14-EC17 illustrate the preparation of CYSC block copolymers, and are summarized in Table EC3 below, which shows the starting materials and the amounts thereof in grams, the yield in grams, and Mn, Mw and DSC characteristics of the products.

TABLE EC2

| Ex #EC | 11A | 11B | 11C | 11D | 11E | 11F | 12A | 12B | 12C | 13 |
|---|---|---|---|---|---|---|---|---|---|---|
| ID #341- | 55-1 | 55-2 | 55-3 | 55-4 | 55-5 | 55-6 | 62-1 | 62-2 | 62-3 | |
| ID #338- | | | | | | | | | | 73 |
| C22Acid | 68.5 | 80.6 | 86.2 | 89.3 | 91.2 | 92.6 | 80.4 | 89.2 | 92.5 | |
| C22OH | | | | | | | | | | 14.3 |
| SORB | 32.5 | 19.4 | 13.8 | 10.7 | 8.8 | 7.4 | | | | |
| Glycerol | | | | | | | 19.6 | 10.8 | 7.5 | |
| boc-Asp | | | | | | | | | | 4.7 |
| Molar | 1/1 | 2/1 | 3/1 | 4/1 | 5/1 | 6/1 | 1/1 | 2/1 | 3/1 | 2.2/1 |
| Yield | 81 | 91 | 90 | 90 | 94 | 92 | 82 | 91 | 95 | |
| Residual | 7.8 | 16.2 | 16.2 | 28.4 | 23.0 | 28.7 | 10 | 21 | 20 | |
| Tp | 63.3 | 62.5 | 62.7 | 61.6 | 63.4 | 76.0 | 71.7 | 70.6 | 69.6 | 59.31 |
| | | 74.6 | 70.2 | 72.8 | 76.3 | 75.4 | | | | 69.72 |
| To | | | | | | | | | | 54.22 |
| | | | | | | | | | | 67.49 |

TABLE EC 3

|  | Ex #EC | | | |
|---|---|---|---|---|
|  | 14 | 15 | 16 | 17 |
| ID #341- | 89 | 85 | 86 | 82 |
| CYSC polymer ID #321-100-1 | 4.78 | | 7.9 | |
| CYSC polymer ID #326-1-1 | | 4.78 | | 7.9 |
| ECC-PLGA ID #341-41-5R | | | 2.1 | |
| ECC-PLGA ID #341-1-3 | | | | 2.1 |
| GA | 55.65 | 55.65 | | |
| LA | 75.33 | 75.33 | | |
| Yield | 86 | 88 | 8.4 | 7.8 |
| Mn | 2785 | 1221 | 12,310 | 2798 |
| Mw | 4654 | 1568 | 53,980 | 3395 |
| Tp | | | 62.9 | 46.0 | 62.6 | 46.6 |
| Tg | 17.3 | 3.7 | | |

CYSC polymer ID #321-100-1 is a copolymer of C22A and HEA (2-hydroxyethyl acrylate) in a weight ratio of 82/18, and has an Mw of 8151. CYSC polymer ID #326-1-1 is a copolymer of C18A and acrylic acid in a weight ratio of 95/5 and has an Mw of 3012. ECC-PLGA ID #341-41-5R is the carboxyl functional ECC-PLGA prepared in Example EC 3 above. ECC-PLGA ID #341-1-3 is the hydroxyl functional ECC-PLGA prepared in Example EC1 above.

Example EC14

Preparation of CYSC-PLGA Block Copolymer (ID #341-89)

The CYSC polymer, GA and LA were mixed in a 1000 ML vessel equipped with a stirrer. The vessel was heated in a 140° C. oil bath. After stirring for 15-25 minutes, vacuum was applied to remove water. The reaction was continued under reduced pressure in the 140° C. bath for at least 16 hours. A clear colorless viscous liquid was removed from the reactor while it was still hot. After cooling to room temperature, the product was obtained as an opaque solid.

Example EC15

Preparation of CYSC-PLGA Block Copolymer (ID #341-85)

The procedure of Example 14 was followed, and the product was obtained as an opaque solid.

Example EC16

Preparation of CYSC-PLGA Block Copolymer (ID #341-86)

The CYSC polymer, the carboxyl functional ECC-PLGA, toluene (140 g) and a catalytic amount of PTSA where mixed in a 1000 mL vessel equipped with a stirrer. The vessel was heated in a 150° C. oil bath for about 6 hours while refluxing toluene under a nitrogen blanket, to remove water generated during the reaction. Excess toluene was removed by distillation, followed by vacuum distillation at 120° C. The reaction was continued in the 120° C. bath overnight. A translucent one phase colorless viscous liquid was removed from the reactor while it was still hot. After cooling to room temperature, the product was obtained as an opaque solid.

Example EC17

Preparation of CYSC-PLGA Block Copolymer (ID #341-86)

The procedure of Example EC16 was followed except that the oil bath was at 140° C. The product was obtained as an opaque solid.

Preparation and Testing of Pharmaceutical Formulations Containing CYSC Polymers, CYC Compounds, CYSC Block Copolymers, and Comparative Compounds.

Release samples containing risperidone or diclofenac sodium were prepared and tested as described above (for the ECC polymers) using the various CYSC polymer, CYC compounds, CYSC block copolymers and other compounds described below. The CYSC polymers used were three poly (alkyl lactide) polymers as described in WO 2007/0142461 (Baker et al.), U.S. Pat. No. 6,469,133, US published application Nos. 20070142461 and 20010044514, the disclosures of which are incorporated by reference herein for all purposes. The polymer referred to herein by the abbreviation "Poly(C8)" is the analog of poly(lactide) with its methyl group replaced by an octyl group which has an Mn of 69,515 and an Mw of 76,960. The polymer referred to herein as "Poly(C16)" is the analog of poly(lactide) with its methyl group replaced by an hexadecyl group; it has an Mn of 150,300, an Mw of 164,950 and a Tp of 43.1° C. The polymer referred to herein as "Poly(C16)LM" is a lower molecular weight version of poly(C16), and has an Mn of 4287, an Mw of 4829 and a Tp of 40.6° C. Table EC3A below shows the composition of other release samples used in the release tests.

TABLE EC3A

| Release sample # | risperidone or diclofenac sodium, as indicated, with |
|---|---|
| 336-131-4 | stearic acid (C21 acid) |
| 336-116-6 | ethoxylated stearyl alcohol (6E0) |
| 336-116-8 | ethoxylated stearyl alcohol (10 E0) |
| 336-116-7 | ethoxylated stearyl alcohol (40 E0) |
| 336-115-1 | lauric acid (C11 acid) |
| 336-115-2 | myristic acid (C13 acid) |
| 336-115-3 | stearic acid (C 70 acid) |
| 341-73-7 | behenic acid (C21 acid) |
| 341-48-1 | non-crystalline PLGA (H)-PLGA-C6-PLGA-OH) |
| 336-130-3 | mixture of PLGA with Ethal CSA-3, C16-18 alcohol with 3 moles ethylene oxide from Ethox Chemical LLC |
| 336-130-10 | mixture of PLGA with ERS S00707, C18-22 alcohol with 5 moles ethylene oxide |
| 336-130-11 | mixture of PLGA with ERS S00708, C18-22 alcohol with 6 moles ethylene oxide |

Figure 9A:
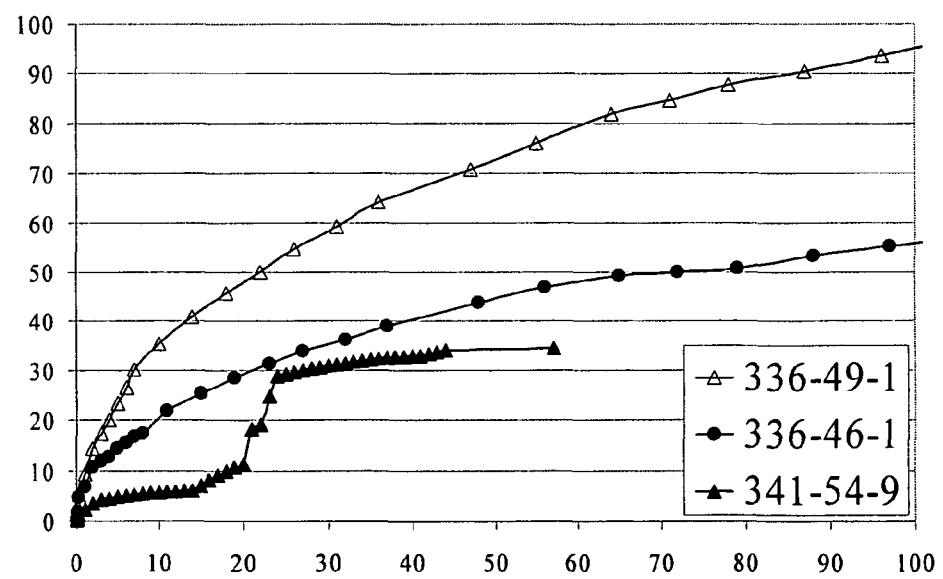
FIG. 9a shows, on the vertical axis, the cumulative release of risperidone from test sample ID #341-54-3 based on PolyC8, from test sample ID #336-46-1 based on PolyC16, and from test sample ID #341-54-9, based on Poly C16LM, and, on the horizontal axis, the time in days.
Figure 9B:
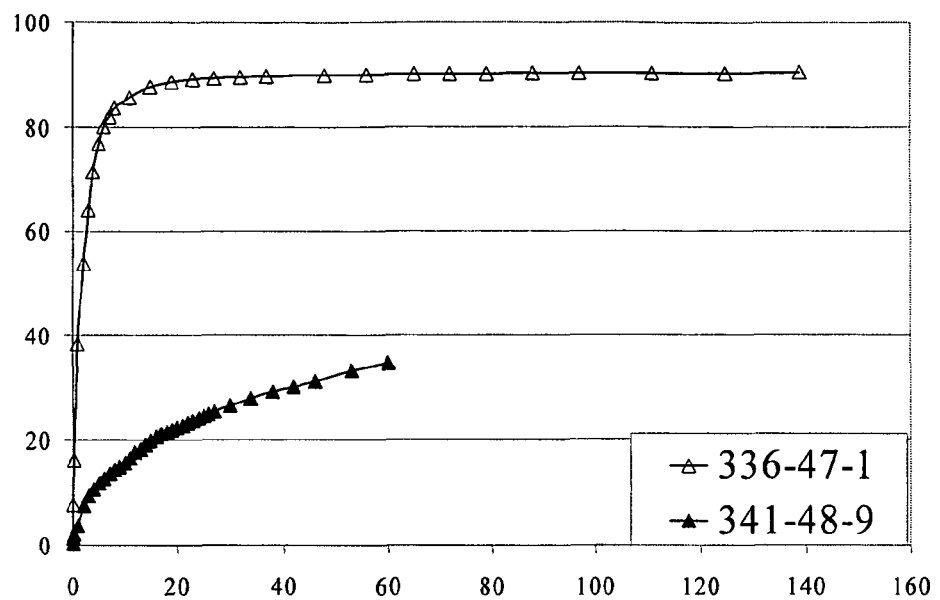
FIG. 9b shows, on the vertical axis, the cumulative release of diclofenac sodium from test sample ID #336-47-1 based on PolyC16 and from test sample ID #341-48-9 based on PolyC16LM, and, on the horizontal axis, the time in days.

The results of the testing are shown in FIGS. 9-15, which (as in FIGS. 1-8) show the cumulative release of
(i) in FIG. 9a, risperidone from test sample ID #341-54-3 based on PolyC8, from test sample ID #336-46-1 based on PolyC16, and from test sample ID #341-54-9, based on Poly C16LM;
(ii) in FIG. 9b, diclofenac sodium from test sample ID #336-47-1 based on PolyC16 and from test sample ID #341-48-9 based on PolyC16LM;
(iii) in FIG. 10a, risperidone from test sample ID #341-73-1 based on CYC compound ID #341-55-1 prepared in Example EC11A, from test sample ID #341-73-2 based on CYC compound ID #341-55-2 prepared in Example EC11B, from test sample ID #341-73-3 based on CYC compound ID #341-55-3 prepared in Example EC11C, from test sample ID #341-73-5 based on CYC compound ID #341-55-6 prepared in Example EC11F, from test sample ID #341-73-6 based on CYC compound ID #341-

Figure 10A:
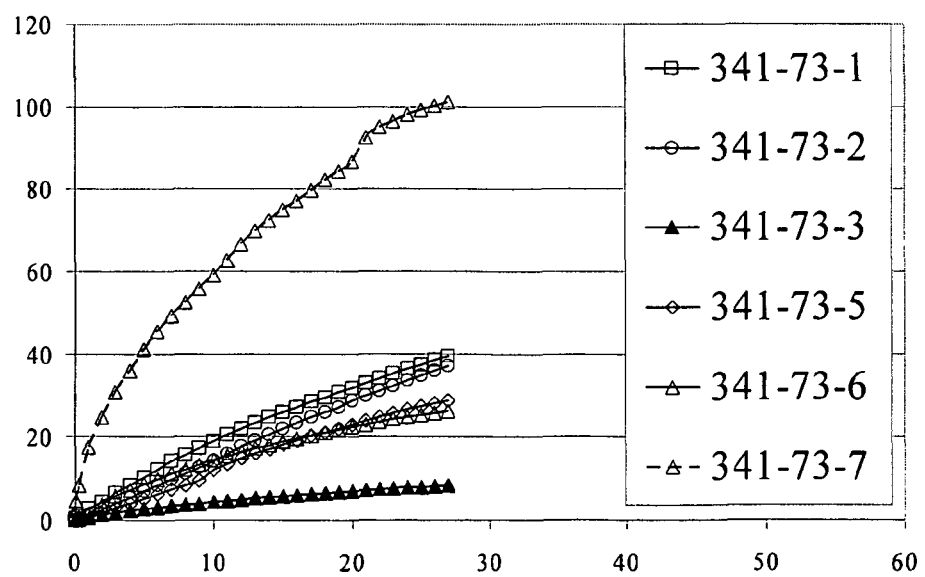
FIG. 10a shows, on the vertical axis, the cumulative release of risperidone from test sample ID #341-73-1 based on CYC compound ID #341-55-1 prepared in Example EC11A, from test sample ID #341-73-2 based on CYC compound ID #341-55-2 prepared in Example EC11B, from test sample ID #341-73-3 based on CYC compound ID #341-55-3 prepared in Example EC11C, from test sample ID #341-73-5 based on CYC compound ID #341-55-6 prepared in Example EC11F, from test sample ID #341-73-6 based on CYC compound ID #341-55-6 prepared in Example EC11E, and from test sample ID #341-73-6 based on behenic acid, and, on the horizontal axis, the time in days.
Figure 10B:
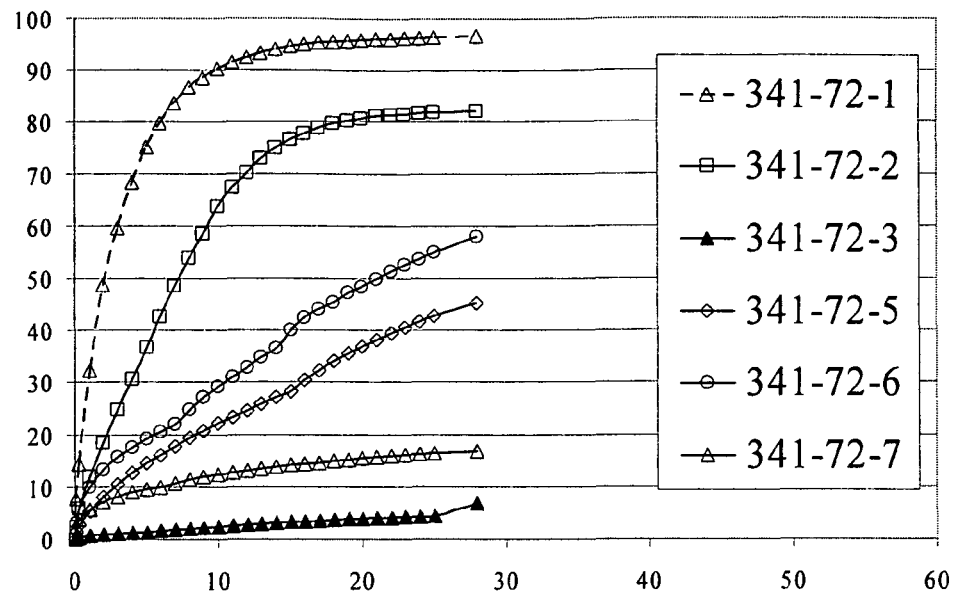
FIG. 10b shows, on the vertical axis, the cumulative release of diclofenac sodium from test sample ID #341-72-1 based on CYC compound ID #341-55-1 prepared in Example EC11A, from test sample ID #341-72-2 based on CYC compound ID #341-55-2 prepared in Example EC11B, from test sample ID #341-72-3 based on CYC compound ID #341-55-3 prepared in Example EC11C, from test sample ID #341-72-5 based on CYC compound ID #341-55-5 prepared in Example EC11E, from test sample ID #341-72-6 based on CYC compound ID #341-55-6 prepared in Example EC11F, and from test sample ID #341-72-7 based on behenic acid, and, on the horizontal axis, the time in days.
Figure 11A:
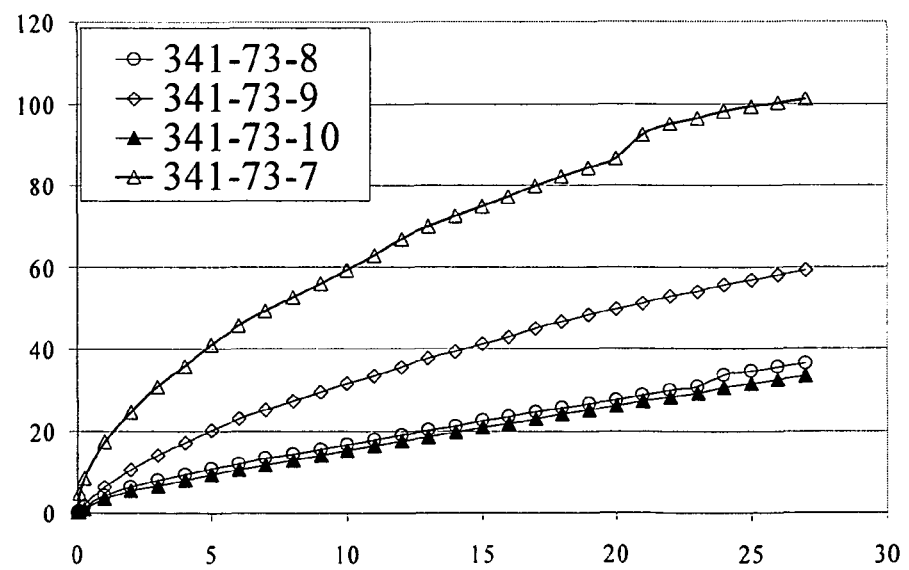
FIG. 11a shows, on the vertical axis, the cumulative release of Risperidone from Test Sample ID Number 341-73-8 based on CYC Compound ID Number 341-62-1 prepared in Example 12A, from Test Sample ID Number 341-73-9 based on CYC Compound ID Number 341-62-2 prepared in Example EC 12B, from Test Sample ID Number 341-73-10 based on CYC Compound ID Number 341-62-3 prepared in Example EC 12C, and from Test Sample ID Number 341-73-7 based on C22 Acid, and, on the horizontal axis, the time in days.
Figure 11B:
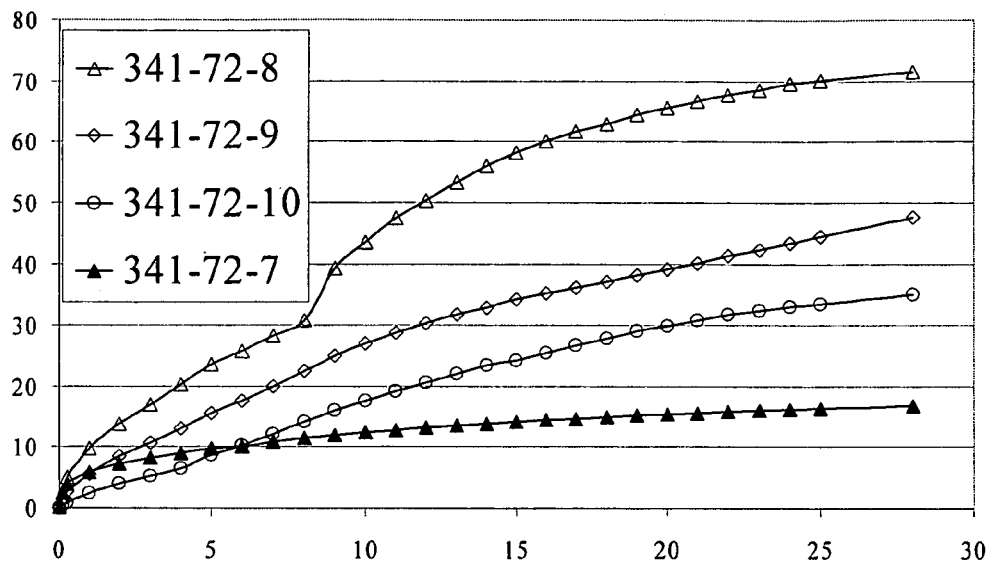
FIG. 11b shows, on the vertical axis, the cumulative release of diclofenac sodium from test sample ID #341-72-8 based on CYC compound ID #341-62-1 prepared in Example 12A, from test sample ID #341-72-9 based on CYC compound ID #341-62-2 prepared in Example EC12B, from test sample ID #341-72-10 based on CYC compound ID #341-62-3 prepared in Example EC12C, and from test sample ID #341-72-7 based on C22 Acid, and, on the horizontal axis, the time in days.
Figure 12:
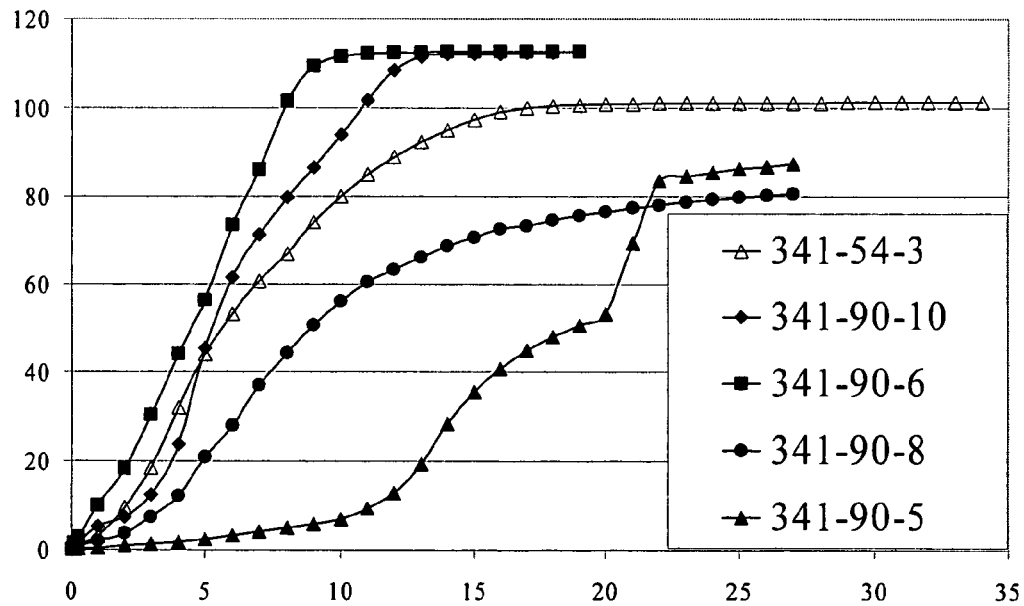
FIG. 12 shows, on the vertical axis, the cumulative release of risperidone from test sample #341-54-3 based on polymer ID #341-1-0 prepared in Example EC1(C), from test sample #341-90-10 based on CYSC block copolymer ID #341-89 prepared in Example EC14, from test sample #341-90-6 based on CYSC block copolymer ID #341-85 prepared in Example EC15, from test sample #341-90-8 based on CYSC block copolymer ID #341-86 prepared in Example EC16, and from test sample #341-90-5 based on CYSC block copolymer ID #341-82 prepared in Example EC15, and, on the horizontal axis, the time in days.
Figure 13:
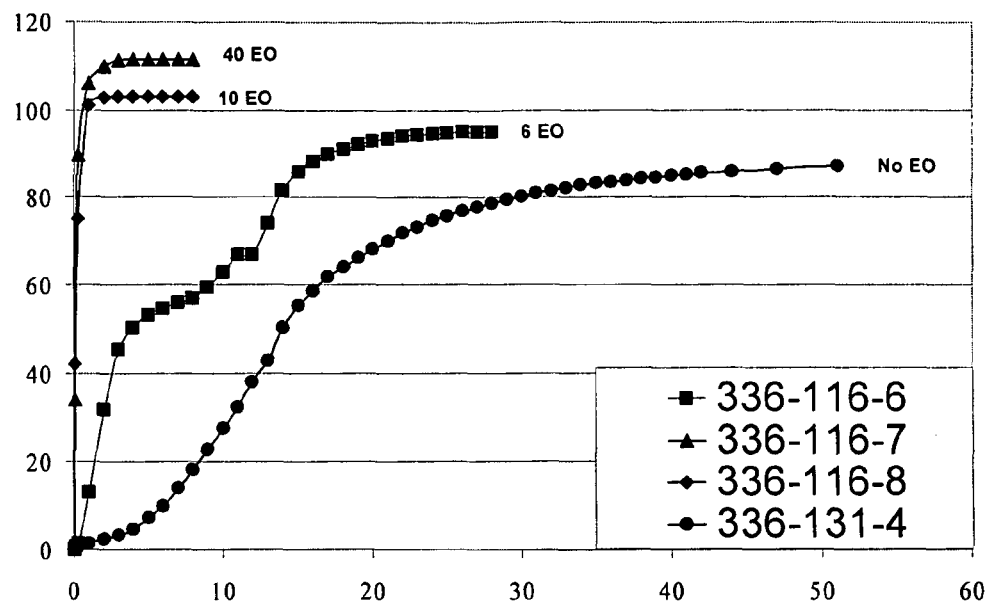
FIG. 13 shows, on the vertical axis, the cumulative release of diclofenac sodium from release samples ID # 336-131-4, 336 116-6, 336-116-7 and 336-116-8, all based on ethoxylated stearyl alcohol, and, on the horizontal axis, the time in days.
Figure 14:
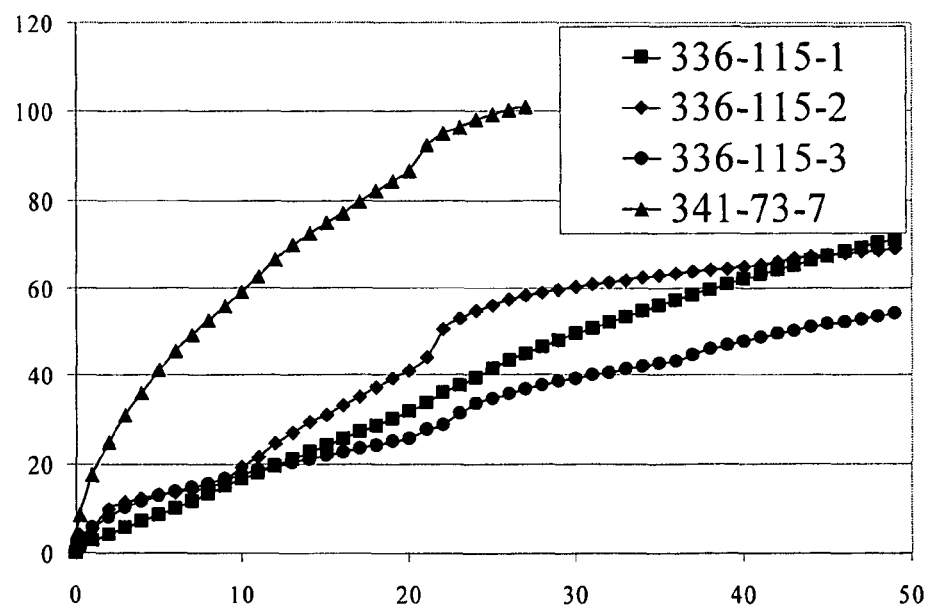
FIG. 14 shows, on the vertical axis, the cumulative release of risperidone from release samples ID number 336-115-1, 336-115-2, 336-115-3 and 341-73-7, all based on fatty acids, and, on the horizontal axis, the time in days
Figure 15:
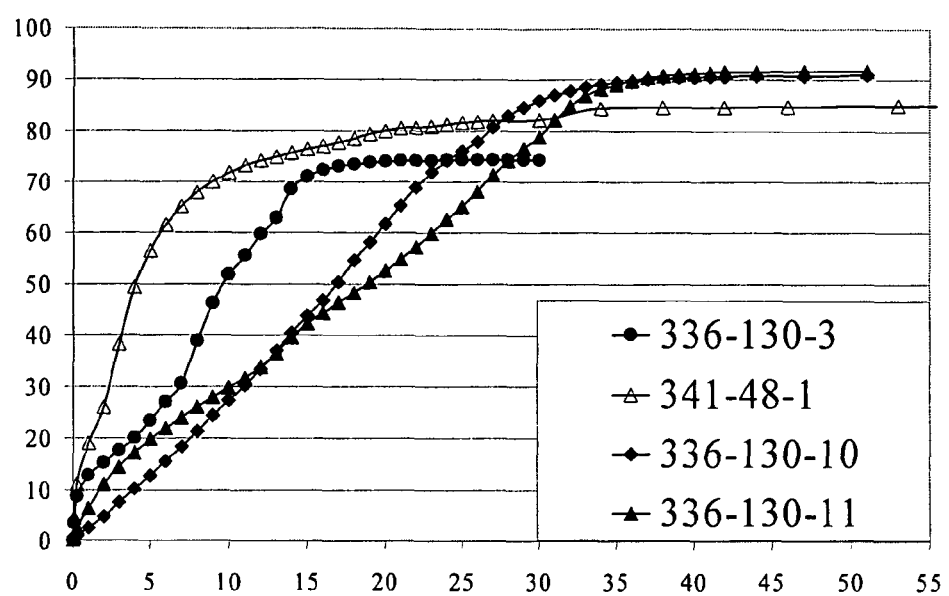
FIG. 15 shows, on the vertical axis, the cumulative release of diclofenac sodium from release samples 341-48-1, 336-130-3, 336-130-10 and 336-130-11, based on commercial PLGA, PLGA plus Ethal CSA-3, PLGA plus ERS S00707, and PLGA plus ERS X00708, respectively, and, on the horizontal axis, the time in days

55-6 prepared in Example EC11E, and from test sample ID #341-73-6 based on behenic acid;

(iv) in FIG. 10*b*, diclofenac sodium from test sample ID #341-72-1 based on CYC compound ID #341-55-1 prepared in Example EC11A, from test sample ID #341-72-2 based on CYC compound ID #341-55-2 prepared in Example EC11B, from test sample ID #341-72-3 based on CYC compound ID #341-55-3 prepared in Example EC11C, from test sample ID #341-72-5 based on CYC compound ID #341-55-5 prepared in Example EC11E, from test sample ID #341-72-6 based on CYC compound ID #341-55-6 prepared in Example EC11F, and from test sample ID #341-72-7 based on behenic acid;

(v) in FIG. 11*a*, risperidone from test sample ID #341-73-8 based on CYC compound ID #341-62-1 prepared in Example 12A, from test sample ID #341-73-9 based on CYC compound ID #341-62-2 prepared in Example EC12B, from test sample ID #341-73-10 based on CYC compound ID #341-62-3 prepared in Example EC12C, and from test sample ID #341-73-7 based on C22 Acid;

(vi) in FIG. 11*b*, diclofenac sodium from test sample ID #341-72-8 based on CYC compound ID #341-62-1 prepared in Example 12A, from test sample ID #341-72-9 based on CYC compound ID #341-62-2 prepared in Example EC12B, from test sample ID #341-72-10 based on CYC compound ID #341-62-3 prepared in Example EC12C, and from test sample ID #341-72-7 based on C22 Acid;

(vi) in FIG. 12, risperidone from test sample #341-54-3 based on polymer ID #341-1-0 prepared in Example EC1(C), from test sample #341-90-10 based on CYSC block copolymer ID #341-89 prepared in Example EC14, from test sample #341-90-6 based on CYSC block copolymer ID #341-85 prepared in Example EC15, from test sample #341-90-8 based on CYSC block copolymer ID #341-86 prepared in Example EC16, and from test sample #341-90-5 based on CYSC block copolymer ID #341-82 prepared in Example EC15;

(vii) in FIG. 13, diclofenac sodium from release samples ID #336-131-4, 336 116-6, 336-116-7 and 336-116-8, all based on ethoxylated stearyl alcohol;

(vii) in FIG. 14, risperidone from release samples ID number 336-115-1, 336-115-2, 336-115-3 and 341-73-7, all based on fatty acids; and (viii) in FIG. 15, diclofenac sodium from release samples 341-48-1, 336-130-3, 336-130-10 and 336-130-11, based on commercial PLGA, PLGA plus Ethal CSA-3, PLGA plus ERS S00707, and PLGA plus ERS X00708, respectively.

Examples EC18-EC 20

Examples EC 18-EC 20 illustrate the preparation of CYC self-assemblies.

Examples 18-1 to 18-36 are summarized in Table EC4 below, which shows the starting materials and the weight in grams of CYSC polymer, the combined weight of the CYSC polymer and the additive being 1 g.

TABLE EC 4

| Ex # | Sample ID# 020408-ID # | CYSC polymer ID # | wt (g) | Additive to 1 g name | Tp |
|---|---|---|---|---|---|
| 18-1 | 13 | 328-133-1 | 0.78 | C18OH | 50.49 |
| 18-2 | 7 | 328-133-1 | 0.55 | C18OH | 52.09 |
| 18-3 | 1 | 328-133-1 | 0.29 | C18OH | 47.18 |
| 18-4 | 14 | 326-1-1 | 0.79 | C18OH | 51.45 |
| 18-5 | 8 | 326-1-1 | 0.56 | C18OH | 51.14 |
| 18-6 | 2 | 326-1-1 | 0.30 | C18OH | 56.26 |
| 18-7 | 15 | 326-3-1 | 0.83 | C18OH | 46.55 |
| 18-8 | 9 | 326-3-1 | 0.61 | C18OH | 48.57 |
| 18-9 | 3 | 326-3-1 | 0.35 | C18OH | 46.63 & 56.84 |
| 18-10 | 16 | 327-42-11 | 0.84 | C18OH | 40.67 & 49.46 |
| 18-11 | 10 | 327-42-11 | 0.64 | C18OH | 51.40 |
| 18-12 | 4 | 327-42-11 | 0.37 | C18OH | 55.90 |
| 18-13 | 17 | 326-1-2 | 0.74 | C18OH | −0.80 & 48.87 |
| 18-14 | 11 | 326-1-2 | 0.49 | C18OH | −1.53 & 56.08 |
| 18-15 | 5 | 326-1-2 | 0.24 | C18OH | −2.63 & 58.53 |
| 18-16 | 18 | 336-141-3 | 0.98 | C18OH | 41.99 |
| 18-17 | 12 | 336-141-3 | 0.93 | C18OH | 45.17 |
| 18-18 | 6 | 336-141-3 | 0.82 | C18OH | 45.10 & 50.52 |
| 18-19 | 31 | 328-133-1 | 0.65 | POE (6) C18OH | 47.61 |
| 18-20 | 25 | 328-133-1 | 0.39 | POE (6) C18OH | 42.84 |
| 18-21 | 19 | 328-133-1 | 0.17 | POE (6) C18OH | 41.94 |
| 18-22 | 32 | 326-1-1 | 0.67 | POE (6) C18OH | 47.34 |
| 18-23 | 26 | 326-1-1 | 0.40 | POE (6) C18OH | 46.23 |
| 18-24 | 20 | 326-1-1 | 0.18 | POE (6) C18OH | 42.49 |
| 18-25 | 33 | 326-3-1 | 0.72 | POE (6) C18OH | 43.12 |
| 18-26 | 27 | 326-3-1 | 0.46 | POE (6) C18OH | 49.95 |
| 18-27 | 21 | 326-3-1 | 0.22 | POE (6) C18OH | 42.35 |
| 18-28 | 34 | 327-42-11 | 0.74 | POE (6) C18OH | 44.14 |
| 18-29 | 28 | 327-42-11 | 0.48 | POE (6) C18OH | 44.84 |
| 18-30 | 22 | 327-42-11 | 0.24 | POE (6) C18OH | 42.09 |
| 18-31 | 35 | 326-1-2 | 0.60 | POE (6) C18OH | −2.48 & 33.07 |
| 18-32 | 23 | 326-1-2 | 0.14 | POE (6) C18OH | −1.88 & 38.91 |
| 18-33 | 29 | 326-1-2 | 0.33 | POE (6) C18OH | −4.98 & 41.87 |
| 18-34 | 36 | 336-141-3 | 0.95 | POE (6) C18OH | 40.63 |
| 18-35 | 24 | 336-141-3 | 0.70 | POE (6) C18OH | 42.23 |
| 18-36 | 30 | 336-141-3 | 0.88 | POE (6) C18OH | 44.57 |
| 18-37 | — | — | | C18OH | 58.75 ΔH 206.1 |
| 18-38 | | 326-1-1 | 1.00 | — | 47.55 ΔH 77.73 |
| 18-39 | | 326-1-1 | 0.792 | C18OH | 49.26 ΔH 92.66 |
| 18-40 | | 326-1-1 | 0.559 | C18OH | 53.25 ΔH 98.64 |

In Table EC 4, POE (6)C18OH is stearyl alcohol which has been ethoxylated with 6 mol of ethylene oxide; and the CYSC polymers are identified in Table EC4A below, which gives the Tps of the polymers and the molar amounts of the monomers from which the polymers are derived.

TABLE EC4A

| CYSC polymer ID # | 328-133-1 | 326-1-1 | 326-3-1 | 327-42-11 | 326-1-2 | 336-141-3 |
|---|---|---|---|---|---|---|
| C18A | 1 | 4 | 4 | 4 | | |
| AA | | 1 | 1 | 1 | | |
| PEG6 A | | | 1 | | | |
| PEG6 MA | | | | 1 | | |
| HEMA | | | | | 1 | |
| Acrylamide | | | | | 1 | |
| C12A | | | | | | 4 |

TABLE EC4A-continued

| CYSC polymer ID # | 328-133-1 | 326-1-1 | 326-3-1 | 327-42-11 | 326-1-2 | 336-141-3 |
|---|---|---|---|---|---|---|
| HEA |  |  |  |  | 1 |  |
| GA |  |  |  |  |  | 20 |
| LA |  |  |  |  |  | 20 |
| C22OH |  |  |  |  |  | 1 |
| Tp | 47.77 | 48.21 | 43.67 | 45.18 | −1.70 | 40.47 |

The samples set out in Table EC4 were prepared in the following way. A total of 1 g of the CYSC polymer and the additive (in the different amounts given in the table) were dissolved in 5 mL of THF. The THF was evaporated in a fume hood at room temperature, and the final dry mixtures were obtained by removing residual THF under reduced pressure at 50° C. overnight.

Examples EC19-1 to EC 19-9 illustrate the preparation of CYC self-assemblies using two CYSC polymers and are summarized in Table EC5 below, which shows the starting materials and the percentage amounts of the CYSC polymers by weight.

TABLE EC5

| Example # | Sample ID # 042108- | CYSC polymer A ID # | wt % | CYSC polymer B to 100% ID # |
|---|---|---|---|---|
| 19-1 | 1 | 326-1-1 | 3.06 | 336-141-3 |
| 19-2 | 4 | 326-1-1 | 8.64 | 336-141-3 |
| 19-3 | 7 | 326-1-1 | 22.11 | 336-141-3 |
| 19-4 | 2 | 327-42-11 | 4.21 | 336-141-3 |
| 19-5 | 5 | 327-42-11 | 11.65 | 336-141-3 |
| 19-6 | 8 | 327-42-11 | 28.35 | 336-141-3 |
| 19-7 | 3 | 327-42-11 | 19.30 | 326-1-1 |
| 19-8 | 6 | 327-42-11 | 41.77 | 326-1-1 |
| 19-9 | 9 | 327-42-11 | 68.27 | 326-1-1 |

The CYSC polymers in Table EC 5 are identified above.

The Samples in Examples 19-1 to 19-9 were prepared in the following way. A total of 1 g of the two CYSC polymers (in the different amounts given in the table) were dissolved in 5 mL of THF. The THF was evaporated in a fume hood at room temperature, and the final dry mixtures were obtained by removing residual THF under reduced pressure at 50° C. overnight.

Figure 16:
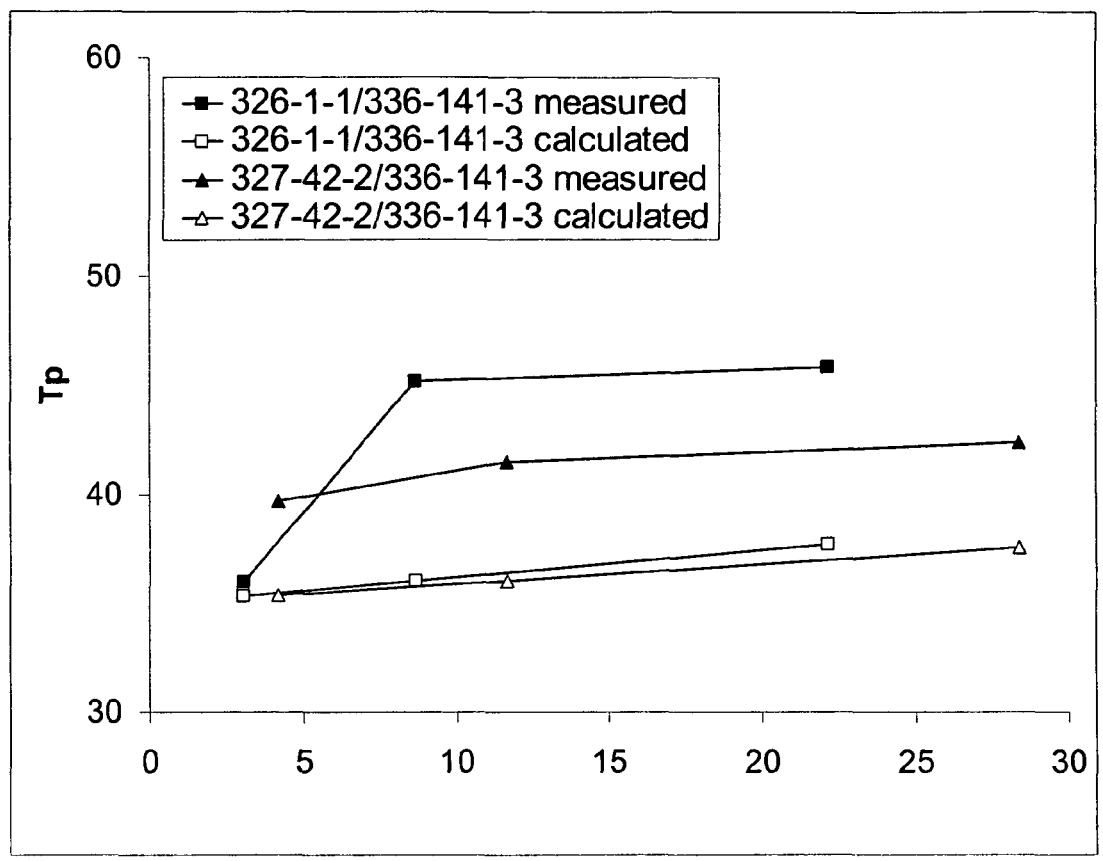
FIGS. 16 and 17 shows the measured and theoretical values of Tp and ΔH respectively for various mixtures of polymer ID #336-141-3 with one of polymer ID #326-1-1 and polymer ID #327-42-11, the theoretical values being calculated as a weighted sum of contributions from the two components.
Figure 17:
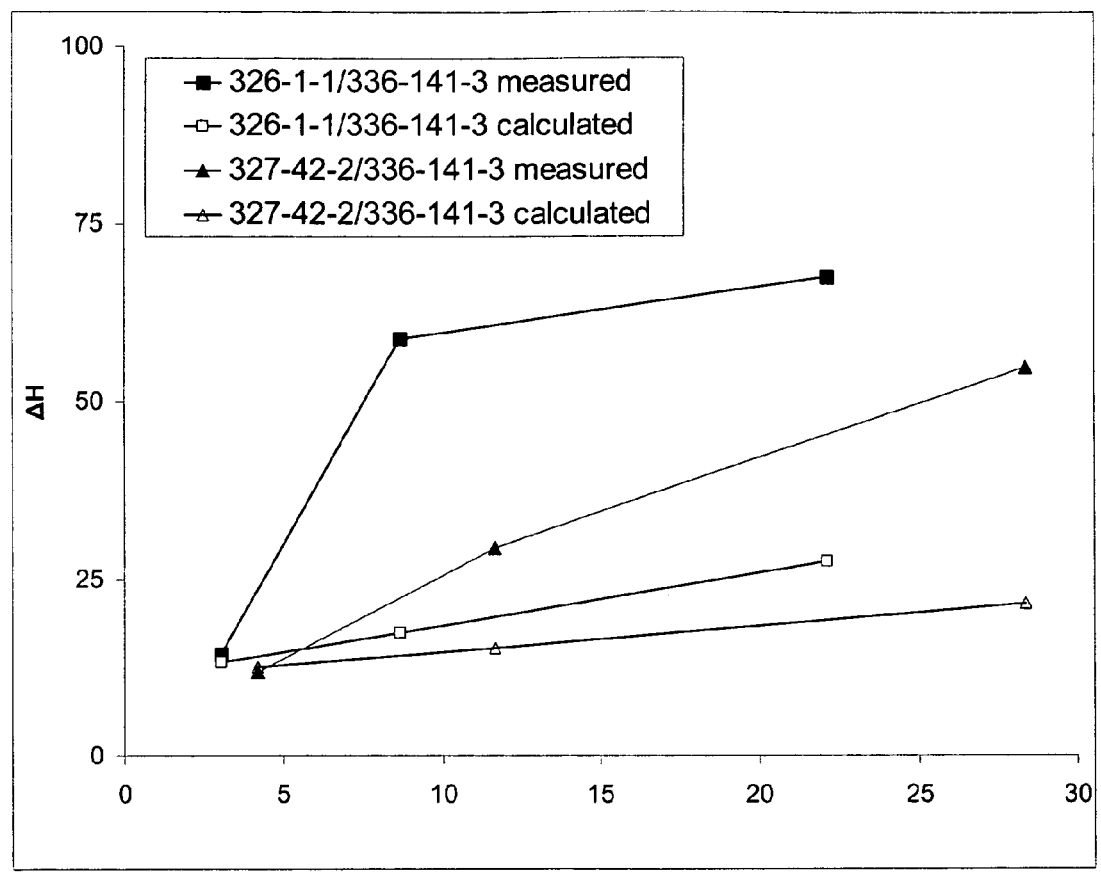

FIGS. 16 and 17 shows the measured and theoretical values of Tp and ΔH respectively for various mixtures of polymer ID #336-141-3 with one of polymer ID #326-1-1 and polymer ID #327-42-11, the theoretical values being calculated as a weighted sum of contributions from the two components. In FIG. 16, Tp is shown on the vertical axis. In FIG. 17, ΔH is shown on the vertical axis. In both Figures, the weight % of one of the polymers (ID #326-1-1 of 3 to 7-42-11) is shown on the horizontal axis. Each of the mixtures has a single Tp indicating co-crystallization through self-assembly; and the ΔH of the mixtures is higher than the theoretical value.

Examples EC20-1 to EC 20-18 illustrate the preparation of pharmaceutical formulations comprising drugs and CYC self-assemblies using two CYSC polymers. They are summarized in Table EC6 below, which shows the starting materials and the amounts thereof in grams.

TABLE EC6

| Ex # | Drug (g) | Polymer mixture (g) | CYSC polymer A ID # | % of polymer | CYSC polymer B to 100% ID # |
|---|---|---|---|---|---|
| 20-1 | Risp (0.0475) | 0.5227 | 336-141-3 | 100 | — |
| 20-2 | Risp (0.0471) | 0.5186 | 326-1-1 | 3.1 | 336-141-3 |
| 20-3 | Risp (0.0469) | 0.5165 | 326-1-1 | 8.6 | 336-141-3 |
| 20-4 | Risp (0.0478) | 0.5248 | 326-1-1 | 22.1 | 336-141-3 |
| 20-5 | Dcl (0.0477) | 0.5253 | 336-141-3 | 100 | 336-141-3 |
| 20-6 | Dcl (0.0466) | 0.5124 | 326-1-1 | 3.1 | 336-141-3 |
| 20-7 | Dcl (0.0468) | 0.5156 | 326-1-1 | 8.6 | 336-141-3 |
| 20-8 | Dcl (0.0465) | 0.5117 | 326-1-1 | 22.1 | 336-141-3 |
| 20-9 | Risp (0.0469) | 0.5158 | 327-42-11 | 4.2 | 336-141-3 |
| 20-10 | Risp (0.0460) | 0.5059 | 327-42-11 | 28.4 | 336-141-3 |
| 20-11 | Risp (0.0475) | 0.5231 | 327-42-11 | 100 | — |
| 20-12 | Dcl (0.0460) | 0.5071 | 327-42-11 | 4.2 | 336-141-3 |
| 20-13 | Dcl (0.0472) | 0.5189 | 327-42-11 | 28.4 | 336-141-3 |
| 20-14 | Dcl (0.0470) | 0.5177 | 327-42-11 | 100 | — |
| 20-15 | Risp (0.0429) | 0.52 | 326-1-1 | 19.3 | 327-42-11 |
| 20-16 | Risp (0.0484) | 0.5323 | 326-1-1 | 41.8 | 327-42-11 |
| 20-17 | Dcl (0.0472) | 0.5184 | 326-1-1 | 19.3 | 327-42-11 |
| 20-18 | Dcl (0.0469) | 0.5168 | 326-1-1 | 41.8 | 327-42-11 |

The Samples in Examples 20-1 to 20-18 were prepared by a hot-melt extrusion technique. The components of the mixture were first micronized using conventional milling techniques. They are then blended thoroughly and the blend is extruded through a hot-melt extruder at a temperature in the range 30-° C.

Examples EC 21-1 to EC 21-14 illustrate pharmaceutical formulations comprising risperidone and a CYC assembly. Table EC 7 shows the starting materials and the percentage amounts by weight of the components of the CYC assembly. The formulations were prepared in the following way. A total of 1 g of 2-ECC-PLGA (ID #338-143 and either crystallizable small molecule additives or 1-ECC PLGA (ID #336-141-3) (in the different amounts given in Table EC 7) were dissolved in 5 mL of THF. The THF was evaporated in a fume hood at room temperature, and the final dry mixtures were obtained by removing residual THF under reduced pressure at 50° C. overnight.

TABLE EC6

| Ex # | Sample ID #042108- | 2-ECC-PLGA ID #338-143 wt % | additive to 100% ID # |
|---|---|---|---|
| 21-1 | 1 | 6.35 | 336-141-3 |
| 21-2 | 2 | 69.30 | C22OH |
| 21-3 | 3 | 57.94 | Stearyl POE-6 |
| 21-4 | 4 | 16.91 | 336-141-3 |
| 21-5 | 5 | 73.15 | C18OH |
| 21-6 | 6 | 87.13 | C22OH |
| 21-7 | 7 | 80.52 | Stearyl POE-6 |
| 21-8 | 8 | 37.91 | 336-141-3 |
| 21-9 | 9 | 89.10 | C18OH |
| 21-10 | 10 | 0 | 336-141-3 |
| 21-11 | 11 | 0 | C22OH |
| 21-12 | 12 | 0 | C18OH |
| 21-13 | 13 | 0 | Stearyl POE-6 |
| 21-14 | 40 | 0 | — |

Preparation and Testing of Pharmaceutical Formulations Containing CYSC Polymers, CYC Compounds, CYSC Block Copolymers, and Comparative Compounds.

Release samples containing risperidone or diclofenac sodium were prepared and tested as described above (for the ECC polymers) using the various CYC self-assemblies described below.

Figure 18:
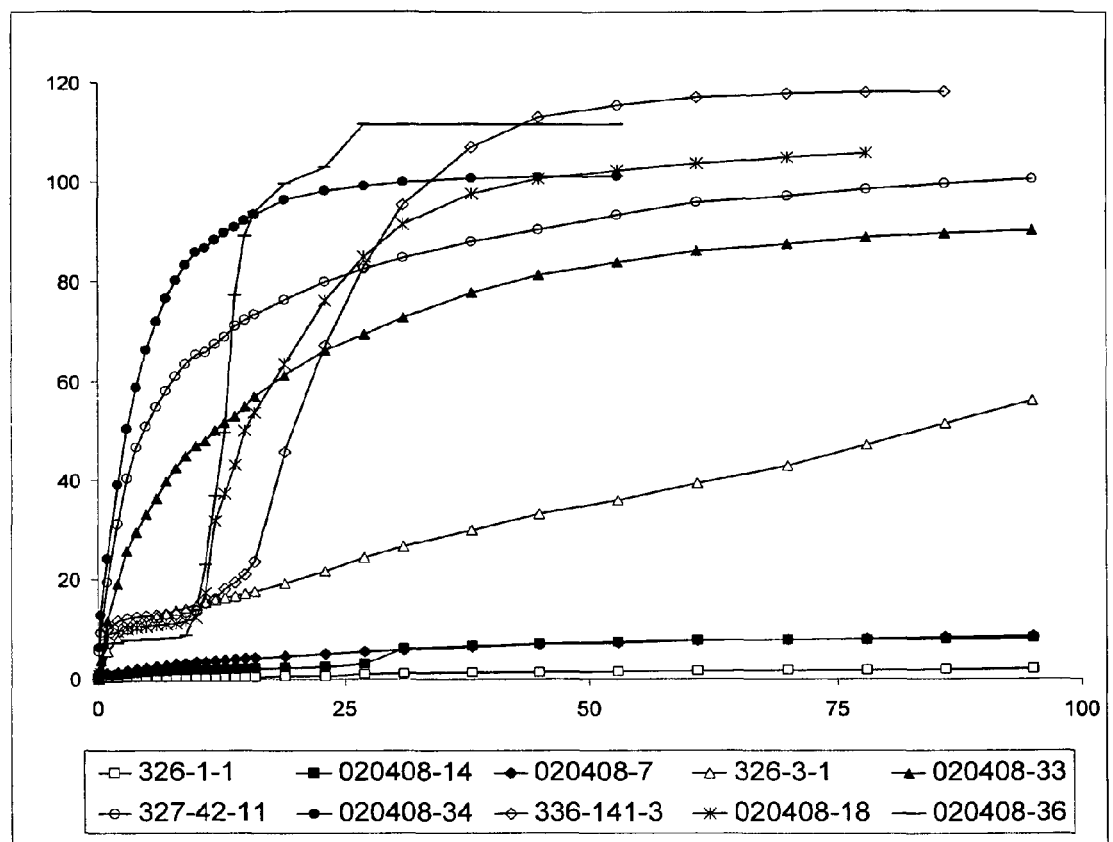
FIG. 18 shows, on the vertical axis, the cumulative release of risperidone from a test sample based on polymer ID #326-1-1, from a test sample based on polymer ID #326-3-1, from a test sample based on mixture of polymer ID #327-42-11 with 26.4% by weight POE(6)C18OH, from a test sample based on a mixture of polymer ID #336-141-3 with 4.5% POE(6)C18OH, from a test sample based on a mixture of polymer ID #326-1-1 with 20.8% C18OH, from a test sample based on mixture of polymer ID #326-3-1 with 28.4% POE (6)C18OH , from a test sample based on polymer ID #336-141-3, from a test sample based on a mixture of polymer ID #326-1-1 with 44.1% C18OH, from a test sample based on polymer ID #327-42-11, and from a test sample based on a mixture of polymer ID #336-141-3 with 2.43% C18OH, and, on the horizontal axis, the time in days.
Figure 19:
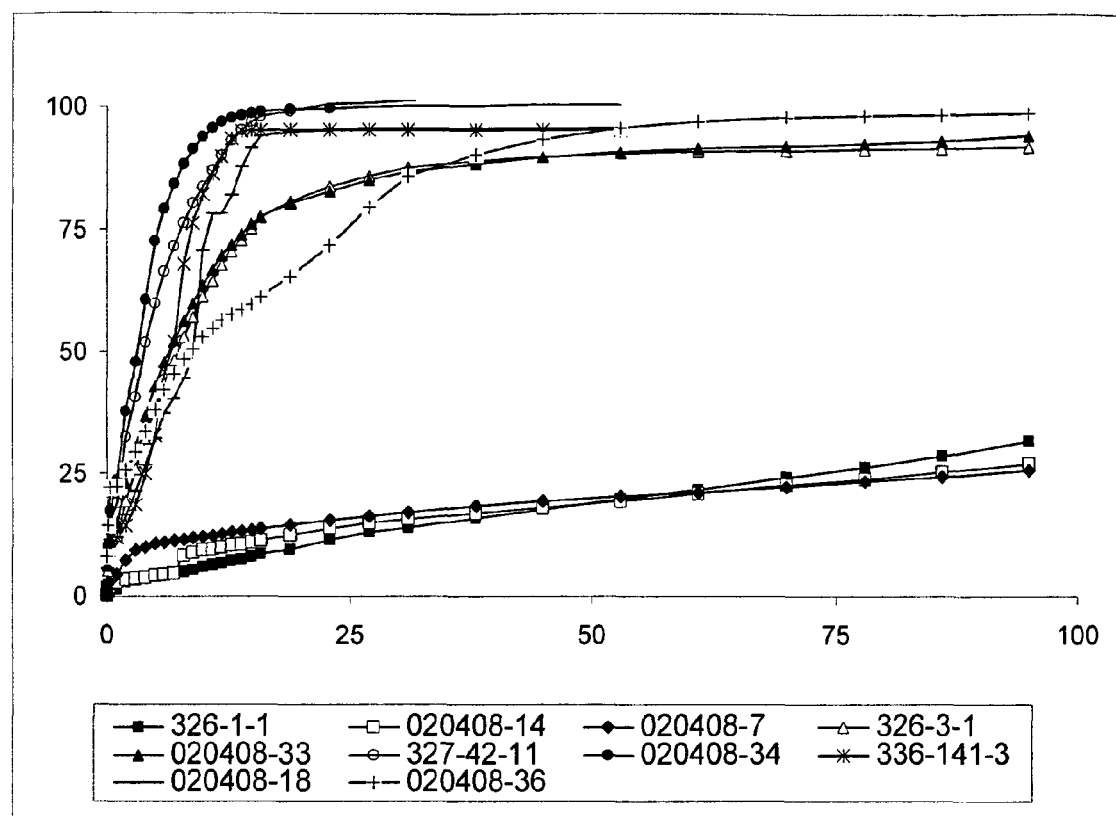
FIG. 19 shows, on the vertical axis, the cumulative release of diclofenac sodium from a test sample based on polymer ID #326-1-1, from a test sample based on a mixture of polymer ID #326-1-1 with 44.1% C18OH, from a test sample based on a mixture of polymer ID #326-3-1 with 28.4% POE(6) C18OH, from a test sample based on a mixture of polymer ID #327-42-11 with 26.4% POE(6)C18OH, from a test sample based on a mixture of polymer ID #336-141-3 with 2.4% C18OH, from a test sample based on a mixture of polymer ID #326-1-1 and 20.1% C18OH, from a test sample based on polymer ID #326-3-1, from a test sample based on polymer ID #327-42-11, from a test sample based on polymer ID #336-141-3, and from a test sample based on a mixture of polymer ID #336-141-3 with 4.5% POE(6)C18OH, and, on the horizontal axis, the time in days.
Figure 20:
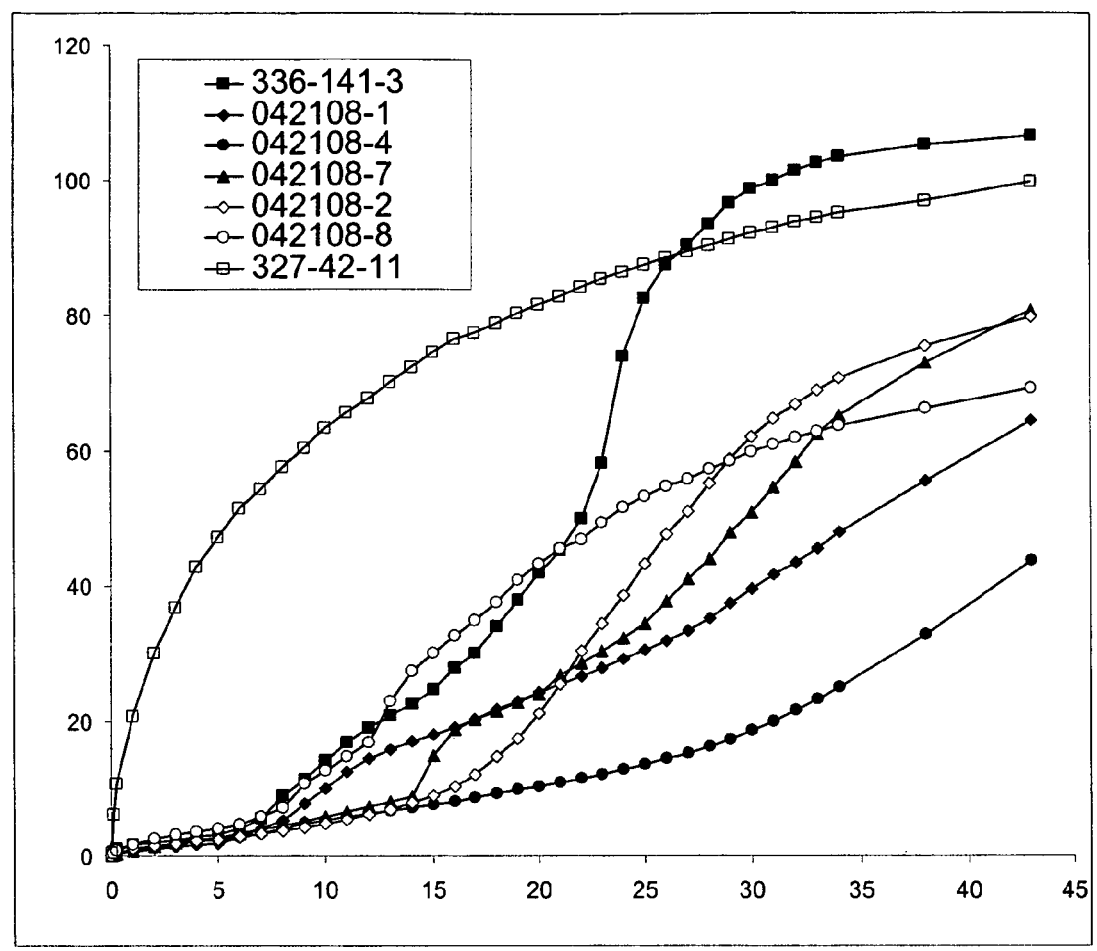
FIG. 20 shows, on the vertical axis, the cumulative release of risperidone from a test sample based on polymer ID #336-141-3, from a test sample based on a mixture of polymer ID #336-141-3 with 3.06% polymer ID #326-1-1, from a test sample based on a mixture of polymer ID #336-141-3 with 8.64% polymer ID #326-1-1, from a test sample based on a mixture of polymer ID #336-141-3 with 4.21% polymer ID #327-42-11, from a test sample based on a mixture of polymer ID #336-141-3 with 28.35% polymer ID #327-42-11, from a test sample based on polymer ID #327-42-11, and from a test sample based on polymer ID #341-1-0, and, on the horizontal axis, the time in days.
Figure 21:
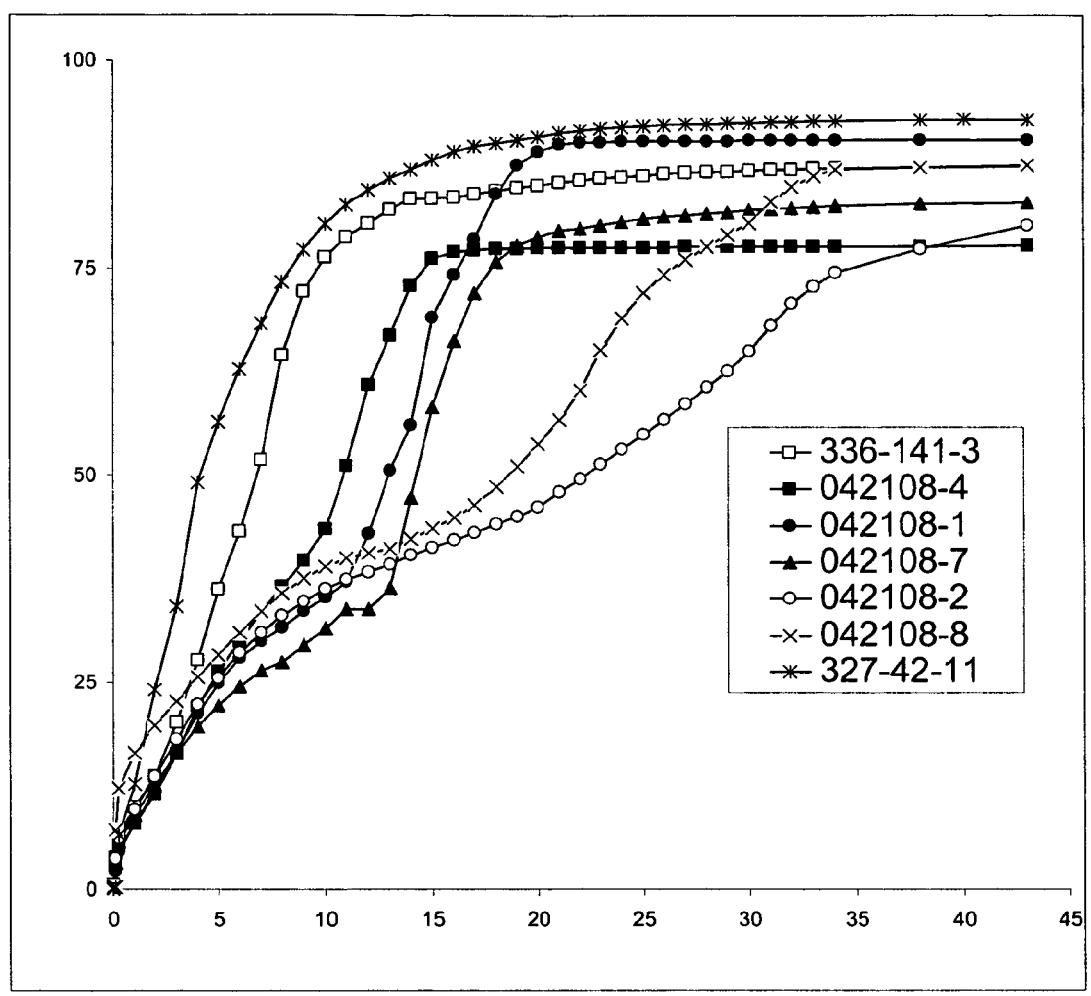
FIG. 21 shows, on the vertical axis, the cumulative release of diclofenac sodium from a test sample based on polymer ID #336-141-3, from a test sample based on the mixture of polymer ID #326-1-1 with 96.9% of polymer ID #336-141-3, from a test sample based on a mixture of polymer ID #326-1 with 91.4% polymer ID #336-141-3, a release sample based on a mixture of polymer ID #326-1-1 with 77.9% polymer ID #336-141-3, from a test sample based on a mixture of polymer ID #327-42-11 with 95.8% polymer ID #336-141-3, from a test sample based on the mixture of polymer ID #327-42-11 with 71.6% polymer ID #336-141-3, and from a test sample based on polymer ID #327-42-11, and, on the horizontal axis, the time in days.
Figure 22:
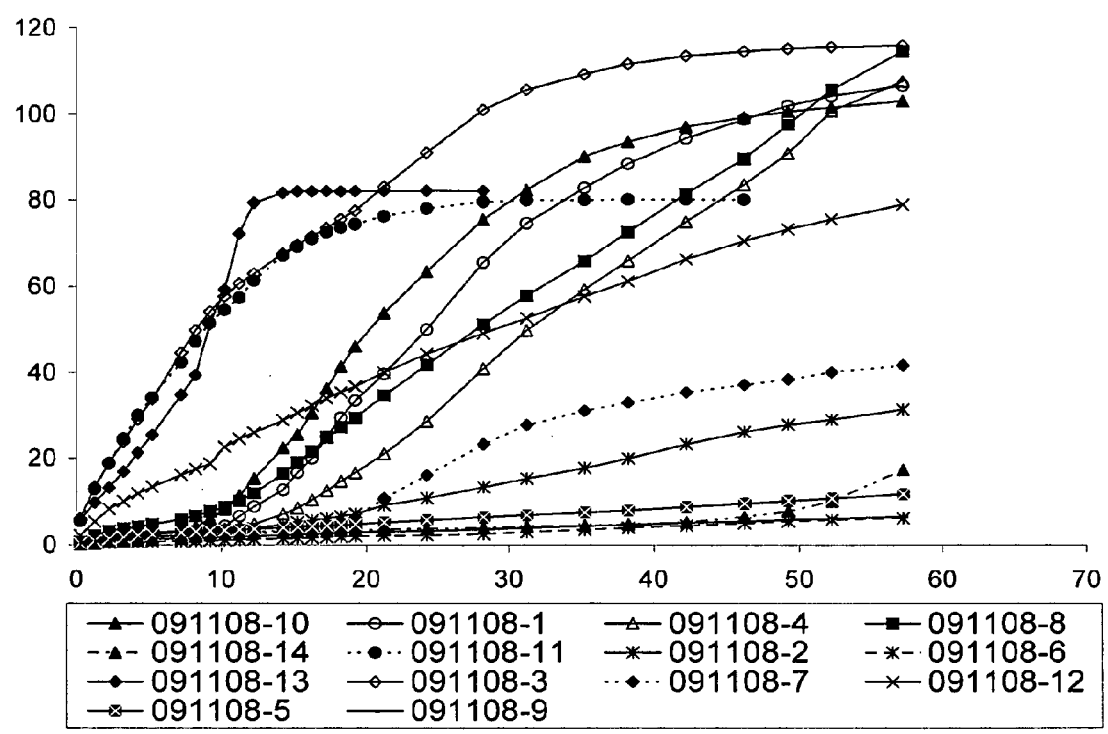
FIG. 22 shows, on the vertical axis, the cumulative release of risperidone from the CYC Self Assemblies Identified in Table EC7.

The results of the testing are shown in FIGS. 18-22, which, as in FIGS. 1-8, show the cumulative release of (i) in FIG. 18, risperidone from a test sample based on polymer ID #326-1-1, from a test sample based on polymer ID #326-3-1, from a test sample based on mixture of polymer ID #327-42-11 with 26.4% by weight POE(6)C18OH, from a test sample based on a mixture of polymer ID #336-141-3 with 4.5% POE(6)C18OH, from a test sample based on a mixture of polymer ID #326-1-1 with 20.8% C18OH, from a test sample based on mixture of polymer ID #326-3-1 with 28.4% POE(6)C18OH, from a test sample based on polymer ID #336-141-3, from a test sample based on a mixture of polymer ID #326-1-1 with 44.1% C18OH, from a test sample based on polymer ID #327-42-11, and from a test sample based on a mixture of polymer ID #336-141-3 with 2.43% C18OH seven:

(ii) in FIG. 19, diclofenac sodium from a test sample based on polymer ID #326-1-1, from a test sample based on a mixture of polymer ID #326-1-1 with 44.1% C18OH, from a test sample based on a mixture of polymer ID #326-3-1 with 28.4% POE(6)C18OH, from a test sample based on a mixture of polymer ID #327-42-11 with 26.4% POE(6) C18OH, from a test sample based on a mixture of polymer ID #336-141-3 with 2.4% C18OH, from a test sample based on a mixture of polymer ID #326-1-1 and 20.1% C18OH, from a test sample based on polymer ID #326-3-1, from a test sample based on polymer ID #327-42-11, from a test sample based on polymer ID #336-141-3, and from a test sample based on a mixture of polymer ID #336-141-3 with 4.5% POE(6)C18OH;

(iii) in FIG. 20, risperidone from a test sample based on polymer ID #336-141-3, from a test sample based on a mixture of polymer ID #336-141-3 with 3.06% polymer ID #326-1-1, from a test sample based on a mixture of polymer ID #336-141-3 with 8.64% polymer ID #326-1-1, from a test sample based on a mixture of polymer ID #336-141-3 with 4.21% polymer ID #327-42-11, from a test sample based on a mixture of polymer ID #336-141-3 with 28.35% polymer ID #327-42-11, from a test sample based on polymer ID #327-42-11, and from a test sample based on polymer ID #341-1-0;

(iv) in FIG. 21, diclofenac sodium from a test sample based on polymer ID #336-141-3, from a test sample based on the mixture of polymer ID #326-1-1 with 96.9% of polymer ID #336-141-3, from a test sample based on a mixture of polymer ID #326-1 with 91.4% polymer ID #336-141-3, a release sample based on a mixture of polymer ID #326-1-1 with 77.9% polymer ID #336-141-3, from a test sample based on a mixture of polymer ID #327-42-11 with 95.8% polymer ID #336-141-3, from a test sample based on the mixture of polymer ID #327-42-11 with 71.6% polymer ID #336-141-3, and from a test sample based on polymer ID #327-42-11; and (v) in FIG. 22, risperidone from the CYC self assemblies identified in Table EC 7.

SSP Examples.

The following Examples illustrate the SSP polymers of the invention.

1. Preparation of SSP Polymers

Table SSP 1 below summarizes the preparation of SSP polymers by solution polymerization of the acrylic monomers and amounts thereof identified in the table. The polymerization was carried out in IPA at 80° C. for 3 hours under nitrogen with 0.1% AIBN. In some cases, BMP (6%) was used to control the molecular weight below 5000 Daltons. IPA was removed under reduced pressure at elevated temperature. At the end of the reduced pressure stage, the internal temperature reached 120-130° C. In general, 0.5 g of Trigonox was added to lower the residual monomer. The reaction was continued at 120-130° C. for at least 1 hr, followed by 1 hr under reduced pressure. However, if the viscosity was too high to stir during or after IPA removal then samples were taken "as is" and put under reduced pressure at 90° C. overnight to remove the IPA.

TABLE SSP 1

| ID | C18A wt % | C22A wt % | AA wt % | C18A/C22A/AA molar ratio | Thermal transition temperature (° C.) 1st heating | 2nd heating | 1st cooling | Average (Mw) | Average (Mn) |
|---|---|---|---|---|---|---|---|---|---|
| Low Mw set with 6% BMP in IPA as solvent | | | | | | | | | |
| 328-57-1 | 60 | 40 | | 1/0/3 | 46.0 | 40.5 | 20.0 | 4504 | 2983 |
| 328-57-2 | 52.9 | 47.1 | | 1/0/4 | 41.8 | 25.3 | 13.4 | 3530 | 2658 |
| 328-57-3 | 47.4 | 52.6 | | 1/0/5 | 42.5 | 41.0 | 12.4 | 3209 | 2445 |

TABLE SSP 1-continued

| ID | C18A | C22A | AA | C18A/C22A/AA molar ratio | Thermal transition temperature (° C.) 1st heating | 2nd heating | 1st cooling | Average (Mw) | Average (Mn) |
|---|---|---|---|---|---|---|---|---|---|
| | wt % | | | | | | | | |
| 328-57-4 | | 63.8 | 36.2 | 0/1/3 | 65.0 | 63.1 | 53.2 | 2774 | 1931 |
| 328-57-5 | | 56.9 | 43.1 | 0/1/4 | 66.7 | 63.4 | 43.8 | 2976 | 2140 |
| 328-57-6 | | 51.4 | 48.6 | 0/1/5 | 65.7 | 63.2 | 39.0 | 3083 | 2229 |
| 328-57-7 | 16.8 | 45.9 | 37.3 | 0.3/0.7/3 | 61.9 | 58.9 | 44.2 | 2947 | 1947 |
| 328-57-8 | 14.9 | 40.8 | 44.2 | 0.3/0.7/4 | 60.7 | 57.2 | 36.6 | 12645 | 7136 |
| 328-57-9 | 13.4 | 36.8 | 49.8 | 0.3/0.7/5 | 58.1 | 43.0 | 29.9 | 3075 | 2051 |
| | | | | High Mw set with no BMP in IPA as solvent | | | | | |
| 328-57-10 | 60 | | 40 | 1/0/3 | 40.7 | 22.6 | 13.9 | 12320 | 5544 |
| 328-57-11 | 52.9 | | 47.1 | 1/0/4 | 47.5 | 25.2 | 16.3 | 12400 | 6774 |
| 328-57-12 | 47.4 | | 52.6 | 1/0/5 | 34.2 | 22.4 | 8.6 | 14825 | 7623 |
| 328-57-13 | | 63.8 | 36.2 | 0/1/3 | 70.8 | 64.3 | 43.5 | 11915 | 3986 |
| 328-57-14 | | 56.9 | 43.1 | 0/1/4 | 67.5 | 56.1 | 40.7 | 12725 | 5464 |
| 328-57-15 | | 51.4 | 48.6 | 0/1/5 | 67.6 | 51.0 | 39.1 | 13185 | 6340 |
| 328-57-16 | 16.8 | 45.9 | 37.3 | 0.3/0.7/3 | 53.2 | 52.1 | 34.8 | 12015 | 5049 |
| 328-57-17 | 14.9 | 40.8 | 44.2 | 0.3/0.7/4 | 58.5 | 47.6 | 40.4 | 11630 | 4973 |
| 328-57-18 | 13.4 | 36.8 | 49.8 | 0.3/0.7/5 | 57.1 | 54.3 | 32.6 | 3109 | 2160 |

2. Solubility of 5% Polymer in Water:

Table SSP 2 below shows the results of mixing 0.5 gram of the polymers prepared in Table SSP 1 and 9.5 gram DI water, heating the mixture to 70 to 80° C. for about 1 hr, or shaking the hot mixture, and maintaining the mixture at 70-80° C. for 30-60 minutes. The hot mixture was hand shaken to mix. The resulting mixture was held at 70-80° C. for 30-60 min, and its solubility and clarity is reported in Table SSP 2.

The mixture was transferred to a 25° C. oven overnight, and Table SSP 2 records whether or not a gel formed.

TABLE SSP 2

| Gel ID | Interlimer | SCC/COOH molar ratio | Intelimer g | DI water g | Uniformly dispersible in water at 80 C.? | Gel at 25 C.? |
|---|---|---|---|---|---|---|
| 328-79-1 | 328-57-1 | 1/3 | 0.50 | 9.5 | yes | yes |
| 328-79-2 | 328-57-2 | 1/4 | 0.50 | 9.5 | yes | yes |
| 328-79-3 | 328-57-3 | 1/5 | 0.50 | 9.5 | yes | no |
| 328-79-4 | 328-57-4 | 1/3 | 0.50 | 9.5 | no | no |
| 328-79-5 | 328-57-5 | 1/4 | 0.50 | 9.5 | yes | yes |
| 328-79-6 | 328-57-6 | 1/5 | 0.50 | 9.5 | yes | no |
| 328-79-7 | 328-57-7 | 1/3 | 0.50 | 9.5 | almost yes | yes |
| 328-79-8 | 328-57-8 | 1/4 | 0.50 | 9.5 | yes | yes |
| 328-79-9 | 328-57-9 | 1/5 | 0.50 | 9.5 | yes | no |
| 328-79-10 | 328-57-10 | 1/3 | 0.50 | 9.5 | no | no |
| 328-79-11 | 328-57-11 | 1/4 | 0.50 | 9.5 | no | no |
| 328-79-12 | 328-57-12 | 1/5 | 0.50 | 9.5 | no | no |
| 328-79-13 | 328-57-13 | 1/3 | 0.50 | 9.5 | no | no |
| 328-79-14 | 328-57-14 | 1/4 | 0.50 | 9.5 | yes | no |
| 328-79-15 | 328-57-15 | 1/5 | 0.50 | 9.5 | no | no |
| 328-79-16 | 328-57-16 | 1/3 | 0.50 | 9.5 | no | no |
| 328-79-17 | 328-57-17 | 1/4 | 0.50 | 9.5 | yes | no |
| 328-79-18 | 328-57-18 | 1/5 | 0.50 | 9.5 | no | no |

3. Solubility of 10% Polymer in Water:

The procedure of 2 was repeated, but using a mixture of 1.0 gram polymer and 9.0 gram DI water. The results are recorded in Table SSP 3 below.

TABLE SSP 3

| Gel ID | Intelimer | SCC/COOH molar ratio | Intelimer g | DI water g | Uniformly dispersible in water at 80 C.? | Gel at 25 C.? |
|---|---|---|---|---|---|---|
| 328-80-1 | 328-57-1 | 1/3 | 1.00 | 9.00 | almost yes | yes |
| 328-80-2 | 328-57-2 | 1/4 | 1.00 | 9.00 | yes | yes |
| 328-80-3 | 328-57-3 | 1/5 | 1.00 | 9.00 | yes | yes |
| 328-80-4 | 328-57-4 | 1/3 | 1.00 | 9.00 | no | no |
| 328-80-5 | 328-57-5 | 1/4 | 1.00 | 9.00 | yes | yes |
| 328-80-6 | 328-57-6 | 1/5 | 1.00 | 9.00 | yes | yes |
| 328-80-7 | 328-57-7 | 1/3 | 1.00 | 9.00 | no | no |
| 328-80-8 | 328-57-8 | 1/4 | 1.00 | 9.00 | yes | yes |
| 328-80-9 | 328-57-9 | 1/5 | 1.00 | 9.00 | yes | yes |
| 328-80-10 | 328-57-10 | 1/3 | 1.00 | 9.00 | phase separated | no |
| 328-80-11 | 328-57-11 | 1/4 | 1.00 | 9.00 | phase separated | no |
| 328-80-12 | 328-57-12 | 1/5 | 1.00 | 9.00 | phase separated | no |

TABLE SSP 3-continued

| Gel ID | Intelimer | SCC/COOH molar ratio | Intelimer g | DI water g | Uniformly dispersible in water at 80 C.? | Gel at 25 C.? |
|---|---|---|---|---|---|---|
| 328-80-13 | 328-57-13 | 1/3 | 1.00 | 9.00 | phase separated | no |
| 328-80-14 | 328-57-14 | 1/4 | 1.00 | 9.00 | no | no |
| 328-80-15 | 328-57-15 | 1/5 | 1.00 | 9.00 | phase separated | no |
| 328-80-16 | 328-57-16 | 1/3 | 1.00 | 9.00 | phase separated | no |
| 328-80-17 | 328-57-17 | 1/4 | 1.00 | 9.00 | no | no |
| 328-80-18 | 328-57-18 | 1/5 | 1.00 | 9.00 | phase separated | no |

4. Emulsions

Canola oil (4.2 gram) and a solution of each of the polymers in Table SSP 1 in DI water (0.51 gram polymer in 10 gram DI water) were separately heated to 70-80° C. for 30 min. The warm Canola oil was poured into the warm aqueous polymer solution and immediately mixed with a homogenizer for 1 min while cooling in an ice bath. The resulting emulsion was kept at 25° C. overnight. Table SSP 4 reports the results.

Emulsion Formulation

| ID | Intelimer | SCC/COOH molar ratio | wt g | DI water g | Canola oil g | Uniformly dispersible in water at 80 C.? | stable emulsion at 25 C. after 2 days? | flowable at 25 C.? |
|---|---|---|---|---|---|---|---|---|
| 328-81-1 | 328-57-1 | 1/3 | 0.5145 | 9.996 | 4.190 | mostly yes | yes | no |
| 328-81-2 | 328-57-2 | 1/4 | 0.5145 | 9.996 | 4.190 | yes | yes | no |
| 328-81-3 | 328-57-3 | 1/5 | 0.5145 | 9.996 | 4.190 | yes | no | no |
| 328-81-4 | 328-57-4 | 1/3 | 0.5145 | 9.996 | 4.190 | mostly yes | no | yes |
| 328-81-5 | 328-57-5 | 1/4 | 0.5145 | 9.996 | 4.190 | yes | yes | no |
| 328-81-6 | 328-57-6 | 1/5 | 0.5145 | 9.996 | 4.190 | yes | no | yes |
| 328-81-7 | 328-57-7 | 1/3 | 0.5145 | 9.996 | 4.190 | mostly yes | no | no |
| 328-81-8 | 328-57-8 | 1/4 | 0.5145 | 9.996 | 4.190 | yes | yes | no |
| 328-81-9 | 328-57-9 | 1/5 | 0.5145 | 9.996 | 4.190 | yes | no | yes |
| 328-81-10 | 328-57-10 | 1/3 | 0.5145 | 9.996 | 4.190 | phase separated | yes | yes |
| 328-81-11 | 328-57-11 | 1/4 | 0.5145 | 9.996 | 4.190 | no | no | yes |
| 328-81-12 | 328-57-12 | 1/5 | 0.5145 | 9.996 | 4.190 | phase separated | no | yes |
| 328-81-13 | 328-57-13 | 1/3 | 0.5145 | 9.996 | 4.190 | no | no | no |
| 328-81-14 | 328-57-14 | 1/4 | 0.5145 | 9.996 | 4.190 | no | yes | yes |
| 328-81-15 | 328-57-15 | 1/5 | 0.5145 | 9.996 | 4.190 | phase separated | no | yes |
| 328-81-16 | 328-57-16 | 1/3 | 0.5145 | 9.996 | 4.190 | phase separated | yes | yes |
| 328-81-17 | 328-57-17 | 1/4 | 0.5145 | 9.996 | 4.190 | no | yes | yes |
| 328-81-18 | 328-57-18 | 1/5 | 0.5145 | 9.996 | 4.190 | phase separated | no | yes |

5. Additional Polymers.

Three additional polymers were prepared using a method similar to that in Example 1.

(A) A copolymer prepared from C18 A/AA/C1A, molar ratio 1/3.5/0.5, exhibited significant opacity similar to standard SCC polymer. On the first heat, it had a melting temperature of about 46° C. and a heat of fusion of about 43 J/g. On the second heat, it had a Tp of about 43° C. and a heat of fusion of about 37 J/g. It had a much lower viscosity than the C18A/AA, molar ratio 1/4, polymer. This result shows the influence of polymer viscosity in allowing the crystallizing side chains to align and crystallize.

(B) A copolymer prepared from C18A and acrylamide, molar ratio 1/4, is a clear crystalline polymer. On the first heat, it had a melting temperature of about 23° C. and a heat of fusion of about 19 J/g. On the second heat, it had a Tp of about 22° C. and a heat of fusion of about 20 J/g.

(C) A copolymer of C18A/AA (molar ratio 1/4)/MCR-M17 containing 5 weight percent MCR-M17 is a translucent polymer at room temperature. On the first heat, it had a melting temperature of about 39° C. and a heat of fusion of about 30 J/g. On the second heat, it had a Tp of about 38° C. and a heat of fusion of about 27 J/g.

Additional Disclosure and Examples of the Use of CYC Carriers in Agriculture

Through the use of CYSC polymers of this invention, the rate of release of pesticides on seed coatings, seed treatments and soil treatments can be controlled. In this case seed coatings refer to seed coating polymers which are CYSC polymers which are designed to regulate release of actives, in this case pesticides (fungicides, insecticides, biocides and the like). These polymers are typically emulsion copolymers as described in U.S. Pat. No. 7,175,832, awarded to Landec Corporation and other art, U.S. Pat. No. 5,129,180 to Landec Corporation. Seed treatments utilize preformed CYSC polymers with added pesticide or use of CYSC polymers pre-mixed with pesticides and added to existing seed treatment materials common in the agricultural industry to treat seeds prior to planting. Soil treatments are common as materials added to soil, for example, fertilizer, insecticides, fungicides and the like. In this case we are mixing CYSC polymers with these pesticides in order to control the rate of release of these pesticides in the soil. The ability to prolong release of pesticides over a long period in the early stages of seed germination and seed emergence and early plant growth is preferred as controlled release allows one of maybe a few applications to provide seed and early plant protection as compared to many or multiple treatments and applications to provide the same protection benefit as a controlled release application. The CYSC polymers whether in an emulsion form and high in molecular weight or as the CYSC polymers of lower molecular weight are particularly well suited for the controlled release of pesticides in the early treatment—during seed germination and emergence and early plant development of the agricultural crop involved.

In addition to the use of high and low molecular weight CYSC polymers, the self assembly techniques of this invention involve self assembly with small amounts of crystalline fatty ether alcohol additives mixed with an emulsion CYSC copolymer. These crystalline additives enhance the crystallization of the side chain crystalline emulsion copolymers, thereby, providing a strong formulating tool to regulate release of an active, in this case a pesticide, from an emulsion copolymer seed coating treatment.

Also, in addition to the use of the high and low molecular weight CYSC polymers by themselves or in combination with self assembly techniques of this invention for agricultural application, the use of these CYSC polymers with our without self assembly, may be also combined with the use of the aforementioned CYSC compound of this invention, for example, polyhydroxy compounds, i.e.—sorbitol, with an n-alkyl carboxylic acid (or the like) in which the n-alkyl moiety contains at least 14 carbon atoms, preferably 18-30 or 18-22 carbon atoms.

In a similar manner a lower molecular weight preformed CYSC polymer can be mixed with an active, a pesticide, and then added as a solid suspension of particles to an existing seed treatment solution to provide a controlled release of pesticide at the surface of the seed after application of the seed treatment. In the case of seed coating or treatment materials the CYSC acrylates or the CYSC emulsion copolymers have a Tm, melting point, set at a range where the pest infiltration is at its greatest stress level to the plants. Once the polymer— as an additive with pesticide or as the seed treatment coating polymer—passes from crystalline to amorphous as it goes through its melting point, a bolus release of desired pesticide is then available to attack crop pests at the critical time when these pesticides are needed. As a result more judicious and efficient use of pesticide is employed using these CYSC polymers as the controlling device for release of pesticide(s).

Therefore, somewhat different in preference of CYSC polymer selection than with the drug delivery polymers, polymers for use in seed treatment may be very high in molecular weight as the seed coating polymer or may be low in molecular weight similar to the desired drug delivery polymers. In the latter case these low molecular weight CYSC polymers are then applied as solid particle additives in an already preformed seed treatment where a conventional coating polymer is available as the seed treatment polymer:

a. Lower molecular weight CYSC acrylate/pesticide matrix additives to seed treatments
  b. Higher molecular weight emulsion copolymer CYSC acrylate/pesticide seed coatings Background and Scope of Use of CYSC Polymers in Agricultural Seed Treatment & Coatings for Controlled Release of Pesticides and Other Bioactives This present invention relates to the use of polymer and polymer formulations for use in controlled release of active ingredients, particularly the use of temperature activated side chain crystalline polymers either by themselves or in conjunction with other additives that can form non-covalently bound self assembled systems. Such systems can be systematically varied to tailor release profiles of active ingredients particularly useful for controlled release applications in agriculture for control of diseases and pests.

Controlled release systems have been used in several fields including medicine, agriculture and several other areas. As agricultural productivity has increased with improved genetics and trait technologies it has become more and more important to produce the seeds and the growing plants to reach their maximum yield potential and protect them from diseases and pest throughout the growing season. Many of the fungicides, insecticides and other actives are increasingly applied on seeds to ensure maximum efficacy of these actives. It would be advantageous to further enhancing the efficacy of these chemicals by controlling their release rates to (a) have the protection available to the seeds/plants for extended periods of time, (b) have the actives available in time to coincide with the pest infestation during the growing season, (c) target the actives in the zone around the plants, (d) potentially reduce phytotoxic effects of the active in high concentrations around the seed and (e) bind the chemicals to the polymer coating and reduce active ingredient leaching into water and thereby reduce contamination in run-off water in streams and ponds.

This present invention uses to advantage two aspects of the side chain crystalline polymers (CYSC Polymers):

(a) Effective use of the reversible crystalline/amorphous changes of the polymers where below the melt temperature (Tm) of the polymer in its non-permeable crystalline state the polymer effectively restricts the release of the active and above the Tm in its amorphous state the polymer can rapidly increase the release rate compared to the crystalline state, and
(b) The ability of amphiphilic additives to form co-crystalline systems obtained by the non-covalent self assembly of the amphiphile with the alkyl side chain of the polymers where below the Tm it improves the barrier to release and above the Tm the amphiphilc molecules (or low molecular amphiphilic polymers) enhance the release rate of the actives by providing newly created pathways or vias for the active molecule and/or act as a co-solvent for the active molecules and essentially act as permeation enhancers to further increase the release rates comparable to the release rates of the base polymer The formulations and polymeric systems of the current invention can be used to control the release of fungicides that are commonly used in the industry such as Thiram, Fludioxaonil, Captan, Rival, and Apron and insecticides such as imidacloprid, chlothianidin, dinotefuran and thiomethoxam. The active/polymer combination can be delivered on the seed as a seed coating, as a matrixed active used in conjunction with other seed treatments and seed treatment polymers.

The following describes the work done in the past several months to demonstrate the concept and compares the release properties of the polymers and the effect of amphiphilic additives in enhancing the release properties of active materials. All the work in this study has been conducted using a colored dye as the probe molecule to mimic the behavior of active compounds. The probe molecule is a red azo dye Allura Red, Food Red-40 (disodium 6-hydroxy-5-((2-methoxy-5-methyl-4-sulfophenyl)azo)-2-naphthalene-sulfonate). A 4% solution was prepared in water and used for mixing with the polymers.

Polymers: The studies were done using water based emulsions of side chain crystalline polymers developed as seed coating polymers (earlier patents by reference). Emulsion polymers of the type described can be prepared with varying properties depending on the monomer composition, particle size, Tm, hardness, crosslinking levels and other process conditions. A representative selection of the polymers was used in the initial study and is listed in slide 1. In addition to these polymers the study also included commercially available latex polymers selected from a group of latex polymers that include acrylic, styrene-acrylics, vinyl acetates, ethylene-vinyl acetates, urethane-acrylics, ethylene-vinyl chloride and other polymers used in coating applications. The polymers with their trade names were evaluated in this study as comparisons with SCC polymers are listed in Slide 2.

Amphiphilic Additives: The amphiphilc additives chosen in this study primarily consisted of liner alcohol ethoxylates where the hydrocarbon chain length and the level of ethoxylation can be systematically varied. Examples of other amphiphiles studied include linear alcohols and alkylamine ethoxylates. Early work has studied a C14-C18 system and EO in the range of 2 to 25 for the fatty crystalline ether alcohol additive to provide self assembly for enhanced crystallization of the emulsion CYSC polymer. Also included in this work was a low MW polymer (C18EO3MA/MAA 70/30) that also acts similar to the amphiphile described above in modulating the release rates. A list of some of the amphiphiles used is listed in slide 3.

In various embodiments the CYSC polymer amphiphile is an additive that can co-crystallize with CYSC polymers at or below the melting temperature of the polymers. The additive can be an amphiphilic molecule of the type RX where R is a liner alkyl chain of lengths 12 to 22 carbon atoms, preferably 16-22, and more preferably 16-18 carbon atoms; X is a hydrophilic functional group chosen from among the following: a) Alcohol, ethoxylates (with varying degree of ethoxylation 0-25) preferably in the range of 0-10 and more preferably in the range of 2-6; b) Anionic surfactant and cationic surfactant head groups; Specific hydrophilic functional groups that can be designed that will be complementary to the active ingredient to be used with these polymer films; c) Small block copolymers of alkyl (meth)acrylates and methacrylic acid where the alkyl acrylates can additionally contain hydrophilic groups such as ethylene oxide groups of varying lengths connecting the alkyl group to the acrylic backbone; and where the methacrylic acid can be replaced by other acid acrylates, cationic acrylates, amides, hydroxy functional acrylates etc.

Experimental Methods

Preparation of colorant Solution: Red 40 dye was prepared as a 4% solution in water.

Qualitative visual standards were prepared from this solution by successive dilution to the theoretically calculated amount based on 2 sq. inches of a 3 mil wet film cast on Laneta Charts. The standards were on a 0-5 scale with 5 representing 100% release.

Polymer solutions: The polymers with differing % solids were adjusted to 38% solids and to 14 g of this solution was added 1.68 g of a 4% solution of the dye to obtain a final solution at 34% solids.

Dissolution of amphiphiles: A solution of the amphiphile was prepared as a 40% solution in 1:1 or 2:1 propanol/water. The solvent choice was dependent on the solubility of the additive in water. Higher propanol ratios were used for additives with lower solubility in water.

Preparation of polymer/amphiphile solutions: For example, to 12 g C3A polymer (47.16% solids) in a sample vial was added 0.71 g of a 40% solution of SA-2 (stearyl alcohol-2 ethoxylates) slowly with mixing and the solids adjusted to 38% by the addition of 2.93 g of water. To this was added 1.68 g of a 4% solution of the Red 40 dye. The samples were mixed for 10 min, the vial loosely capped and heated in the oven at 50 C for 30 min and then cooled to ambient temperature.

Preparation of substrates: All the samples used in this study were cast as a 3 mil wet film from a 34% solids solution on a Laneta Chart using a 3 mil bird bar. The cast films were immediately transferred a 50 C oven and dried for 30 min. After cooling to room temperature 2 sq inch films were cut and placed into a vial containing 20 g of water and evaluated for the release rates over a period of 7-10 days.

Release rate studies: Vials were prepared for all the samples in the set and placed in incubators maintained at various temperatures. Studies were conducted typically at 10 and 30 C. Additional experiments were also conducted at 18 C and 25 C on some of the studies. At periodic time intervals the samples were removed from the incubator and the release was recorded by comparing with the color standards described above. Data are plotted on total release as a function of time for each of the sample at each of the temperatures or as a function of temperature at several time intervals.

Summary of results: Release profiles of SCC polymers: The two key properties that influence release rates of SCC polymers are Tm and particle size with the polymer morphoplogy also playing a role that is less well understood at this time. Slides 4 and 5 show the release profiles of different SCC polymers (along with two non SCC controls) as a function of time at 30 C and as a difference between permeabilities at 30 and 10 respectively. While there is a general trend that smaller particle size shows a slower release rate at 30 C, other properties such as monomer composition and cross linking levels also play a role in the measured release rates. Most of the polymers other than those with particle size <100 nm release at comparable rates when measured at 30 C. When the difference between 30 C and 10 C release rates are compared D1G, 337-40 and 311-60 show the highest difference between 10 and 30 C thus showing the differences based on polymer properties and a method to regulate the release rates as a function of polymer properties. Thus specific polymers can be designed depending on the desired release rates. Slide 6 clearly demonstrates the influence of Tm and polymer properties on the release rates as a function of temperature. The data is plotted as total release after 112 h. They can be classified into three different groups, the first group with the increased release by polymer with Tm in the 10-13 C range with particle sizes in the range of 100-150 nm. The second class is the C3A polymer (Tm=20) that shows considerable release below 25 C presumably due to its high particle size and a hard cross-linked shell that results in a poorly cohesive film (Note: this polymer was specifically designed for early plant corn applications). The third group of polymers (D1G and D3J) are 20 C polymers with particle sizes around 100 nm that form tight films and do not show any release at 18 C but show increasing release rates at 25 C and 30 C. This graph clearly demonstrates the influence of Tm on release rates as a function of temperature and additionally the influence of particle size and polymer morphology.

Influence of amphiphiles: Incorporation of amphiphilic surfactants into the emulsion polymer particles influences the crystallinity of the polymer system by a non-covalent self assembly of the hydrophobic portion of the amphiphiles with the alkyl side chain of the polymer. This can be determined by the changes in Tm and heat of fusion by DSC measurements.

In the current scope of work it is intended to develop the ability to make use of these amphiphiles to regulate release rates of actives by minimizing the release rates below the switch temperatures compared to the base polymers and increasing the release rates above the switch temperature. Slides 7-9 illustrate the effect of amphiphilic content on the release rates at two temperatures 30 and 10 C as well as the difference in the release rates between 10 and 30 which is a measure of the switch. Five different amphiphiles are chosen for this experiment with the hydrocarbon lengths of 16 or 18 carbons and between 2-10 ethoxylates. At 30 C the release rates are comparable for all the systems but at 10 C the longer chain lower ethoxylates (SA-2 and CA-2) show the least permeability and the CA-10 with 10 ethoxylate groups shows the highest permeability, that is considerably greater than the polymer system thus indicative of a poor co-crystallization due to the large number of ethoxylate groups. Slide 9 shows that SA-2 has the biggest influence on the switch (difference between release rates at 30 and 10) while CA-10 has the poorest switch lower than the base polymer itself due to its increased hydrophilicity.

The initial phase of this study has utilized a water soluble colorant as the probe molecule. The next step is to incorporate imidacloprid as the active into these formulations and develop analytical techniques for the detection of imidicaloprid and developing release profiles as a function of polymer, amphiphile and imidacloprid loading rates. A successful development will allow us to design controlled release system that can be tailored to match the active release with the timing of pest infestation through a number of mechanisms as illustrated by the different release profiles shown in slide 10

Controlled Release of Imidacloprid Using CYSC Polymers

As a specific example of how this technology is applicable for a specific insecticide for use on high volume seed crops—especially cotton, soybean and corn—the following study outlines how imidacloprid can be incorporated with the CYSC Polymers of this invention to provide controlled release properties.

Imidaclopid: Imidacloprid is a systemic, chloro-nicotinyl insecticide with soil, seed and foliar uses for the control of sucking insects including rice hoppers, aphids, thrips, whiteflies, termites, turf insects, soil insects and some beetles. It is most commonly used on rice, cereal, maize, potatoes, vegetables, sugar beets, fruit, cotton, hops and turf, and is especially systemic when used as a seed or soil treatment. The chemical works by interfering with the transmission of stimuli in the insect nervous system. Specifically, it causes a blockage in a type of neuronal pathway (nicotinergic) that is more abundant in insects than in warm-blooded animals (making the chemical selectively more toxic to insects than warm-blooded animals). This blockage leads to the accumulation of acetylcholine, an important neurotransmitter, resulting in the insect's paralysis, and eventually death.

Physical Properties:

Appearance: Colorless crystals with a weak characteristic odor.

Chemical Name: 1-(6-chloro-3-pyridylmethyl)-N-nitroimidazolidin-2-ylideneamine, 1-[(6-chloro-3-pyridinyl)methyl]-N-nitro-2-imidazolidinimine.

CAS Number: 13826-41-3

Molecular Weight: 255.7

Water Solubility: 0.51 g/l (200 degrees C.)

Solubility in Other Solvents: @ 20 degrees C.: dichloromethane—50.0-100.0 g/l; isopropanol—1.0-2.0 g/l; toluene—0.5-1.0 g/l; n-hexane—<0.1 g/l; fat—0.061 g/100 g Melting Point: 136.4-143.8 degrees C., 143.8 degrees C. (crystal form 1) 136.4 degrees C. (crystal form 2)

Vapor Pressure: 0.2 uPa (20 degrees C.) (1.5×10 to the minus 9 mmHg)

Partition Coefficient: 0.57 (22 degrees C.). (1)

Imidacloprid Application Rates:

Corn: Imidacloprid in its commercial formulation is used at two rates on corn 2.7 fl. oz/80MK (0.6 mg Al/kernel) unit and 6.0 fl. oz/80 mk units (1.34 mg Al/kernel). The lower rate is used for control of secondary insect pests such as flea beetles, seed corn maggot, thrips, wireworm and a number of other pests. The higher rate is specifically used for control of later season pest corn rootworm. While most of the commercial applications are now using Poncho and Crusier as insecticides it would be desirable to develop a slow release formulation that can control early season pests as well as rootworm control later in the growing season.

Cotton: Imidacloprid is used to provide early season protection to seedlings from thrips and aphids. The application rate of Gaucho 600 formulation (Bayer) is a maximum of 12.8 fl. oz./100 wt which translates into 0.375 mg Al/kernel assuming 4,500 seeds/lb.

Soybeans: Imidacloprid is used for protection against damage by seed corn maggot and to reduce feeding damage caused by soybean aphids and over-wintering bean leaf beetles. The recommended use rate is 1.6-3.2 fl. oz. per 100 wt of seed of the Gauch 600 formulation. This translates into a maximum dose of 0.16 mg Al/kernel of seed assuming 3000 seeds/lb.

Application methods: There are two basic approaches to matrix delivery of imidacloprid using CYSC polymers (a) delivered as a seed coating applied directly on the seed and (b) as a matrix suspension delivered as a component of seed treatment formulations. Applications as seed treatment will primarily be based on emulsion polymers while application as a seed treatment component can be in the form of emulsion polymer matrix or as a matrix polymer with low molecular weight CYSC polymers. The low molecular weight polymer offers an attractive method to have polymers with a diverse range of functional groups incorporated in the polymer such as alkyl ethoxylates.

Loading rates: The following considerations should be taken into account in determining the loading rates of imidacloprid on each of the crops:

- The rate of polymer should be low enough that the polymer-active can be applied easily on the seed using a one pass process with minimal process equipment requirements
- The rate of polymer should be low enough that it does not affect the germination characteristics of the seed
- The polymer/active ratio should be such that initial release due to surface effects should be minimal unless desired otherwise
- Based on the above considerations and the application rates it may be desirable to focus on active loading rates of 20-45% of the active which is higher than traditional release systems
- If only lower loading rates are achievable the polymer levels have to be increased and formulated to adjust for germination characteristics.

Polymer Selection: Based on initial studies of release rates the key properties of the emulsion polymers that influence release rates are particle size and Tm of the polymers. In addition, polymer morphology can be varied depending on the level of cross-linking and using core-shell technology. Once the release criteria is established the polymer is formulated with additives and other polymers for ease of application and delivery on the seed.

The initial list of polymers for evaluation include, as examples only since a full range of CYSC polymers is possible:

- Emulsion CYSC polymer, 20 C Tm core shell, 200 nm
- Emulsion CYSC polymer, 20 C Tm, Core shell, 90 nm
- Emulsion CYSC polymer: 20 C Tm, with secondary monomer variations Emulsion CYSC polymer: 10 C Tm, 100 nm core shell 0 Tm analog of Emulsion CYSC polymer (replacing C16A with C12A)

Low molecular weight CYSC polymers also are suitable for controlled release when premixed with imidacloprid and added to an already formulated seed treatment.

Amphiphilic additives: Use of amphiphilic additives in conjunction with CYSC polymers can potentially serve two distinct purposes in the design of controlled release systems for imidacloprid (a) amphiphilic additives can co-crystallize by non covalent self assembly with the side chains of the polymer and below the switch temperature can reduce permeability of the resulting film to water thus restricting the release of the imidacloprid and (b) can act as a permeation enhancer above the switch temperature by creating vias in the film and as carriers of the active away from the film into the soil or into the seed. Linear alcohol ethoxylates with hydrocarbon lengths of 16-18 carbons and from 2-10 ethoxylates are the preferred amphiphilic crystalline additives for agricultural use in this invention. The additives are used at 5-10% levels based on total solids of the CYSC polymer. The additive can also potentially be used as a carrier for incorporation of the imidacloprid (which has very limited solubility in water) in conjunction with additional co-solvents.

Experimental Methods

Analytical Methods:

Differential Scanning Calorimeter (DSC): DSC will be used to study the crystalline behavior of polymers, their interaction with amphiphilic additives and the influence of imidacloprid on co-crystallinity of the polymer/amphiphile systems:

Step 1: Installation of DSC system and methods development

Step 2: Crystallinity studies of CYSC polymers and effects of various amphiphilic additives to understand the influence of alkyl chain length and the hydrophilic group on non-covalent self assembly as measured by heat of fusion and Tm Step 3: Influence of imidacloprid loading rates on crystalline behavior of SCC polymers and CYSC polymer/amphiphile additive systems Step 4: Evaluation of crystallinity of CYSC polymer/amphiphile crystalline additive/imidacloprid systems after release studies to study the release of amphiphile and imidacloprid as a function of time at different temperatures UV-Vis Spectrophotometer: Spectrophotometric studies of the release rates of imidacloprid is the most efficient technique to characterize release rates from cast films.

High performance Liquid Chromatography (HPLC): HPLC is the preferred method of assay for evaluating the effectiveness of these CYSC polymers in seed treatment and seed coating controlled release application.

Key Issues and Challenges: The initial studies of polymer and amphiphiles and their influence on modulating release of a probe molecule (water soluble food colorant Red#40) have helped validate theoretical concepts of co-crystallinity and its influence on release rates as well as influence of polymer properties (tm and particle size) on the release rates.

Incorporation of imidacloprid into aqueous emulsions: Due its limited water solubility imidacloprid needs to be delivered into the aqueous emulsion by one of: (a) preparing a solution of the imidacloprid in a suitable co-solvent and then dispersing into the polymer, (b) preparation of an aqueous suspension of imidacloprid using appropriate surfactants and possibly co-solvents and then mixing with the emulsions and (c) dispersion of fine particle size imidacloprid (0.1-2 micron) into the emulsion polymers. Ideally both the amphiphile and the imidacloprid should diffuse into the hydrophobic CYSC polymer particles or alternatively can be isolated in the matrix of the CYSC polymer amphiphile additive mixture when applied as a film.

Loading rates: The theoretical loading rates of imidacloprid can range from 20-45% based on the assumption of a 0.5% add-on of the polymer onto seed so as to maintain seed germination characteristics. Effective release of the active may potentially reduce the loading rates of actives required for effective control of pests.

Quantitative release of active and effective timing of control: It is desirable to have a quantitative release of imidacloprid for maximum effectiveness and lower cost. Appropriate choice of the amphiphilic additive and its interaction with imidacloprid can help achieve quantitative release of the insecticide.

The CYSC polymers together with appropriate crystalline amphiphile additives modulate release rates of actives including fungicides and insecticides. This approach enables the design of systems depending on the release rates desired based on temperature and time. Among the possible profiles are:

1) Burst release triggered by temperature
2) Sustained release triggered above the Tm of the polymer
3) Initial release followed by sustained release over a period of time
4) Initial release followed by burst release as a function of temperature.

Slides Showing Controlled Release

Below are several tables showing data for the use of CYC carriers in agriculture.

TABLE AG 1

| SCC Polymer Characteristics | | | | | | | | | | | |
|---|---|---|---|---|---|---|---|---|---|---|---|
| Polymer | PS | Tm | Core Sh | pH | Sw R. | Gel Fr. | Heat Cap | % SCC | % ROH | X link | % shell |
| C3A | 185 | 19.5 | Y | 7.3 | 13.5 | 81 | 29.75 | 73.6 | 42.2 | 0.71 | 17.0% |
| D1G | 100 | 19.8 | N | 7.5 | 13 | 87 | 29.5 | 90 | 51.2 | 0.77 | 0 |
| D3J | 100 | 20.7 | N | 7.5 | 13 | 89 | 30 | 89.8 | 51.5 | 0.80 | 0 |
| 337-40 | 120 | 10.0 | Y | 7.0 | 13.8 | 88 | 18.5 | 71.4 | 54.8 | 0.60 | 15.0% |
| 311-148 | 93 | 20.9 | Y | 7.2 | — | — | 30 | 77.3 | 43.2 | 0.60 | 16.7% |
| M0578 | 81 | −14.0 | N | 5.7 | 18.9 | 86.8 | 10.8 | 90.6 | 35.5 | 0.67 | 0 |
| 279-188 | 143 | 13.0 | N | 7.1 | 11.1 | 89.5 | 27.6 | 85.4 | 58.4 | 0.79 | 0 |
| 229-56 | 184 | 13.8 | Y | 6.8 | 12.6 | 90.6 | 45.1 | 78.4 | 48.8 | 0.65 | 14% |
| M0503 | 178 | 11.7 | N | 6.5 | 10.2 | 92.9 | 36 | 89.1 | 66.8 | 0.70 | 0 |
| S0501 | 167 | 14.1 | N | 6.3 | 10.6 | 90.1 | 34 | 89 | 56.7 | 0.79 | 0 |

TABLE AG 2

Commercial Polymers

| Polymer | Manufacturer | Type | Tg, ° C. | Particle Size (nm) |
|---|---|---|---|---|
| Optive 110 | BASF | Acrylic | 18 | 140 |
| Neocar820 | | Acrylic | 20 | 70 |
| Neocar441 | | Acrylic | 23 | 250 |
| Airflex 4500 | Air Products | EVCl | 14 | |
| Flexbond325 | Air Products | EVAc | | |
| Rhoplex CS-4000 | Rohm and Haas | Acrylic | 32 | 120 |

TABLE AG 3

| | | Type Chemistry | Tm2 | HLB |
|---|---|---|---|---|
| Alcohols | | | | |
| 1 | Dodecanol, 98% | C12OH | 26.0 | |
| 2 | Lanette 14 | C14OH | 37.0 | |
| 3 | 1-Hexadecanol (99%) | C16OH | 53.5 | |
| Ethoxylated Alcohols | | | | |
| 1 | Novel 16-3 | C16OPOE3 | 28.8 | 11 to 12 |
| 2 | Ethal CA-2 | C16OPOE2 | 44.0 | 9 to 10 |
| 3 | Ethal CSA-3 | C1618OPOE3 | 42.6 | 13 to 14 |
| 4 | Ethal CSA-10 | C1618OPOE10 | | 11 to 12 |
| 5 | Ethal CSA-12 | C1618OPOE12 | 38.0 | 12 to 13 |
| 6 | Ethal CSA-20 | C1618OPOE20 | 47.8 | 15.4 |
| 7 | Ethal SA-2 | C18OPOE2 | 48.3 | 7 to 8 |
| 8 | Ethal 3328 | C1218OPOE3 | | 8.1 |
| 9 | Lutensol AT25 | c16C18OPOE25 | | 16 |
| 10 | Tomadol900 | Simialr to NP9 | | 13.1 |
| Amines | | | | |
| 1 | Ethox SAM-2 MON0818 Ethomeen T/20 | C18NPOE2 RN-POE RN-POE | 47.8 | 4.9 |
| Polymers | | | | |
| 1 | 337-20E (325-175) | C18POE2MA/MAA | 22.7 | |

The invention claimed is:

1. A composition which comprises an end cap crystalline (ECC) polymer and a release material associated with the ECC polymer, the release material being (1) one or more bioactive materials which are useful in agricultural applications and which are selected from the group consisting of fertilizers, biocides, insecticides and fungicides or (2) one or more additives which are useful in personal care compositions and which are selected from the group consisting of UV absorbers, fragrances, biocides, antimicrobial agents, germicides, antioxidants, preservatives, disinfectants, enzymes, nutrients and minerals, wherein the ECC polymer (A) comprises a plurality of polymeric molecules each of which consists essentially of
(i) a polymer backbone which comprises a plurality of repeating units having the formula

—$CF^1F^2$—CO—O—         (1)

wherein
$F^1$ is hydrogen and $F^2$ is hydrogen or methyl, the repeating units being the same or different, and
(ii) at least one terminal unit which has the formula -b-Cy         (2)

the Cy moieties in said terminal units providing at least 50% by weight of the Cy moieties in the polymeric molecules, and Cy being a moiety which is (a) associated with other Cy moieties to provide the ECC polymer with crystallinity and (b) is a moiety which consists of (i) an n-alkyl moiety containing 14-50 carbon atoms, or (ii) a moiety which consists of an n-alkyl moiety containing 14-50 carbon atoms and a polyoxyalkylene moiety, and b is a bond or a moiety which has a valence of at least 2, which links the Cy moiety to the polymer backbone and which optionally contains additional Cy moieties;

wherein each terminal unit having formula (2) is a moiety selected from the group consisting of
(2A) moieties (i) in which b is a bond, (ii) which have the formula —Cy and (iii) which are directly linked to the terminal —CO—O— moiety of one of the repeating units having formula (1),
(2B) moieties (i) in which b is a moiety having the formula —O—CO—, (ii) which have the formula —O—CO-Cy and (iii) which are directly linked to the terminal —$CF^1F^2$— moiety of one of the repeating units having formula (1), and
(2C) moieties (i) in which b is a moiety having the formula —$R_{pbalc}$—O—CO—, (ii) which have the formula —$R_{pbalc}$—O—CO-Cy where $R_{pbalc}$ is the residue of a polyol of and (iii) which are directly linked to the terminal —CO—O— moiety of one of the repeating units having formula (1); and
(B) has a crystalline melting temperature, Tp, of at least 0° C. and a heat of fusion, ΔH, of at least 3 J/g which result from association of the Cy moieties, Tp and ΔH being measured on a differential scanning calorimeter.

2. A composition according to claim 1 wherein the ECC polymer
(A) has a crystalline melting temperature, Tp, of at least 40° C., an onset of melting temperature, To, such that the value of (Tp–To) is less than $Tp^{0.7}$, and a heat of fusion of at least 5 J/g, Tp, To and ΔH being measured on a differential scanning calorimeter (DSC) and
(B) has a number average molecular weight, Mn, of less than 10,000.

3. A composition according to claim 1 wherein at least some of the polymeric molecules contain at least three Cy moieties, and the polymer has a heat of fusion of at least 10 J/g.

4. A composition according to claim 1 wherein at least one of the Cy moieties includes a polyoxyalkylene moiety.

5. A composition according to claim 1
wherein Cy is a moiety which consists of an n-alkyl moiety containing 18-24 carbon atoms, and
wherein the ECC polymer
(i) has a crystalline melting temperature, Tp, of at least 40° C., an onset of melting temperature, To, such that the value of (Tp–To) is less than 10° C., and a heat of fusion of at least 5 J/g, Tp, To and the heat of fusion being measured on a differential scanning calorimeter; and
(ii) has a number average molecular weight, Mn, of less than 8,000.

6. A composition which comprises an end cap crystalline (ECC) polymer and a release material associated with the ECC polymer, the release material being (1) one or more bioactive materials which are useful in agricultural applications and which are selected from the group consisting of fertilizers, biocides, insecticides and fungicides or (2) one or more additives which are useful in personal care compositions and which are selected from the group consisting of UV absorbers, fragrances, biocides, antimicrobial agents, germicides, antioxidants, preservatives, disinfectants, enzymes, nutrients and minerals, wherein the ECC polymer (1) comprises a plurality of polymeric molecules each of which consists essentially of
  (i) a polymer backbone which comprises a plurality of repeating units having the formula $$-CF^1F^2-CO-O-  \quad (1)$$

wherein
  $F^1$ is hydrogen and $F^2$ is hydrogen or methyl, the repeating units being the same or different, and
  (ii) at least one terminal unit which has the formula $$-b\text{-Cy} \quad (2)$$

the Cy moieties in said terminal units providing at least 50% by weight of the Cy moieties in the polymeric molecules, and
  Cy being a moiety which is associated with other Cy moieties to provide the ECC polymer with crystallinity and being a moiety which consists of (1) an n-alkyl moiety containing 18-24 carbon atoms or (2) an n-alkyl moiety containing 18-24 carbon atoms and a polyoxyalkylene unit, and
  b being a bond or a moiety which has a valence of at least 2 and which links the Cy moiety to the polymer backbone, and which optionally contains additional Cy moieties;
  wherein each terminal unit having formula (2) is a moiety selected from the group consisting of
  (2A) moieties (i) in which b is a bond, (ii) which have the formula -Cy and (iii) which are directly linked to the terminal —CO—O—moiety of one of the repeating units having formula (1),
  (2B) moieties (i) in which b is a moiety having the formula —O—CO—, (ii) which have the formula —O—CO-Cy and (iii) which are directly linked to the terminal —CF$^1$F$^2$—moiety of one of the repeating units having formula (1), and
  (2C) moieties (i) in which b is a moiety having the formula —R$_{pbalc}$—O—CO —, (ii) which have the formula —R$_{pbalc}$—O—CO-Cy where R$_{pbalc}$ is i the residue of a polyol, and (iii) which are directly linked to the terminal —CO—O—moiety of one of the repeating units having formula (1), and
(B) has a crystalline melting temperature, Tp, of at least 0° C. and a heat of fusion, ΔH, of at least 3 J/g which result from association of the Cy moieties, Tp and ΔH being measured on a differential scanning calorimeter.

7. A composition according to claim 6 wherein at least one of the terminal units in the ECC polymer has formula 2C and b is a moiety having a formula selected from the group consisting of

—CH$_2$—CH(OH)—CH$_2$—O—CO— and —CH$_2$—CH(O—CO-Cy)—CH$_2$—O—CO—.

8. A composition according to claim 6 wherein the ECC polymer is the reaction product of a method which comprises the steps of (A) reacting
  i) a preformed polymer which comprises a plurality of repeating units having the formula (1) and which has a terminal carboxyl group, and
  (ii) a polyol, and
(B) reacting the product of step (A) with a carboxylic acid, acid chloride or anhydride containing said Cy moiety.

9. A composition according to claim 6 wherein the ECC polymer is the reaction product of starting materials consisting of
  (i) a preformed polymer which comprises a plurality of repeating units having the formula (1) and which has a terminal carboxyl group, and
  (ii) an alcohol containing said Cy moiety.

10. A composition according to claim 6 wherein the ECC polymer is the reaction product of
  (i) a preformed polymer which comprises a plurality of repeating units having the formula (1) and which has a terminal hydroxyl group, and
  (ii) a carboxylic acid, acid chloride or anhydride containing said Cy moiety.

11. A composition according to claim 6 wherein the ECC polymer is the reaction product of a method which comprises the steps of
(A) reacting
  (i) a preformed polymer which comprises a plurality of repeating units having the formula (1) and which has a terminal hydroxyl group, and
  (ii) a dibasic carboxylic acid or anhydride, and
(B) reacting the product of step (A) with an alcohol containing said Cy moiety.

12. A composition according to claim 1 wherein the release material is selected from the group consisting of fertilizers, insecticides and fungicides.

13. A composition according to claim 12 wherein the release material is one or more of Thiram, fludioxonil, Captan, pentachloronitrobenzene, 2-[(2,6-dimethylphenyl)-(2-methoxy-1-oxoethy)amino] propanoic acid methyl ester, imidacloprid, chlothianidin, dinotefuran and thiomethoxam.

14. A composition according to claim 1 which is selected from the group consisting of deodorants, anti-perspirants, lipsticks, makeups, lotions, creams, oil-in-water emulsions, water-in-oil emulsions, hair care compositions, color care compositions, skin care compositions, sun care compositions, hair styling compositions, hair restyling compositions, shampoos, skin conditioners, nail varnishes, hand creams, night renewal creams, body milks and lotions, light facial creams, protective day creams, liquid moisturizing emulsions, and products designed to remove makeup.

15. A composition according to claim 1 wherein the ECC polymer is mixed with hyaluronic acid.

16. a composition according to claim 1 wherein the release material is an insecticide.

17. A composition according to claim 1 wherein the release material is a fungicide.

18. A composition according to claim 1 which is selected from the group consisting of lipsticks, hair care compositions, hair styling compositions, hair restyling compositions, nail varnishes, and products designed to remove makeup.

19. A method of releasing the release material from a release composition as claimed in claim 1 which comprises subjecting the composition to conditions which change the association between the release material and the ECC polymer.

20. A method of making a release composition as claimed in claim 1 which comprises mixing the release material and the ECC polymer, wherein the release material has a maximum temperature to which it can be exposed without damage, and the release material is mixed with the ECC polymer at a temperature at which the polymer is liquid and which is below the maximum temperature.

21. A method according to claim 20 wherein the mixing is carried out in the absence of any liquid other than the ECC polymer.

\* \* \* \* \*